(12) United States Patent
Lee et al.

(10) Patent No.: US 10,961,521 B2
(45) Date of Patent: Mar. 30, 2021

(54) RECOMBINANT MICROORGANISM FOR PRODUCING POLYHYDROXYALKANOATE

(71) Applicant: KOREA ADVANCED INSTITUTE OF SCIENCE AND TECHNOLOGY, Daejeon (KR)

(72) Inventors: Sang Yup Lee, Daejeon (KR); Jung Eun Yang, Daejeon (KR); Si Jae Park, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 16/483,426

(22) PCT Filed: Feb. 26, 2018

(86) PCT No.: PCT/KR2018/002305
§ 371 (c)(1),
(2) Date: Aug. 4, 2019

(87) PCT Pub. No.: WO2018/159965
PCT Pub. Date: Sep. 7, 2018

(65) Prior Publication Data
US 2019/0352622 A1 Nov. 21, 2019

(30) Foreign Application Priority Data

Feb. 28, 2017 (KR) ........................ 10-2017-0026266
Dec. 15, 2017 (KR) ........................ 10-2017-0172899

(51) Int. Cl.
*C12N 9/10* (2006.01)
*C12P 7/62* (2006.01)
*C12N 9/04* (2006.01)

(52) U.S. Cl.
CPC ............ *C12N 9/13* (2013.01); *C12N 9/0006* (2013.01); *C12N 9/1029* (2013.01); *C12P 7/625* (2013.01); *C12Y 101/01036* (2013.01)

(58) Field of Classification Search
None
See application file for complete search history.

(56) References Cited

U.S. PATENT DOCUMENTS

| 5,292,860 | A | 3/1994 | Kakogawa Ts et al. |
| 6,143,952 | A | 11/2000 | Srienc et al. |
| 2013/0288325 | A1 | 10/2013 | Liao et al. |
| 2014/0325709 | A1* | 10/2014 | Plesch .................. C12P 1/00 800/298 |

FOREIGN PATENT DOCUMENTS

| JP | 2015000033 | A | 5/2015 |
| KR | 101273599 | B1 | 6/2013 |
| KR | 1020150142304 | A | 12/2015 |
| KR | 1020150142304 | B1 | 12/2015 |
| WO | WO9854329 | A1 | 12/1998 |
| WO | WO9961624 | A2 | 12/1999 |
| WO | WO0155436 | A1 | 8/2001 |
| WO | WO2008062996 | A1 | 5/2008 |
| WO | 2012061653 | A2 | 5/2012 |
| WO | 2012169819 | A2 | 12/2012 |

OTHER PUBLICATIONS

Chica et al. CurrOpin Biotechnol. Aug. 20005;16(4):378-84. (Year: 2005).*
Singh et al. Curr Protein PeptSci. 2017, 18, 1-11 (Year: 2017).*
Kizeretal. Appl Environ Microbiol. May 2008;74(10):3229-41. (Year: 2008).*
Pratheretal. Curr Opin Biotechnol. Oct. 2008;19(5):468-74. (Year: 2008).*
Saika et al. J Biosci Bioeng. Jun. 2014; 117(6):670-5. Epub Jan. 29, 2014. (Year: 2014).*
Srirangan et al. Sci Rep 6, 36470 (2016), pp. 1-11. (Year: 2016).*
Accession POAB92. Jul. 21, 1986. (Year: 1986).*
Accession C7EXK8. Sep. 22, 2009. (Year: 2009).*
Accession A0A0L9ZYW6. Nov. 11, 2015. (Year: 2015).*
Accession O52791. Sep. 5, 2012 (Year: 2012).*
Alignment of SEQ ID No. 23364 of US20140325709 to SEQ ID No. 12 (Year: 2014).*
Accession Q7LLW9. Oct. 14, 2008 (Year: 2008).*
Lemoigne, M., et al., "Fermentation Beta-Hydroxybutyrique Caracterisation et Evolution des Produits de Deshydratation et de Polymerisation de L'Acide Beta-Hydroxybutyrique", "Annales des Fermentations", 1940, pp. 527-536, vol. 5.
Lemoigne, M., et al., "Fermentation Beta-Hydroxybutyrique Caracterisation et Evolution des Produits de Deshydratation et de Polymerisation de L'Acide Beta-Hydroxybutyrique", "Annales des Fermentations", 1940, Page(s) English Abstract, vol. 5, No. 527-536.
Amos, D.A., et al., "Composition of Poly-beta-Hydroxyalkanoate from Syntrophomonas Wolfei Grown on Unsaturated Fatty Acid Substrates", "Archives of Microbiology", 1991, pp. 103-106, vol. 155
Brandl, H., et al., "Ability of the Phototrophic Bacterium Rhodospirillum Rubrum to Produce Various Poly (beta-Hydroxyalkanoates): Potential Sources for Biodegradable Polyesters", "Int. J. Biol. Macromol.", 1989, pp. 49-55, vol. 11.

(Continued)

*Primary Examiner* — Christian L Fronda
(74) *Attorney, Agent, or Firm* — Hultquist, PLLC; Steven J. Hultquist

(57) ABSTRACT

The present invention relates to a recombinant microorganism to which a gene coding for 2-hydroxyisocaproate-CoA transferase and a gene coding for polyhydroxyalkanoate synthase are introduced and which has a potential of producing polyhydroxyalkanoate bearing an aromatic monomer or a long-chain 2-HA monomer and a method for producing polyhydroxyalkanoate bearing an aromatic monomer or a long-chain 2-HA monomer, using the recombinant microorganism. According to the present invention, a biodegradable polymer bearing an aromatic monomer or a long-chain 2-HA monomer can be produced.

14 Claims, 10 Drawing Sheets
(8 of 10 Drawing Sheet(s) Filed in Color)
Specification includes a Sequence Listing.

(56) References Cited

OTHER PUBLICATIONS

Chae, C.G., et al., "Biosynthesis of Poly(2-Hydroxybutyrate-Co-Lactate) in Metabolically Engineered *Escherichia coli*", "Biotechnology and Bioprocess Engineering", 2016, pp. 169-174, vol. 21.
Choi, S., et al., "One-Step Fermentative Production of Poly(lactate-co-glycolate) From Carbohydrates in *Escherichia coli*", "Nature Biotechnology", Apr. 2016, pp. 435-440, vol. 34, No. 4.
Datsenko, K., et al., "One-step Inactivation of Chromosomal Genes in *Escherichia coil* K-12 Using PCR Products", "Proc. Natl. Acad. Sci. USA (PNAS)", Jun. 6, 2000, pp. 6640-6645, vol. 97, No. 12.
Desmet, M., et al., "Characterization of Intracellular Inclusions Formed by Pseudomonas Oleovorans During Growth on Octane", "Journal of Bacteriology", May 1983, pp. 870-878, vol. 154, No. 2.
Dickert, S., et al., "The Involvement of Coenzyme A Esters in the Dehydration of (R)-Phenyllactate to (E)-Cinnamate by Clostridium Sporogenes", "Eur. J. Biochem", 2000, pp. 3874-3884, vol. 267.
Doroshenko, V.G., et al., "Metabolic Engineering of *Escherichia coli* for the Production of Phenylalanine and Related Compounds", "Applied Biochemistry and Microbiology", 2015, pp. 733-750, vol. 51, No. 7.
Genbank, "Chain A, Crystal Structure of the Apo Forms of Rhodotorula Graminis D-Mandelate Dehydrogenase at 1.8a", "GenBank", Oct. 10, 2012, pp. 1-4: 2W2K_A.
Genbank, "Chorismate Mutase P-Prephenate Dehydratase [*Escherichia coli* K-12]", "GenBank", Apr. 19, 2010, pp. 1-2: ACT66712.
Genbank, "Hydroxymandelate Oxidase [synthetic construct]", "GenBank", Jun. 15, 2016, p. 1: ANJ44374.
Genbank, "PCZA361.1: Amycolatopsis Orientalis", "GenBank", Jul. 25, 2016, pp. 1-2: CAA11761.1.
Heider, J.,, "A New Family of CoA-Transferases", "FEBS Letters", 2001, pp. 345-349, vol. 509.
Jung, Y.K., et al., "Metabolic Engineering of *Escherichia Coli* for the Production of Polylactic Acid and Its Copolymers", "Biotechnology and Bioengineering", 2010, pp. 161-171, vol. 105, No. 1.
Kaneko, M., et al., "Cinnamate: Coenzyme A Ligase from the Filamentous Bacterium Streptomyces Coelicolor A3 (2)", "Journal of Bacteriology", Jan. 2003, pp. 20-27.
Kikuchi, Y., et al., "Mutational Analysis of the Feedback Sites of Phenylalanine-Sensitive 3-Deoxy-D-arabino-Heptulosonate-7-Phosphate Synthase of *Escherichia coli*", "Applied and Environmental Microbiology", Feb. 1997, pp. 761-762.
Kim, J., et al., "Characterization of (R)-2-Hydroxyisocaproate Dehydrogenase and a Family III Coenzyme A Transferase Involved in Reduction of L-Leucine to Isocaproate by Clostridium Difficile", "Applied and Environmental Microbiology", Sep. 2006, pp. 6062-6069, vol. 72, No. 9.
Knobloch, K., et al., "4-Coumarate: CoA Ligase from Cell Suspension Cultures of Petroselinum Hortense Hoffm.", "Archives of Biochemistry and Biophysics", 1977, pp. 237-248, vol. 184.
Langenbach, S., et al., "Functional expression of the PHA synthase gene phaC1 from Pseudomonas aeruginosa in *Escherichia coli* results in poly(3-hydroxyalkanoate) synthesis", "FEMS Microbiology Letters", 1997, pp. 303-309, vol. 150.
Lee, S.Y., "Bacterial Polyhydroxyalkanoates", "Biotechnology and Bioengineering", 1996, pp. 1-14, vol. 49.
Lee, K.H. et al., "Systems Metabolic Engineering of *Escherichia coli* for L-Threonine Production", "Molecular Systems Biology", 2007, pp. 1-9, vol. 3, No. 149.
Matsumoto, K., et al., "Biosynthesis of Glycolate-Based Polyesters Containing Medium-Chain-Length 3-Hydroxyalkanoates in Recombinant *Escherichia coli* Expressing Engineered Polyhydroxyalkanoate Synthase", "Journal of Biotechnology", 2011, pp. 214-217, vol. 156.
NCBI, "3-Deoxy-7-Phosphoheptulonate Synthase, Phe-sensitive [*Escherichia coli* str. K-12 substr. MG1655]", "NCBI", Oct. 11, 2018, pp. 1-3: NP_415275.1.
NCBI, "Lactate Dehydrogenase [Clostridium Botulinum]", "GenBank", Mar. 24, 2015, p. 1: WP_045540971.
Neumann, E., et al., "Gene Transfer into Mouse Lyoma Cells by Electroporation in High Electric Fields", "The EMBO Journal", Jun. 30, 1982, pp. 841-845, vol. 1, No. 7.
Palmeros, B., et al., "A family of removable cassettes designed to obtain antibiotic-resistance-free genomic modifications of *Escherichia . . .* ", "Gene", 2000, pp. 255-264, vol. 247.
Park, S.J., et al., "Metabolic Engineering of Ralstonia Eutropha for the Biosynthesis of 2-Hydroxyacid-Containing Polyhydroxyalkanoates", "Metabolic Engineering", 2013, pp. 20-28, vol. 20
Qi, Q., et al., "Synthesis of poly(3-hydroxyalkanoates) in *Escherichia coli* expressing the PHA synthase gene phaC2 from Pseudomonas aeruginosa: comparison of PhaC1 and PhaC2", "FEMS Microbiology Letters", 1997, pp. 155-162, vol. 157.
Qi, Q., et al., "Metabolic routing towards polyhydroxyalkanoic acid synthesis in recombinant *Escherichia coli* (fadR): inhibition of fatty acid B-oxidation by acrylic acid", "FEMS Microbiology Letters", 1998, pp. 89-94, vol. 167.
Tribe, D.E., et al., "Constitutive and Repressible Enzymes of the Common Pathway of Aromatic Biosynthesis in *Escherichia coli* K-12: Regulation of Enzyme Synthesis at Different Growth Rates", "Journal of Bacteriology", Sep. 1976, pp. 1085-1097, vol. 127, No. 3.
Yang, T., et al., "Biosynthesis of Polylactic Acid and its Copolymers Using Evolved Propionate CoA Transferase and PHA Synthase", "Biotechnology and Bioengineering", Jan. 1, 2010, pp. 150-160, vol. 105, No. 1.
Yang, T.H., et al., "Tailor-Made Type II Pseudomonas PHA Synthases and Their Use for the Biosynthesis of Polylactic Acid and its Copolymer in Recombinant *Escherichia coli*", "Appl. Microbiol. Biotechnol.", 2011, pp. 603-614, vol. 90.
Yang, J.E., et al., "One-Step Fermentative Production of Aromatic Polyesters from Glucose by Metabolically Engineered *Escherichia coli* Strains", "Nature Communications", 2018, pp. 1-9.
Zhou, H. et al., "Enhanced L-Phenylalanine Biosynthesis by Co-Expression of pheAfbr and aroFwt", "Bioresource Technology", 2010, pp. 4151-4156, vol. 101.
Matsumoto, K., et al., "Biosynthetic polyesters consisting of 2-hydroxyalkanoic acids: current challenges and unresolved questions", "Appl Microbiol Biotechnol", 2013, pp. 8011-8021, vol. 97, Publisher: Springer.

* cited by examiner

FIG. 2

SEQUENCE LISTING

<160> NUMBER OF SEQ ID NOS: 93

<210> SEQ ID NO 1
<211> LENGTH: 399
<212> TYPE: PRT
<213> ORGANISM: Artificial Sequence
<220> FEATURE:
<223> OTHER INFORMATION: Synthetic Construct

<400> SEQUENCE: 1

```
Met Leu Leu Glu Gly Val Lys Val Val Glu Leu Ser Ser Phe Ile Ala
1               5                   10                  15

Ala Pro Cys Cys Ala Lys Met Leu Gly Asp Trp Gly Ala Glu Val Ile
            20                  25                  30

Lys Ile Glu Pro Ile Glu Gly Asp Gly Ile Arg Val Met Gly Gly Thr
        35                  40                  45

Phe Lys Ser Pro Ala Ser Asp Asp Glu Asn Pro Met Phe Glu Leu Glu
    50                  55                  60

Asn Gly Asn Lys Lys Gly Val Ser Ile Asn Val Lys Ser Lys Glu Gly
65                  70                  75                  80

Val Glu Ile Leu His Lys Leu Leu Ser Glu Ala Asp Ile Phe Val Thr
                85                  90                  95

Asn Val Arg Val Gln Ala Leu Glu Lys Met Gly Ile Ala Tyr Asp Gln
            100                 105                 110

Ile Lys Asp Lys Tyr Pro Gly Leu Ile Phe Ser Gln Ile Leu Gly Tyr
        115                 120                 125

Gly Glu Lys Gly Pro Leu Lys Asp Lys Pro Gly Phe Asp Tyr Thr Ala
    130                 135                 140

Tyr Phe Ala Arg Gly Gly Val Ser Gln Ser Val Met Glu Lys Gly Thr
145                 150                 155                 160

Ser Pro Ala Asn Thr Ala Ala Gly Phe Gly Asp His Tyr Ala Gly Leu
                165                 170                 175

Ala Leu Ala Ala Gly Ser Leu Ala Ala Leu His Lys Lys Ala Gln Thr
            180                 185                 190

Gly Lys Gly Glu Arg Val Thr Val Ser Leu Phe His Thr Ala Ile Tyr
        195                 200                 205

Gly Met Gly Thr Met Ile Thr Thr Ala Gln Tyr Gly Asn Glu Met Pro
    210                 215                 220

Leu Ser Arg Glu Asn Pro Asn Ser Pro Leu Met Thr Thr Tyr Lys Cys
225                 230                 235                 240

Lys Asp Gly Arg Trp Ile Gln Leu Ala Leu Ile Gln Tyr Asn Lys Trp
                245                 250                 255
```

```
Leu Gly Lys Phe Cys Lys Val Ile Asn Arg Glu Tyr Ile Leu Glu Asp
                260                 265                 270

Asp Arg Tyr Asn Asn Ile Asp Ser Met Val Asn His Val Glu Asp Leu
            275                 280                 285

Val Lys Ile Val Gly Glu Ala Met Leu Glu Lys Thr Leu Asp Glu Trp
        290                 295                 300

Ser Ala Leu Leu Glu Glu Ala Asp Leu Pro Phe Glu Lys Ile Gln Ser
305                 310                 315                 320

Cys Glu Asp Leu Leu Asp Asp Glu Gln Ala Trp Ala Asn Asp Phe Leu
                325                 330                 335

Phe Lys Lys Thr Tyr Asp Ser Gly Asn Thr Gly Val Leu Val Asn Thr
            340                 345                 350

Pro Val Met Phe Arg Asn Glu Gly Ile Lys Glu Tyr Thr Pro Ala Pro
        355                 360                 365

Lys Val Gly Gln His Thr Val Glu Val Leu Lys Ser Leu Gly Tyr Asp
                370                 375                 380

Glu Glu Lys Ile Asn Asn Phe Lys Asp Ser Lys Val Val Arg Tyr
385                 390                 395

<210> SEQ ID NO 2
<211> LENGTH: 559
<212> TYPE: PRT
<213> ORGANISM: Artificial Sequence
<220> FEATURE:
<223> OTHER INFORMATION: Synthetic Construct

<400> SEQUENCE: 2

Met Ser Asn Lys Ser Asn Asp Glu Leu Lys Tyr Gln Ala Ser Glu Asn
1               5                   10                  15

Thr Leu Gly Leu Asn Pro Val Val Gly Leu Arg Gly Lys Asp Leu Leu
            20                  25                  30

Ala Ser Ala Arg Met Val Leu Arg Gln Ala Ile Lys Gln Pro Val His
        35                  40                  45

Ser Val Lys His Val Ala His Phe Gly Leu Glu Leu Lys Asn Val Leu
    50                  55                  60

Leu Gly Lys Ser Gly Leu Gln Pro Thr Ser Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Val Pro Pro Gln
    210                 215                 220
```

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
            245                 250                 255

Asn Pro Thr Lys Glu Gln Arg Glu Trp Gly Leu Ser Thr Tyr Ile Glu
        260                 265                 270

Ala Leu Lys Glu Ala Val Asp Val Thr Ala Ile Thr Gly Ser Lys
    275                 280                 285

Asp Val Asn Met Leu Gly Ala Cys Ser Gly Ile Thr Cys Thr Ala
290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
            325                 330                 335

Leu Phe Val Asn Glu Gln Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
            405                 410                 415

Lys Asn Asn Pro Leu Ile Arg Pro Asn Ala Leu Glu Val Cys Gly Thr
        420                 425                 430

Pro Ile Asp Leu Lys Gln Val Thr Ala Asp Ile Phe Ser Leu Ala Gly
        435                 440                 445

Thr Asn Asp His Ile Thr Pro Trp Lys Ser Cys Tyr Lys Ser Ala Gln
450                 455                 460

Leu Phe Gly Gly Asn Val Glu Phe Val Leu Ser Ser Ser Gly His Ile
465                 470                 475                 480

Gln Ser Ile Leu Asn Pro Pro Gly Asn Pro Lys Ser Arg Tyr Met Thr
            485                 490                 495

Ser Thr Glu Val Ala Glu Asn Ala Asp Glu Trp Gln Ala Asn Ala Thr
        500                 505                 510

Lys His Thr Asp Ser Trp Trp Leu His Trp Gln Ala Trp Gln Ala Gln
        515                 520                 525

Arg Ser Gly Glu Leu Lys Lys Ser Pro Thr Lys Leu Gly Ser Lys Ala
530                 535                 540

Tyr Pro Ala Gly Glu Ala Ala Pro Gly Thr Tyr Val His Glu Arg
545                 550                 555

<210> SEQ ID NO 3
<211> LENGTH: 1065
<212> TYPE: DNA
<213> ORGANISM: Artificial Sequence
<220> FEATURE:
<223> OTHER INFORMATION: Synthetic Construct

<400> SEQUENCE: 3
atgaattatc agaacgacga tttacgcatc aaagaaatca agagttact tcctcctgtc      60 gcattgctgg aaaaattccc cgctactgaa aatgccgcga atacggttgc ccatgcccga     120
aaagcgatcc ataagatcct gaaaggtaat gatgatcgcc tgttggttgt gattggccca    180

```
tgctcaattc atgatcctgt cgcggcaaaa gagtatgcca ctcgcttgct ggcgctgcgt    240
gaagagctga agatgagct  ggaaatcgta atgcgcgtct attttgaaaa gccgcgtacc    300
acggtgggct ggaaagggct gattaacgat ccgcatatgg ataatagctt ccagatcaac    360
gacggtctgc gtatagcccg taaattgctg cttgatatta cgacagcgg  tctgccagcg    420 gcaggtgagt ttctcaatat gatcacccca caatatctcg ctgacctgat gagctggggc    480
gcaattggcg cacgtaccac cgaatcgcag gtgcaccgcg aactggcatc agggctttct    540
tgtccggtcg gcttcaaaaa tggcaccgac ggtacgatta agtggctat  cgatgccatt    600 aatgccgccg gtgcgccgca ctgcttcctg tccgtaacga atgggggca  ttcggcgatt    660 gtgaatacca gcggtaacgg cgattgccat atcattctgc gcggcggtaa agagcctaac    720
tacagcgcga agcacgttgc tgaagtgaaa gaagggctga acaaagcagg cctgccagca    780
caggtgatga tcgatttcag ccatgctaac tcgtccaaac aattcaaaaa gcagatggat    840
gtttgtgctg acgtttgcca gcagattgcc ggtggcgaaa aggccattat tggcgtgatg    900
gtggaaagcc atctggtgga aggcaatcag agcctcgaga gcggggagcc gctggcctac    960
ggtaagagca tcaccgatgc ctgcatcggc tgggaagata ccgatgctct gttacgtcaa   1020
ctggcgaatg cagtaaaagc gcgtcgcggg taactgcagg catgc                   1065
```

<210> SEQ ID NO 4
<211> LENGTH: 1161
<212> TYPE: DNA
<213> ORGANISM: Artificial Sequence
<220> FEATURE:
<223> OTHER INFORMATION: Synthetic Construct

<400> SEQUENCE: 4

```
atgacatcgg aaaacccgtt actggcgctg cgagagaaaa tcagcgcgct ggatgaaaaa     60
ttattagcgt tactggcaga acggcgcgaa ctggccgtcg aggtgggaaa agccaaactg    120
ctctcgcatc gcccggtacg tgatattgat cgtgaacgcg atttgctgga agattaatt    180 acgctcggta agcgcaccac tctggacgcc cattacatta ctcgcctgtt ccagctcatc    240
attgaagatt ccgtattaac tcagcaggct ttgctccaac aacatctcaa taaaattaat    300
ccgcactcag cacgcatcgc ttttctcggc cccaaaggtt cttattccca tcttgcggcg    360
cgccagtatg ctgcccgtca ctttgagcaa ttcattgaaa gtggctgcgc caaatttgcc    420
gatattttta atcaggtgga aaccggccag gccgactatg ccgtcgtacc gattgaaaat    480
accagctccg gtgccataaa cgacgtttac gatctgctgc aacataccag cttgtcgatt    540
gttggcgaga tgacgttaac tatcgaccat tgtttgttgg tctccggcac tactgattta    600
tccaccatca atacggtcta cagccatccg cagccattcc agcaatgcag caaattcctt    660
aatcgttatc cgcactggaa gattgaatat accgaaagta cgtctgcggc aatggaaaag    720
gttgcacagg caaaatcacc gcatgttgct gcgttgggaa gcgaagctgg cggcactttg    780
tacggtttgc aggtactgga gcgtattgaa gcaaatcagc gacaaaactt cacccgattt    840
gtggtgttgg cgcgtaaagc cattaacgtg tctgatcagg ttccggcgaa accacgttg    900 ttaatggcga ccgggcaaca agccggtgcg ctggttgaag cgttgctggt actgcgcaac    960
cacaatctga ttatgccccg tctggaatca cgcccgattc acggtaatcc atgggaagag   1020
atgttctatc tggatattca ggccaatctt gaatcagcgg aaatgcaaaa agcattgaaa   1080
gagttagggg aaatcacccg ttcaatgaag gtattgggct gttacccaag tgagaacgta   1140
gtgcctgttg atccaacctg a                                             1161
```

<210> SEQ ID NO 5
<211> LENGTH: 1074
<212> TYPE: DNA
<213> ORGANISM: Artificial Sequence
<220> FEATURE:
<223> OTHER INFORMATION: Synthetic Construct

<400> SEQUENCE: 5

| | | | | | |
|---|---|---|---|---|---|
| atgcagaatt | ttgagataga | ctatgtagaa | atgtatgtgg | aaaatcttga | agtggctgca | 60 |
| tttagttggg | tcgataagta | tgcattcgcc | gttgccggta | caagccgtag | tgcggaccat | 120 |
| cgttcgattg | cgctacgcca | gggtcaagtg | acgttggtgt | tgacagaacc | aacgtcggat | 180 |
| cgtcatccgg | cggcggcata | tcttcagact | catggcgatg | gtgttgccga | catagcgatg | 240 |
| gcgacaagcg | atgtcgccgc | cgcttacgaa | gctgcagtac | gggcggggc | ggaagccgtt | 300 |
| cgcgcgccgg | gccagcactc | agaggcggct | gttactacgg | ccactatcgg | tggttttggc | 360 |
| gatgtggtac | atacccctgat | tcagcgcgac | ggaacatccg | ctgagttgcc | tccgggtttt | 420 |
| acaggctcta | tggatgtcac | taaccacgga | aaaggtgatg | tcgatttatt | gggcattgac | 480 |
| catttcgcga | tttgtctgaa | tgctggcgat | cttggtccca | ccgtggagta | ctacgaaaga | 540 |
| gcattaggtt | ttagacagat | ctttgatgaa | cacatagtcg | tcggtgcaca | ggcgatgaat | 600 |
| agtaccgtag | tgcaaagtgc | gtctggagct | gttaccctga | ccctgattga | acctgaccgc | 660 |
| aatgccgacc | caggccagat | cgacgagttt | ctcaaagatc | atcaagggc | aggagttcag | 720 |
| cacatcgcct | ttaatagcaa | cgatgcagtc | cgtgcagtaa | aggctttatc | agaaagggg | 780 |
| gtggagttct | taaaaacacc | ggggcgtat | tatgatctgc | tcggagagcg | tatcacgctg | 840 |
| cagacgcatt | cgttagatga | tctgcgggca | actaacgttc | tcgcagatga | agatcacggc | 900 |
| ggccaactgt | ttcagatttt | cactgcatcc | actcatccac | gtcatacgat | ttttttcgag | 960 |
| gtcatagaga | ggcaaggcgc | tggcactttc | ggatcatcca | atatcaaagc | cctgtatgag | 1020 |
| gccgttgaac | tggaacgcac | cgggcaatct | gaatttggag | ccgctcggcg | ataa | 1074 |

<210> SEQ ID NO 6
<211> LENGTH: 1134
<212> TYPE: DNA
<213> ORGANISM: Artificial Sequence
<220> FEATURE:
<223> OTHER INFORMATION: Synthetic Construct

<400> SEQUENCE: 6

| | | | | | |
|---|---|---|---|---|---|
| atgcgggaac | cactcacgct | cgatgatttc | gctcgattag | cacgcggaca | attacctgca | 60 |
| gctacttggg | atttcattgc | agggggcgcg | gggcgggaac | ggaccctcgc | tgctaacgaa | 120 |
| gccgtgtttg | gagctgttag | acttagaccc | agggcacttc | ctggcatcga | agaaccggac | 180 |
| acctctgtag | aagtgctcgg | ctcccggtgg | ccggcgccgg | ttggtattgc | gccggtagct | 240 |
| taccacgggc | tcgcgcatcc | agacggcgaa | cccgcgactg | ccgcggcggc | cggagcgcta | 300 |
| ggtctcccgt | tggtagttag | caccttttgcg | gggcgcagct | tagaagaggt | agcacgtgca | 360 |
| gctagcgcac | cgctgtggct | ccagctgtat | tgtttccgag | atcatgagac | aacacttggg | 420 |
| ctagcccgca | gagctcgcga | cagcggctat | caggctctgt | tgttaaccgt | cgacacaccg | 480 |
| tttactggac | gccggttacg | tgatctgcgt | aacggcttcg | cagtccctgc | tcacatcacc | 540 |
| ccagccaatc | tgactggtac | agcagcagca | ggctcagcca | ccccaggcgc | ccatagccgt | 600 |
| ctggcgtttg | atcgccgcct | tgattggtct | tttgttgccc | gcttaggagc | agcgagcgga | 660 |

| | |
|---|---|
| ctgccagtgc tggccaaagg cgtgctgacg gcgcctgatg ccgaggctgc ggtcgcggcg | 720 |
| ggcgtagccg gcatagttgt aagtaatcat gggggccgcc agctcgacgg cgcaccagca | 780 |
| acactggagg cgttgcccga agtggtgtcg gccgtgcgcg aagatgccc cgtcctcttg | 840 |
| gatggtggtg tcagaactgg ggccgatgtc ttagctgcat tagctctcgg tgcccgtgcc | 900 |
| gtcctggtcg gccgccctgc actgtatgca ctggctgttg ggggcgccag tggagtgcgc | 960 |
| agaatgctca cactgcttac agaggacttt gctgatacga tggtcttaac cggccatgca | 1020 |
| gcaactggta cgattggccc ggacaccctg gccccacccc accatgcccc tccgcaccat | 1080 |
| ggtccgccta ccgcgccacg cccggcgccg caccgagata ggagccatgg ataa | 1134 |

<210> SEQ ID NO 7
<211> LENGTH: 1047
<212> TYPE: DNA
<213> ORGANISM: Artificial Sequence
<220> FEATURE:
<223> OTHER INFORMATION: Synthetic Construct

<400> SEQUENCE: 7

| | |
|---|---|
| atgcctcgtc cgcgcgtcct tctcttaggc gaccccgctc gccatctcga cgacctctgg | 60 |
| agcgattttc agcaaaaatt tgaagtcatc cctgccaatc tgaccacaca cgatgggttt | 120 |
| aaacaagccc tgcgtgaaaa acgctatggc gatttttgaag ccatcattaa acttgccgtt | 180 |
| gaaaacggca cagagagcta tccctggaat gccgatttaa taagtcatct cccaagttcc | 240 |
| cttaaagttt ttgcagctgc cggcgcaggc ttcgactggc tcgaccttga tgcactcaac | 300 |
| gagagaggag tagcttttcgc caattctcgc ggggctggcg atactgctac atcagatctc | 360 |
| gcactgtact tgattctttc cgtattccgc ttagcgtcat actctgagcg agccgcgcgt | 420 |
| acgggcgatc cagaaacttt taatcgtgtt catctcgaaa ttggtaaatc agcacacaat | 480 |
| ccgcgcgggc acgtgctcgg cgctgtcgga ttgggcgcaa ttcagaaaga gatagcgagg | 540 |
| aaagcggtgc atggcctggg gatgaagtta gtctattatg atgtggcgcc tgcagatgca | 600 |
| gaaacggaaa aggcgctagg tgctgagcgg gttgactcgc tcgaagagct ggctagacgt | 660 |
| agcgattgtg tcagcgtgtc ggttccgtat atgaaattga cgcaccatct cattgatgaa | 720 |
| gccttctttg ccgcgatgaa accgggaagt cgcattgtta atactgcgcg tggtccagtg | 780 |
| atttcacagg atgcattgat agcagcgctc aaatctggaa aactgctcag tgccggctta | 840 |
| gacgtgcatg agttcgagcc acaggtgtcc aaagaactca ttgaaatgaa gcatgttaca | 900 |
| ctgactacac atatcggagg cgtagcgatt gaaaccttcc atgaatttga gcggttaacc | 960 |
| atgaccaaca tagatcgatt tcttctacag ggcaaaccgt tgctgacccc tgcgggtaaa | 1020 |
| gtatttgcgc cgtcatctgc tgcataa | 1047 |

<210> SEQ ID NO 8
<211> LENGTH: 350
<212> TYPE: PRT
<213> ORGANISM: Artificial Sequence
<220> FEATURE:
<223> OTHER INFORMATION: Synthetic Construct

<400> SEQUENCE: 8

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys

```
                35                  40                  45
Gly Asn Asp Asp Arg Leu Leu Val Val Ile Gly Pro Cys Ser Ile His
 50                  55                  60

Asp Pro Val Ala Ala Lys Glu Tyr Ala Thr Arg Leu Leu Ala Leu Arg
 65                  70                  75                  80

Glu Glu Leu Lys Asp Glu Leu Glu Ile Val Met Arg Val Tyr Phe Glu
                 85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
130                 135                 140

Leu Asn Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Gly Ala Pro His Cys
        195                 200                 205

Phe Leu Ser Val Thr Lys Trp Gly His Ser Ala Ile Val Asn Thr Ser
210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350

<210> SEQ ID NO 9
<211> LENGTH: 386
<212> TYPE: PRT
<213> ORGANISM: Artificial Sequence
<220> FEATURE:
<223> OTHER INFORMATION: Synthetic Construct

<400> SEQUENCE: 9

Met Thr Ser Glu Asn Pro Leu Leu Ala Leu Arg Glu Lys Ile Ser Ala
 1               5                  10                  15

Leu Asp Glu Lys Leu Leu Ala Leu Leu Ala Glu Arg Arg Glu Leu Ala
                 20                  25                  30

Val Glu Val Gly Lys Ala Lys Leu Leu Ser His Arg Pro Val Arg Asp
            35                  40                  45

Ile Asp Arg Glu Arg Asp Leu Leu Glu Arg Leu Ile Thr Leu Gly Lys
```

```
              50                  55                  60

Ala His His Leu Asp Ala His Tyr Ile Thr Arg Leu Phe Gln Leu Ile
    65                  70                  75                  80

Ile Glu Asp Ser Val Leu Thr Gln Gln Ala Leu Leu Gln Gln His Leu
                        85                  90                  95

Asn Lys Ile Asn Pro His Ser Ala Arg Ile Ala Phe Leu Gly Pro Lys
                    100                 105                 110

Gly Ser Tyr Ser His Leu Ala Ala Arg Gln Tyr Ala Ala Arg His Phe
                115                 120                 125

Glu Gln Phe Ile Glu Ser Gly Cys Ala Lys Phe Ala Asp Ile Phe Asn
            130                 135                 140

Gln Val Glu Thr Gly Gln Ala Asp Tyr Ala Val Pro Ile Glu Asn
    145                 150                 155                 160

Thr Ser Ser Gly Ala Ile Asn Asp Val Tyr Asp Leu Leu Gln His Thr
                    165                 170                 175

Ser Leu Ser Ile Val Gly Glu Met Thr Leu Thr Ile Asp His Cys Leu
                180                 185                 190

Leu Val Ser Gly Thr Thr Asp Leu Ser Thr Ile Asn Thr Val Tyr Ser
                195                 200                 205

His Pro Gln Pro Phe Gln Gln Cys Ser Lys Phe Leu Asn Arg Tyr Pro
            210                 215                 220

His Trp Lys Ile Glu Tyr Thr Glu Ser Thr Ser Ala Ala Met Glu Lys
    225                 230                 235                 240

Val Ala Gln Ala Lys Ser Pro His Val Ala Ala Leu Gly Ser Glu Ala
                    245                 250                 255

Gly Gly Thr Leu Tyr Gly Leu Gln Val Leu Glu Arg Ile Glu Ala Asn
                260                 265                 270

Gln Arg Gln Asn Phe Thr Arg Phe Val Val Leu Ala Arg Lys Ala Ile
                275                 280                 285

Asn Val Ser Asp Gln Val Pro Ala Lys Thr Thr Leu Leu Met Ala Thr
                    290                 295                 300

Gly Gln Gln Ala Gly Ala Leu Val Glu Ala Leu Leu Val Leu Arg Asn
    305                 310                 315                 320

His Asn Leu Ile Met Pro Arg Leu Glu Ser Arg Pro Ile His Gly Asn
                    325                 330                 335

Pro Trp Glu Glu Met Phe Tyr Leu Asp Ile Gln Ala Asn Leu Glu Ser
                340                 345                 350

Ala Glu Met Gln Lys Ala Leu Lys Glu Leu Gly Glu Ile Thr Arg Ser
                355                 360                 365

Met Lys Val Leu Gly Cys Tyr Pro Ser Glu Asn Val Val Pro Val Asp
    370                 375                 380

Pro Thr
    385

<210> SEQ ID NO 10
<211> LENGTH: 331
<212> TYPE: PRT
<213> ORGANISM: Artificial Sequence
<220> FEATURE:
<223> OTHER INFORMATION: Synthetic Construct

<400> SEQUENCE: 10

Met Lys Ile Leu Ala Tyr Cys Val Arg Pro Asp Glu Val Asp Ser Phe
    1               5                   10                  15

Lys Lys Phe Ser Glu Lys Tyr Gly His Thr Val Asp Leu Ile Pro Asp
```

```
            20                  25                  30
Ser Phe Gly Pro Asn Val Ala His Leu Ala Lys Gly Tyr Asp Gly Ile
            35                  40                  45

Ser Ile Leu Gly Asn Asp Thr Cys Asn Arg Glu Ala Leu Glu Lys Ile
 50                  55                  60

Lys Asp Cys Gly Ile Lys Tyr Leu Ala Thr Arg Ala Gly Val Asn
 65                  70                  75                  80

Asn Ile Asp Phe Asp Ala Ala Lys Glu Phe Gly Ile Asn Val Ala Asn
                 85                  90                  95

Val Pro Ala Tyr Ser Pro Asn Ser Val Ser Glu Phe Thr Ile Gly Leu
                100                 105                 110

Ala Leu Ser Leu Thr Arg Lys Ile Pro Phe Ala Leu Lys Arg Val Glu
                115                 120                 125

Leu Asn Asn Phe Ala Leu Gly Gly Leu Ile Gly Val Glu Leu Arg Asn
            130                 135                 140

Leu Thr Leu Gly Val Ile Gly Thr Gly Arg Ile Gly Leu Lys Val Ile
145                 150                 155                 160

Glu Gly Phe Ser Gly Phe Gly Met Lys Lys Met Ile Gly Tyr Asp Ile
                165                 170                 175

Phe Glu Asn Glu Glu Ala Lys Lys Tyr Ile Glu Tyr Lys Ser Leu Asp
                180                 185                 190

Glu Val Phe Lys Glu Ala Asp Ile Ile Thr Leu His Ala Pro Leu Thr
                195                 200                 205

Asp Asp Asn Tyr His Met Ile Gly Lys Glu Ser Ile Ala Lys Met Lys
            210                 215                 220

Asp Gly Val Phe Ile Ile Asn Ala Ala Arg Gly Ala Leu Ile Asp Ser
225                 230                 235                 240

Glu Ala Leu Ile Glu Gly Leu Lys Ser Gly Lys Ile Ala Gly Ala Ala
                245                 250                 255

Leu Asp Ser Tyr Glu Tyr Glu Gln Gly Val Phe His Asn Asn Lys Met
                260                 265                 270

Asn Glu Ile Met Gln Asp Asp Thr Leu Glu Arg Leu Lys Ser Phe Pro
            275                 280                 285

Asn Val Val Ile Thr Pro His Leu Gly Phe Tyr Thr Asp Glu Ala Val
            290                 295                 300

Ser Asn Met Val Glu Ile Thr Leu Met Asn Leu Gln Glu Phe Glu Leu
305                 310                 315                 320

Lys Gly Thr Cys Lys Asn Gln Arg Val Cys Lys
                325                 330

<210> SEQ ID NO 11
<211> LENGTH: 357
<212> TYPE: PRT
<213> ORGANISM: Artificial Sequence
<220> FEATURE:
<223> OTHER INFORMATION: Synthetic Construct

<400> SEQUENCE: 11

Met Gln Asn Phe Glu Ile Asp Tyr Val Glu Met Tyr Val Glu Asn Leu
1               5                   10                  15

Glu Val Ala Ala Phe Ser Trp Val Asp Lys Tyr Ala Phe Ala Val Ala
                20                  25                  30

Gly Thr Ser Arg Ser Ala Asp His Arg Ser Ile Ala Leu Arg Gln Gly
            35                  40                  45

Gln Val Thr Leu Val Leu Thr Glu Pro Thr Ser Asp Arg His Pro Ala
```

```
            50                  55                  60
Ala Ala Tyr Leu Gln Thr His Gly Asp Gly Val Ala Asp Ile Ala Met
 65                  70                  75                  80

Ala Thr Ser Asp Val Ala Ala Tyr Glu Ala Ala Val Arg Ala Gly
                 85                  90                  95

Ala Glu Ala Val Arg Ala Pro Gly Gln His Ser Glu Ala Ala Val Thr
                100                 105                 110

Thr Ala Thr Ile Gly Gly Phe Gly Asp Val Val His Thr Leu Ile Gln
            115                 120                 125

Arg Asp Gly Thr Ser Ala Glu Leu Pro Pro Gly Phe Thr Gly Ser Met
        130                 135                 140

Asp Val Thr Asn His Gly Lys Gly Asp Val Asp Leu Leu Gly Ile Asp
145                 150                 155                 160

His Phe Ala Ile Cys Leu Asn Ala Gly Asp Leu Gly Pro Thr Val Glu
                165                 170                 175

Tyr Tyr Glu Arg Ala Leu Gly Phe Arg Gln Ile Phe Asp Glu His Ile
                180                 185                 190

Val Val Gly Ala Gln Ala Met Asn Ser Thr Val Val Gln Ser Ala Ser
            195                 200                 205

Gly Ala Val Thr Leu Thr Leu Ile Glu Pro Asp Arg Asn Ala Asp Pro
        210                 215                 220

Gly Gln Ile Asp Glu Phe Leu Lys Asp His Gln Gly Ala Gly Val Gln
225                 230                 235                 240

His Ile Ala Phe Asn Ser Asn Asp Ala Val Arg Ala Val Lys Ala Leu
                245                 250                 255

Ser Glu Arg Gly Val Glu Phe Leu Lys Thr Pro Gly Ala Tyr Tyr Asp
                260                 265                 270

Leu Leu Gly Glu Arg Ile Thr Leu Gln Thr His Ser Leu Asp Asp Leu
            275                 280                 285

Arg Ala Thr Asn Val Leu Ala Asp Glu Asp His Gly Gly Gln Leu Phe
        290                 295                 300

Gln Ile Phe Thr Ala Ser Thr His Pro Arg His Thr Ile Phe Phe Glu
305                 310                 315                 320

Val Ile Glu Arg Gln Gly Ala Gly Thr Phe Gly Ser Ser Asn Ile Lys
                325                 330                 335

Ala Leu Tyr Glu Ala Val Glu Leu Glu Arg Thr Gly Gln Ser Glu Phe
                340                 345                 350

Gly Ala Ala Arg Arg
            355

<210> SEQ ID NO 12
<211> LENGTH: 377
<212> TYPE: PRT
<213> ORGANISM: Artificial Sequence
<220> FEATURE:
<223> OTHER INFORMATION: Synthetic Construct

<400> SEQUENCE: 12

Met Arg Glu Pro Leu Thr Leu Asp Asp Phe Ala Arg Leu Ala Arg Gly
 1               5                  10                  15

Gln Leu Pro Ala Ala Thr Trp Asp Phe Ile Ala Gly Gly Ala Gly Arg
                20                  25                  30

Glu Arg Thr Leu Ala Ala Asn Glu Ala Val Phe Gly Ala Val Arg Leu
            35                  40                  45

Arg Pro Arg Ala Leu Pro Gly Ile Glu Glu Pro Asp Thr Ser Val Glu
```

```
              50                  55                  60
Val Leu Gly Ser Arg Trp Pro Ala Pro Val Gly Ile Ala Pro Val Ala
 65                  70                  75                  80

Tyr His Gly Leu Ala His Pro Asp Gly Glu Pro Ala Thr Ala Ala Ala
                 85                  90                  95

Ala Gly Ala Leu Gly Leu Pro Leu Val Val Ser Thr Phe Ala Gly Arg
            100                 105                 110

Ser Leu Glu Glu Val Ala Arg Ala Ala Ser Ala Pro Leu Trp Leu Gln
        115                 120                 125

Leu Tyr Cys Phe Arg Asp His Glu Thr Thr Leu Gly Leu Ala Arg Arg
    130                 135                 140

Ala Arg Asp Ser Gly Tyr Gln Ala Leu Val Leu Thr Val Asp Thr Pro
145                 150                 155                 160

Phe Thr Gly Arg Arg Leu Arg Asp Leu Arg Asn Gly Phe Ala Val Pro
                165                 170                 175

Ala His Ile Thr Pro Ala Asn Leu Thr Gly Thr Ala Ala Ala Gly Ser
            180                 185                 190

Ala Thr Pro Gly Ala His Ser Arg Leu Ala Phe Asp Arg Arg Leu Asp
        195                 200                 205

Trp Ser Phe Val Ala Arg Leu Gly Ala Ala Ser Gly Leu Pro Val Leu
    210                 215                 220

Ala Lys Gly Val Leu Thr Ala Pro Asp Ala Glu Ala Ala Val Ala Ala
225                 230                 235                 240

Gly Val Ala Gly Ile Val Val Ser Asn His Gly Gly Arg Gln Leu Asp
                245                 250                 255

Gly Ala Pro Ala Thr Leu Glu Ala Leu Pro Glu Val Val Ser Ala Val
            260                 265                 270

Arg Gly Arg Cys Pro Val Leu Leu Asp Gly Gly Val Arg Thr Gly Ala
        275                 280                 285

Asp Val Leu Ala Ala Leu Ala Leu Gly Ala Arg Ala Val Leu Val Gly
    290                 295                 300

Arg Pro Ala Leu Tyr Ala Leu Ala Val Gly Gly Ala Ser Gly Val Arg
305                 310                 315                 320

Arg Met Leu Thr Leu Leu Thr Glu Asp Phe Ala Asp Thr Met Val Leu
                325                 330                 335

Thr Gly His Ala Ala Thr Gly Thr Ile Gly Pro Asp Thr Leu Ala Pro
            340                 345                 350

Pro His His Ala Pro Pro His His Gly Pro Pro Thr Ala Pro Arg Pro
        355                 360                 365

Ala Pro His Arg Asp Arg Ser His Gly
    370                 375

<210> SEQ ID NO 13
<211> LENGTH: 348
<212> TYPE: PRT
<213> ORGANISM: Artificial Sequence
<220> FEATURE:
<223> OTHER INFORMATION: Synthetic Construct

<400> SEQUENCE: 13

Met Pro Arg Pro Arg Val Leu Leu Leu Gly Asp Pro Ala Arg His Leu
 1               5                  10                  15

Asp Asp Leu Trp Ser Asp Phe Gln Gln Lys Phe Glu Val Ile Pro Ala
                 20                  25                  30

Asn Leu Thr Thr His Asp Gly Phe Lys Gln Ala Leu Arg Glu Lys Arg
```

```
                    35                  40                  45
Tyr Gly Asp Phe Glu Ala Ile Ile Lys Leu Ala Val Glu Asn Gly Thr
 50                  55                  60

Glu Ser Tyr Pro Trp Asn Ala Asp Leu Ile Ser His Leu Pro Ser Ser
 65                  70                  75                  80

Leu Lys Val Phe Ala Ala Gly Ala Gly Phe Asp Trp Leu Asp Leu
                 85                  90                  95

Asp Ala Leu Asn Glu Arg Gly Val Ala Phe Ala Asn Ser Arg Gly Ala
                100                 105                 110

Gly Asp Thr Ala Thr Ser Asp Leu Ala Leu Tyr Leu Ile Leu Ser Val
                115                 120                 125

Phe Arg Leu Ala Ser Tyr Ser Glu Arg Ala Ala Arg Thr Gly Asp Pro
130                 135                 140

Glu Thr Phe Asn Arg Val His Leu Glu Ile Gly Lys Ser Ala His Asn
145                 150                 155                 160

Pro Arg Gly His Val Leu Gly Ala Val Gly Leu Gly Ala Ile Gln Lys
                165                 170                 175

Glu Ile Ala Arg Lys Ala Val His Gly Leu Gly Met Lys Leu Val Tyr
                180                 185                 190

Tyr Asp Val Ala Pro Ala Asp Ala Glu Thr Glu Lys Ala Leu Gly Ala
                195                 200                 205

Glu Arg Val Asp Ser Leu Glu Glu Leu Ala Arg Arg Ser Asp Cys Val
210                 215                 220

Ser Val Ser Val Pro Tyr Met Lys Leu Thr His His Leu Ile Asp Glu
225                 230                 235                 240

Ala Phe Phe Ala Ala Met Lys Pro Gly Ser Arg Ile Val Asn Thr Ala
                245                 250                 255

Arg Gly Pro Val Ile Ser Gln Asp Ala Leu Ile Ala Ala Leu Lys Ser
                260                 265                 270

Gly Lys Leu Leu Ser Ala Gly Leu Asp Val His Glu Phe Glu Pro Gln
                275                 280                 285

Val Ser Lys Glu Leu Ile Glu Met Lys His Val Thr Leu Thr Thr His
290                 295                 300

Ile Gly Gly Val Ala Ile Glu Thr Phe His Glu Phe Glu Arg Leu Thr
305                 310                 315                 320

Met Thr Asn Ile Asp Arg Phe Leu Leu Gln Gly Lys Pro Leu Leu Thr
                325                 330                 335

Pro Ala Gly Lys Val Phe Ala Pro Ser Ser Ala Ala
                340                 345

<210> SEQ ID NO 14
<211> LENGTH: 30
<212> TYPE: DNA
<213> ORGANISM: Artificial Sequence
<220> FEATURE:
<223> OTHER INFORMATION: Synthetic Construct

<400> SEQUENCE: 14
cgcgcatatg agaaaggttc ccattattac                                      30

<210> SEQ ID NO 15
<211> LENGTH: 51
<212> TYPE: DNA
<213> ORGANISM: Artificial Sequence
<220> FEATURE:
<223> OTHER INFORMATION: Synthetic Construct
```

<400> SEQUENCE: 15
cgcgggatcc ttagtgatgg tgatggtggt gggacttcat ttccttcaga c          51

<210> SEQ ID NO 16
<211> LENGTH: 30
<212> TYPE: DNA
<213> ORGANISM: Artificial Sequence
<220> FEATURE:
<223> OTHER INFORMATION: Synthetic Construct

<400> SEQUENCE: 16
tacagaattc atgttccgca gcgagtacgc                                  30

<210> SEQ ID NO 17
<211> LENGTH: 53
<212> TYPE: DNA
<213> ORGANISM: Artificial Sequence
<220> FEATURE:
<223> OTHER INFORMATION: Synthetic Construct

<400> SEQUENCE: 17
tattcctgca ggttagtgat ggtgatggtg gtgtcgcggc tccctgagct gtc        53

<210> SEQ ID NO 18
<211> LENGTH: 18
<212> TYPE: DNA
<213> ORGANISM: Artificial Sequence
<220> FEATURE:
<223> OTHER INFORMATION: Synthetic Construct

<400> SEQUENCE: 18
tacatcgtca gcggcgcc                                               18

<210> SEQ ID NO 19
<211> LENGTH: 18
<212> TYPE: DNA
<213> ORGANISM: Artificial Sequence
<220> FEATURE:
<223> OTHER INFORMATION: Synthetic Construct

<400> SEQUENCE: 19
ggcgccgctg acgatgta                                               18

<210> SEQ ID NO 20
<211> LENGTH: 30
<212> TYPE: DNA
<213> ORGANISM: Artificial Sequence
<220> FEATURE:
<223> OTHER INFORMATION: Synthetic Construct

<400> SEQUENCE: 20
cgcgcatatg gaaaacaatg caaacatgtt                                  30

<210> SEQ ID NO 21
<211> LENGTH: 53
<212> TYPE: DNA
<213> ORGANISM: Artificial Sequence
<220> FEATURE:
<223> OTHER INFORMATION: Synthetic Construct

<400> SEQUENCE: 21
cgcgaagctt ttagtgatgg tgatggtggt gttttctttt gcgaaccatg ata        53

<210> SEQ ID NO 22
<211> LENGTH: 30

<212> TYPE: DNA
<213> ORGANISM: Artificial Sequence
<220> FEATURE:
<223> OTHER INFORMATION: Synthetic Construct

<400> SEQUENCE: 22
cgcggaattc atgaattatc agaacgacga                                30

<210> SEQ ID NO 23
<211> LENGTH: 30
<212> TYPE: DNA
<213> ORGANISM: Artificial Sequence
<220> FEATURE:
<223> OTHER INFORMATION: Synthetic Construct

<400> SEQUENCE: 23
tattaagctt ttacccgcga cgcgcttttta                               30

<210> SEQ ID NO 24
<211> LENGTH: 45
<212> TYPE: DNA
<213> ORGANISM: Artificial Sequence
<220> FEATURE:
<223> OTHER INFORMATION: Synthetic Construct

<400> SEQUENCE: 24
tatcaagctt acacaggaaa cagaaatgac atcggaaaac ccgtt               45

<210> SEQ ID NO 25
<211> LENGTH: 30
<212> TYPE: DNA
<213> ORGANISM: Artificial Sequence
<220> FEATURE:
<223> OTHER INFORMATION: Synthetic Construct

<400> SEQUENCE: 25
cgcgaagctt tcaggttgga tcaacaggca                                30

<210> SEQ ID NO 26
<211> LENGTH: 30
<212> TYPE: DNA
<213> ORGANISM: Artificial Sequence
<220> FEATURE:
<223> OTHER INFORMATION: Synthetic Construct

<400> SEQUENCE: 26
acaatctgat tatgccccgt ctggaatcac                                30

<210> SEQ ID NO 27
<211> LENGTH: 30
<212> TYPE: DNA
<213> ORGANISM: Artificial Sequence
<220> FEATURE:
<223> OTHER INFORMATION: Synthetic Construct

<400> SEQUENCE: 27
gtgattccag acggggcata atcagattgt                                30

<210> SEQ ID NO 28
<211> LENGTH: 45
<212> TYPE: DNA
<213> ORGANISM: Artificial Sequence
<220> FEATURE:
<223> OTHER INFORMATION: Synthetic Construct

<400> SEQUENCE: 28
tataggtacc acacaggaaa cagaaatggg gaccttcgtt attga    45

<210> SEQ ID NO 29
<211> LENGTH: 30
<212> TYPE: DNA
<213> ORGANISM: Artificial Sequence
<220> FEATURE:
<223> OTHER INFORMATION: Synthetic Construct

<400> SEQUENCE: 29
cgctgtcgac ttatcacttg tcatcgtcat    30

<210> SEQ ID NO 30
<211> LENGTH: 32
<212> TYPE: DNA
<213> ORGANISM: Artificial Sequence
<220> FEATURE:
<223> OTHER INFORMATION: Synthetic Construct

<400> SEQUENCE: 30
tataggatcc atgaaaatcc tggcgtattg cg    32

<210> SEQ ID NO 31
<211> LENGTH: 30
<212> TYPE: DNA
<213> ORGANISM: Artificial Sequence
<220> FEATURE:
<223> OTHER INFORMATION: Synthetic Construct

<400> SEQUENCE: 31
cgcgaagctt ttatttacaa acgcgctggt    30

<210> SEQ ID NO 32
<211> LENGTH: 30
<212> TYPE: DNA
<213> ORGANISM: Artificial Sequence
<220> FEATURE:
<223> OTHER INFORMATION: Synthetic Construct

<400> SEQUENCE: 32
cgcgctcgag gctgttgaca attaatcatc    30

<210> SEQ ID NO 33
<211> LENGTH: 30
<212> TYPE: DNA
<213> ORGANISM: Artificial Sequence
<220> FEATURE:
<223> OTHER INFORMATION: Synthetic Construct

<400> SEQUENCE: 33
cgcggagctc tgtagaaacg caaaaaggcc    30

<210> SEQ ID NO 34
<211> LENGTH: 47
<212> TYPE: DNA
<213> ORGANISM: Artificial Sequence
<220> FEATURE:
<223> OTHER INFORMATION: Synthetic Construct

<400> SEQUENCE: 34
tatacctgca ggacacagga aacagaaatg gaaaacaatg caaacat    47

<210> SEQ ID NO 35
<211> LENGTH: 32
<212> TYPE: DNA
<213> ORGANISM: Artificial Sequence

```
<220> FEATURE:
<223> OTHER INFORMATION: Synthetic Construct

<400> SEQUENCE: 35
tatgcctgca ggttagtgat ggtgatggtg gt                              32

<210> SEQ ID NO 36
<211> LENGTH: 49
<212> TYPE: DNA
<213> ORGANISM: Artificial Sequence
<220> FEATURE:
<223> OTHER INFORMATION: Synthetic Construct

<400> SEQUENCE: 36
tatacctgca ggacacagga aacagaaatg aaaatcctgg cgtattgcg            49

<210> SEQ ID NO 37
<211> LENGTH: 30
<212> TYPE: DNA
<213> ORGANISM: Artificial Sequence
<220> FEATURE:
<223> OTHER INFORMATION: Synthetic Construct

<400> SEQUENCE: 37
cgcgaagctt ttatttacaa acgcgctggt                                 30

<210> SEQ ID NO 38
<211> LENGTH: 30
<212> TYPE: DNA
<213> ORGANISM: Artificial Sequence
<220> FEATURE:
<223> OTHER INFORMATION: Synthetic Construct

<400> SEQUENCE: 38
cggccatatg cttttagaag gagttaaagt                                 30

<210> SEQ ID NO 39
<211> LENGTH: 53
<212> TYPE: DNA
<213> ORGANISM: Artificial Sequence
<220> FEATURE:
<223> OTHER INFORMATION: Synthetic Construct

<400> SEQUENCE: 39
tattgcggcc gcttagtgat ggtgatggtg gtgatatctt acaactttac tat       53

<210> SEQ ID NO 40
<211> LENGTH: 64
<212> TYPE: DNA
<213> ORGANISM: Artificial Sequence
<220> FEATURE:
<223> OTHER INFORMATION: Synthetic Construct

<400> SEQUENCE: 40
tattcctgca ggcggataac aatttcacac aggaaacaga attcatgctt ttagaaggag 60
ttaa                                                             64

<210> SEQ ID NO 41
<211> LENGTH: 30
<212> TYPE: DNA
<213> ORGANISM: Artificial Sequence
<220> FEATURE:
<223> OTHER INFORMATION: Synthetic Construct

<400> SEQUENCE: 41
```

```
cgcgcatatg ttaatatctt acaactttac                                      30

<210> SEQ ID NO 42
<211> LENGTH: 47
<212> TYPE: DNA
<213> ORGANISM: Artificial Sequence
<220> FEATURE:
<223> OTHER INFORMATION: Synthetic Construct

<400> SEQUENCE: 42
tattcctgca ggacacagga aacagaaatg cttttagaag gagttaa                   47

<210> SEQ ID NO 43
<211> LENGTH: 32
<212> TYPE: DNA
<213> ORGANISM: Artificial Sequence
<220> FEATURE:
<223> OTHER INFORMATION: Synthetic Construct

<400> SEQUENCE: 43
tatacctgca ggttaatatc ttacaacttt ac                                   32

<210> SEQ ID NO 44
<211> LENGTH: 45
<212> TYPE: DNA
<213> ORGANISM: Artificial Sequence
<220> FEATURE:
<223> OTHER INFORMATION: Synthetic Construct

<400> SEQUENCE: 44
tataggtacc acacaggaaa cagaaatgcg ggaaccactc acgct                     45

<210> SEQ ID NO 45
<211> LENGTH: 33
<212> TYPE: DNA
<213> ORGANISM: Artificial Sequence
<220> FEATURE:
<223> OTHER INFORMATION: Synthetic Construct

<400> SEQUENCE: 45
tataggatcc ttatccatgg ctcctatctc ggt                                  33

<210> SEQ ID NO 46
<211> LENGTH: 45
<212> TYPE: DNA
<213> ORGANISM: Artificial Sequence
<220> FEATURE:
<223> OTHER INFORMATION: Synthetic Construct

<400> SEQUENCE: 46
tataggatcc acacaggaaa cagaaatgcc tcgtccgcgc gtcct                     45

<210> SEQ ID NO 47
<211> LENGTH: 36
<212> TYPE: DNA
<213> ORGANISM: Artificial Sequence
<220> FEATURE:
<223> OTHER INFORMATION: Synthetic Construct

<400> SEQUENCE: 47
tatgcctgca ggttatgcag cagatgacgg cgcaaa                               36

<210> SEQ ID NO 48
<211> LENGTH: 45
<212> TYPE: DNA
<213> ORGANISM: Artificial Sequence
```

<220> FEATURE:
<223> OTHER INFORMATION: Synthetic Construct

<400> SEQUENCE: 48
tataggatcc acacaggaaa cagaaatgag aattacaatt gccgg          45

<210> SEQ ID NO 49
<211> LENGTH: 36
<212> TYPE: DNA
<213> ORGANISM: Artificial Sequence
<220> FEATURE:
<223> OTHER INFORMATION: Synthetic Construct

<400> SEQUENCE: 49
cgcgcctgca ggttattttg cttttaataa ctcttc          36

<210> SEQ ID NO 50
<211> LENGTH: 30
<212> TYPE: DNA
<213> ORGANISM: Artificial Sequence
<220> FEATURE:
<223> OTHER INFORMATION: Synthetic Construct

<400> SEQUENCE: 50
tattggtacc tcaggttgga tcaacaggca          30

<210> SEQ ID NO 51
<211> LENGTH: 71
<212> TYPE: DNA
<213> ORGANISM: Artificial Sequence
<220> FEATURE:
<223> OTHER INFORMATION: Synthetic Construct

<400> SEQUENCE: 51
atagtgtcat atcatcatat taattgttct tttttcaggt gaaggttccc taggtgacac          60
tatagaacgc g          71

<210> SEQ ID NO 52
<211> LENGTH: 70
<212> TYPE: DNA
<213> ORGANISM: Artificial Sequence
<220> FEATURE:
<223> OTHER INFORMATION: Synthetic Construct

<400> SEQUENCE: 52
cggctggtga tttcgtccag cgaaccttcc atcgcatctt cgcccacggc tagtggatct          60
gatgggtacc          70

<210> SEQ ID NO 53
<211> LENGTH: 70
<212> TYPE: DNA
<213> ORGANISM: Artificial Sequence
<220> FEATURE:
<223> OTHER INFORMATION: Synthetic Construct

<400> SEQUENCE: 53
tttccgtctt tgtgtcaatg attgttgaca gaaaccttcc tgctatccaa atagtgtcat          60
atcatcatat          70

<210> SEQ ID NO 54
<211> LENGTH: 70
<212> TYPE: DNA
<213> ORGANISM: Artificial Sequence
<220> FEATURE:

<223> OTHER INFORMATION: Synthetic Construct

<400> SEQUENCE: 54
gcgtgctggg ataattgcga taaagctggg ttaataccga gcgttcaaaa cggctggtga    60
tttcgtccag                                                          70

<210> SEQ ID NO 55
<211> LENGTH: 70
<212> TYPE: DNA
<213> ORGANISM: Artificial Sequence
<220> FEATURE:
<223> OTHER INFORMATION: Synthetic Construct

<400> SEQUENCE: 55
tttctctccc atcccttccc cctccgtcag atgaactaaa cttgttaccg gacactatag    60
aacgcggccg                                                          70

<210> SEQ ID NO 56
<211> LENGTH: 70
<212> TYPE: DNA
<213> ORGANISM: Artificial Sequence
<220> FEATURE:
<223> OTHER INFORMATION: Synthetic Construct

<400> SEQUENCE: 56
gcgcagcata tacaggctga aacctttggc ctgttcgagt ttgatctgcg ccgcataggc    60
cactagtgga                                                          70

<210> SEQ ID NO 57
<211> LENGTH: 70
<212> TYPE: DNA
<213> ORGANISM: Artificial Sequence
<220> FEATURE:
<223> OTHER INFORMATION: Synthetic Construct

<400> SEQUENCE: 57
tatgcccgat gatattcctt tcatcgggct atttaaccgt tagtgcctcc tttctctccc    60
atcccttccc                                                          70

<210> SEQ ID NO 58
<211> LENGTH: 70
<212> TYPE: DNA
<213> ORGANISM: Artificial Sequence
<220> FEATURE:
<223> OTHER INFORMATION: Synthetic Construct

<400> SEQUENCE: 58
tttgttttcg ccagttcgat cacttcatca ccgcgtccgc tgatgattgc gcgcagcata    60
tacaggctga                                                          70

<210> SEQ ID NO 59
<211> LENGTH: 70
<212> TYPE: DNA
<213> ORGANISM: Artificial Sequence
<220> FEATURE:
<223> OTHER INFORMATION: Synthetic Construct

<400> SEQUENCE: 59
taccaaaggt gactggcaga atgaagtaaa cgtccgtgac ttcattcaga gacactatag    60
aacgcggccg                                                          70

-continued

```
<210> SEQ ID NO 60
<211> LENGTH: 70
<212> TYPE: DNA
<213> ORGANISM: Artificial Sequence
<220> FEATURE:
<223> OTHER INFORMATION: Synthetic Construct

<400> SEQUENCE: 60
gcgagttgaa acgtactgcg tagccagata cacggatggt cagctgcgga ccgcataggc    60
cactagtgga                                                          70

<210> SEQ ID NO 61
<211> LENGTH: 70
<212> TYPE: DNA
<213> ORGANISM: Artificial Sequence
<220> FEATURE:
<223> OTHER INFORMATION: Synthetic Construct

<400> SEQUENCE: 61
tgttacatgt ccgagcttaa tgaaaagtta gccacagcct gggaaggttt taccaaaggt    60
gactggcaga                                                          70

<210> SEQ ID NO 62
<211> LENGTH: 70
<212> TYPE: DNA
<213> ORGANISM: Artificial Sequence
<220> FEATURE:
<223> OTHER INFORMATION: Synthetic Construct

<400> SEQUENCE: 62
agattgagtg aaggtacgag taataacgtc ctgctgctgt tctttagtca gcgagttgaa    60
acgtactgcg                                                          70

<210> SEQ ID NO 63
<211> LENGTH: 70
<212> TYPE: DNA
<213> ORGANISM: Artificial Sequence
<220> FEATURE:
<223> OTHER INFORMATION: Synthetic Construct

<400> SEQUENCE: 63
tgaacttaac gcactcgtag agcgtgtaaa aaaagcccag cgtgaatatg gacactatag    60
aacgcggccg                                                          70

<210> SEQ ID NO 64
<211> LENGTH: 70
<212> TYPE: DNA
<213> ORGANISM: Artificial Sequence
<220> FEATURE:
<223> OTHER INFORMATION: Synthetic Construct

<400> SEQUENCE: 64
gcttttttct cagctttagc cggagcagct tctttcttcg ctgcagtttc ccgcataggc    60
cactagtgga                                                          70

<210> SEQ ID NO 65
<211> LENGTH: 72
<212> TYPE: DNA
<213> ORGANISM: Artificial Sequence
<220> FEATURE:
<223> OTHER INFORMATION: Synthetic Construct

<400> SEQUENCE: 65
```

```
aaaaaagttt aacattatca ggagagcatt atggctgtta ctaatgtcgc tgaacttaac    60
gcactcgtag ag                                                        72

<210> SEQ ID NO 66
<211> LENGTH: 72
<212> TYPE: DNA
<213> ORGANISM: Artificial Sequence
<220> FEATURE:
<223> OTHER INFORMATION: Synthetic Construct

<400> SEQUENCE: 66
aggggccgtt tatgttgcca gacagcgcta ctgattaagc ggattttttc gcttttttct    60
cagctttagc cg                                                        72

<210> SEQ ID NO 67
<211> LENGTH: 70
<212> TYPE: DNA
<213> ORGANISM: Artificial Sequence
<220> FEATURE:
<223> OTHER INFORMATION: Synthetic Construct

<400> SEQUENCE: 67
gcggaagcag ccaataagaa ggagaaggcg aatggctgag atgaaaaacc gacactatag    60
aacgcggccg                                                           70

<210> SEQ ID NO 68
<211> LENGTH: 71
<212> TYPE: DNA
<213> ORGANISM: Artificial Sequence
<220> FEATURE:
<223> OTHER INFORMATION: Synthetic Construct

<400> SEQUENCE: 68
gtgtttcaaa aagttgacgc ctacgctggc gacccgattc ttacgcttat taggtgacac    60
tatagaacgc g                                                         71

<210> SEQ ID NO 69
<211> LENGTH: 70
<212> TYPE: DNA
<213> ORGANISM: Artificial Sequence
<220> FEATURE:
<223> OTHER INFORMATION: Synthetic Construct

<400> SEQUENCE: 69
tggcaatggc gcgaatagcg taggcatcct cttccatacc ggcaccaaat tagtggatct    60
gatgggtacc                                                           70

<210> SEQ ID NO 70
<211> LENGTH: 70
<212> TYPE: DNA
<213> ORGANISM: Artificial Sequence
<220> FEATURE:
<223> OTHER INFORMATION: Synthetic Construct

<400> SEQUENCE: 70
ccggtttatt gtgttttaac cacctgcccg taaacctgga gaaccatcgc gtgtttcaaa    60
aagttgacgc                                                           70

<210> SEQ ID NO 71
<211> LENGTH: 70
<212> TYPE: DNA
<213> ORGANISM: Artificial Sequence
```

<220> FEATURE:
<223> OTHER INFORMATION: Synthetic Construct

<400> SEQUENCE: 71

```
ggagaaaatt ttcgagaacg aattgctcac cagagcgggt aatccagcgc tggcaatggc    60
gcgaatagcg                                                          70
```

<210> SEQ ID NO 72
<211> LENGTH: 71
<212> TYPE: DNA
<213> ORGANISM: Artificial Sequence
<220> FEATURE:
<223> OTHER INFORMATION: Synthetic Construct

<400> SEQUENCE: 72

```
atgtttgaga acattaccgc cgctcctgcc gacccgattc tgggcctggc taggtgacac    60
tatagaacgc g                                                        71
```

<210> SEQ ID NO 73
<211> LENGTH: 70
<212> TYPE: DNA
<213> ORGANISM: Artificial Sequence
<220> FEATURE:
<223> OTHER INFORMATION: Synthetic Construct

<400> SEQUENCE: 73

```
tagccgcgaa agcgcgcagt ccttcagcat cttcttccag accacgggca tagtggatct    60
gatgggtacc                                                          70
```

<210> SEQ ID NO 74
<211> LENGTH: 70
<212> TYPE: DNA
<213> ORGANISM: Artificial Sequence
<220> FEATURE:
<223> OTHER INFORMATION: Synthetic Construct

<400> SEQUENCE: 74

```
cgttaccctg atagcggact tcccttctgt aaccataatg gaacctcgtc atgtttgaga    60
acattaccgc                                                          70
```

<210> SEQ ID NO 75
<211> LENGTH: 70
<212> TYPE: DNA
<213> ORGANISM: Artificial Sequence
<220> FEATURE:
<223> OTHER INFORMATION: Synthetic Construct

<400> SEQUENCE: 75

```
caggccaaag tttttagagt aggaactggc aacaatcagc tctttatgca tagccgcgaa    60
agcgcgcagt                                                          70
```

<210> SEQ ID NO 76
<211> LENGTH: 30
<212> TYPE: DNA
<213> ORGANISM: Artificial Sequence
<220> FEATURE:
<223> OTHER INFORMATION: Synthetic Construct

<400> SEQUENCE: 76

```
tataggatcc cgggcaagta ccttgccgac                                    30
```

<210> SEQ ID NO 77

```
<211> LENGTH: 30
<212> TYPE: DNA
<213> ORGANISM: Artificial Sequence
<220> FEATURE:
<223> OTHER INFORMATION: Synthetic Construct

<400> SEQUENCE: 77
tatcaagctt tcagcccata tgcaggccgc                                        30

<210> SEQ ID NO 78
<211> LENGTH: 85
<212> TYPE: DNA
<213> ORGANISM: Artificial Sequence
<220> FEATURE:
<223> OTHER INFORMATION: Synthetic Construct

<400> SEQUENCE: 78
tattggtacc ttgacggcta gctcagtcct aggtacagtg ctagcgaatt cacaggaaac       60
agaccatgac tgacgttgtc atcgt                                             85

<210> SEQ ID NO 79
<211> LENGTH: 30
<212> TYPE: DNA
<213> ORGANISM: Artificial Sequence
<220> FEATURE:
<223> OTHER INFORMATION: Synthetic Construct

<400> SEQUENCE: 79
tattggatcc tcagcccata tgcaggccgc                                        30

<210> SEQ ID NO 80
<211> LENGTH: 85
<212> TYPE: DNA
<213> ORGANISM: Artificial Sequence
<220> FEATURE:
<223> OTHER INFORMATION: Synthetic Construct

<400> SEQUENCE: 80
tattggtacc tttacggcta gctcagtcct aggtactatg ctagcgaatt cacaggaaac       60
agaccatgac tgacgttgtc atcgt                                             85

<210> SEQ ID NO 81
<211> LENGTH: 85
<212> TYPE: DNA
<213> ORGANISM: Artificial Sequence
<220> FEATURE:
<223> OTHER INFORMATION: Synthetic Construct

<400> SEQUENCE: 81
tattggtacc tttatggcta gctcagtcct aggtacaatg ctagcgaatt cacaggaaac       60
agaccatgac tgacgttgtc atcgt                                             85

<210> SEQ ID NO 82
<211> LENGTH: 85
<212> TYPE: DNA
<213> ORGANISM: Artificial Sequence
<220> FEATURE:
<223> OTHER INFORMATION: Synthetic Construct

<400> SEQUENCE: 82
tattggtacc tttacagcta gctcagtcct agggactgtg ctagcgaatt cacaggaaac       60
agaccatgac tgacgttgtc atcgt                                             85
```

```
<210> SEQ ID NO 83
<211> LENGTH: 85
<212> TYPE: DNA
<213> ORGANISM: Artificial Sequence
<220> FEATURE:
<223> OTHER INFORMATION: Synthetic Construct

<400> SEQUENCE: 83
tattggtacc ctgatagcta gctcagtcct agggattatg ctagcgaatt cacaggaaac    60
agaccatgac tgacgttgtc atcgt                                          85

<210> SEQ ID NO 84
<211> LENGTH: 70
<212> TYPE: DNA
<213> ORGANISM: Artificial Sequence
<220> FEATURE:
<223> OTHER INFORMATION: Synthetic Construct

<400> SEQUENCE: 84
acaggtgaac gagtcctttg gctttgagct ggaattttt gactttctgc gacactatag     60
aacgcggccg                                                           70

<210> SEQ ID NO 85
<211> LENGTH: 70
<212> TYPE: DNA
<213> ORGANISM: Artificial Sequence
<220> FEATURE:
<223> OTHER INFORMATION: Synthetic Construct

<400> SEQUENCE: 85
ttgcttaagt tttgcagcgt agtctgagaa atactggtca gagcttctgc ccgcataggc    60
cactagtgga                                                           70

<210> SEQ ID NO 86
<211> LENGTH: 70
<212> TYPE: DNA
<213> ORGANISM: Artificial Sequence
<220> FEATURE:
<223> OTHER INFORMATION: Synthetic Construct

<400> SEQUENCE: 86
atgaaactcg ccgtttatag cacaaaacag tacgacaaga agtacctgca acaggtgaac    60
gagtcctttg                                                           70

<210> SEQ ID NO 87
<211> LENGTH: 70
<212> TYPE: DNA
<213> ORGANISM: Artificial Sequence
<220> FEATURE:
<223> OTHER INFORMATION: Synthetic Construct

<400> SEQUENCE: 87
agcggcaaga ttaaaccagt tcgttcgggc aggtttcgcc tttttccaga ttgcttaagt    60
tttgcagcgt                                                           70

<210> SEQ ID NO 88
<211> LENGTH: 77
<212> TYPE: DNA
<213> ORGANISM: Artificial Sequence
<220> FEATURE:
<223> OTHER INFORMATION: Synthetic Construct

<400> SEQUENCE: 88
```

```
ttgcttaagt tttgcagcgt agtctgagaa atactggtca gagcttctgc tgagcggata        60
catatttgaa tgtattt                                                      77

<210> SEQ ID NO 89
<211> LENGTH: 35
<212> TYPE: DNA
<213> ORGANISM: Artificial Sequence
<220> FEATURE:
<223> OTHER INFORMATION: Synthetic Construct

<400> SEQUENCE: 89
ttgacggcta gctcagtcct aggtacagtg ctagc                                  35

<210> SEQ ID NO 90
<211> LENGTH: 35
<212> TYPE: DNA
<213> ORGANISM: Artificial Sequence
<220> FEATURE:
<223> OTHER INFORMATION: Synthetic Construct

<400> SEQUENCE: 90
tttacggcta gctcagtcct aggtactatg ctagc                                  35

<210> SEQ ID NO 91
<211> LENGTH: 35
<212> TYPE: DNA
<213> ORGANISM: Artificial Sequence
<220> FEATURE:
<223> OTHER INFORMATION: Synthetic Construct

<400> SEQUENCE: 91
tttatggcta gctcagtcct aggtacaatg ctagc                                  35

<210> SEQ ID NO 92
<211> LENGTH: 35
<212> TYPE: DNA
<213> ORGANISM: Artificial Sequence
<220> FEATURE:
<223> OTHER INFORMATION: Synthetic Construct

<400> SEQUENCE: 92
tttacagcta gctcagtcct agggactgtg ctagc                                  35

<210> SEQ ID NO 93
<211> LENGTH: 35
<212> TYPE: DNA
<213> ORGANISM: Artificial Sequence
<220> FEATURE:
<223> OTHER INFORMATION: Synthetic Construct

<400> SEQUENCE: 93
ctgatagcta gctcagtcct agggattatg ctagc                                  35
```

RECOMBINANT MICROORGANISM FOR PRODUCING POLYHYDROXYALKANOATE

CROSS-REFERENCE TO RELATED APPLICATIONS

This application is a U.S. national phase under the provisions of 35 U.S.C. § 371 of International Patent Application No. PCT/KR18/02305 filed Feb. 26, 2018, which in turn claims priority of Korean Patent Application No. 10-2017-0026266 filed Feb. 28, 2017 and priority of Korean Patent Application No. 10-2017-017-2899 filed Dec. 15, 2017. The disclosures of such international patent application and Korean priority patent applications are hereby incorporated herein by reference in their respective entireties, for all purposes.

TECHNICAL FIELD

The present invention relates to a method for producing polyhydroxyalkanoate having an aromatic monomer or a long-chain 2-hydroxyalkanoate (2-HA) monomer. More particularly, the present invention relates to a recombinant microorganism which is introduced with a gene encoding a 2-hydroxyisocaproate-CoA transferase and a gene encoding polyhydroxyalkanoate synthase and is capable of producing polyhydroxyalkanoate having an aromatic monomer or a long-chain 2-hydroxyalkanoate (2-HA) monomer, and a method for producing polyhydroxyalkanoate having an aromatic monomer or a long-chain 2-HA monomer using the recombinant microorganism.

BACKGROUND ART

Polyhydroxyalkanoates (PHAs) are biological polyesters synthesized by a variety of microorganisms. These polymers are biodegradable and biocompatible thermoplastic materials, can be utilized in a variety of industrial biomedical applications because the properties thereof are similar to petroleum-based polymers, and are produced from renewable sources (Lee, S. Y. *Biotechnol. Bioeng.* 49:1 1996).

PHAs are classified into short-chain-length PHAs having a short carbon number and medium-chain-length PHAs having a long carbon number depending on the length of the side chain.

Various PHAs have been synthesized through recombinant microorganisms produced by cloning PHA synthetic genes derived from microorganisms such as *Ralstonia eutropha, Pseudomonas* and *Bacillus* (Qi et al., *FEMS Microbiol. Lett.,* 157:155, 1997; Qi et al., *FEMS Microbiol. Lett.,* 167:89, 1998; Langenbach et al., *FEMS Microbiol. Lett.,* 150:303, 1997; WO 01/55436; U.S. Pat. No. 6,143,952; WO 98/54329; WO 99/61624).

PHAs having short side chains such as PHBs, which are homopolymers of R-3-hydroxy butyric acid, are thermoplastic materials of crystals and are readily broken due to the low elasticity thereof. On the other hand, MCL-PHAs with long side chains have higher elasticity. PHBs first became known about 70 years ago (Lemoigne & Roukhelman, 1925). On the other hand, MCL-PHAs relatively recently became known (deSmet et al., *J. Bacteriol.* 154:870-78 1983). These copolymers can be represented by poly(3HB-co-3-HX), wherein X represents 3-hydroxyalkanoate, or alkanoate or alkenoate having 6 or more carbon atoms. A particular example of a copolymer of two particular monomers is poly(3HB-co-3-hydroxyhexanoate) (Brandl et al., Int. J. Biol. Macromol. 11:49, 1989; Amos & McInerney, Arch. Microbiol., 155:103, 1991; U.S. Pat. No. 5,292,860).

The biosynthesis of PHAs includes converting hydroxyl acid into hydroxyacyl-CoA through CoA-transferase or CoA-ligase and polymerizing the converted hydroxyacyl-CoA using a PHA synthase. In the case of natural PHA synthase, the activity for 2-hydroxyacyl-CoA is much lower than the activity for 3-hydroxyacyl-CoA. However, recently, the present inventors have developed a genetically engineered PHA synthase (PhaC1ps6-19) of *Pseudomonas* sp. 6-19 so as to use lactyl-CoA, which is a kind of 2-hydroxyacyl-CoA, as a substrate (WO 08/062996; Yang et al., *Biotechnol. Bioeng.,* 105:150, 2010; Jung et al., *Biotechnol. Bioeng.,* 105:161, 2010). PhaC1ps6-19 has a wide variety of substrate specificities, and can use lactyl-CoA, which is one kind of 2-hydroxyacyl-CoA, as a substrate. Thus, synthesis of new PHAs containing different types of 2-hydroxy acids will be made possible by developing a system for converting various kinds of 2-hydroxy acid into 2-hydroxyacyl-CoA.

Accordingly, the present inventors have made intensive efforts to develop a novel method for biosynthesizing PHAs containing 2-hydroxy acid. As a result, the present inventors have found that, when screening an enzyme that converts 2-hydroxy acid into 2-hydroxyacyl-CoA using acetyl-CoA and using the enzyme, various kinds of 2-hydroxyacyl-CoA can be produced under in vitro conditions and various PHAs can be produced using the same. Based on this finding, the present invention has been completed.

DISCLOSURE

Technical Problem

Therefore, it is one object of the present invention to provide a recombinant microorganism capable of producing polyhydroxyalkanoate having an aromatic monomer or a long-chain 2-hydroxyalkanoate (2-HA) monomer.

It is another object of the present invention to provide a method for producing polyhydroxyalkanoate having an aromatic monomer or a long-chain 2-HA monomer using the recombinant microorganism.

Technical Solution

In accordance with one aspect of the present invention, provided is a recombinant microorganism obtained by introducing a gene encoding a 2-hydroxyisocaproate-CoA transferase and a gene encoding polyhydroxyalkanoate synthase into a microorganism capable of producing acetyl-CoA from a carbon source, wherein the recombinant microorganism is capable of producing polyhydroxyalkanoate having an aromatic monomer or a long-chain 2-hydroxyalkanoate (2-HA) monomer.

In accordance with another aspect of the present invention, provided is a method for producing polyhydroxyalkanoate having an aromatic monomer or a long-chain 2-hydroxyalkanoate (2-HA) monomer including (a) culturing the recombinant microorganism to produce polyhydroxyalkanoate having an aromatic monomer or a long-chain 2-hydroxyalkanoate (2-HA) monomer; and (b) recovering the produced polyhydroxyalkanoate having an aromatic monomer or a long-chain 2-hydroxyalkanoate (2-HA) monomer.

In accordance with another aspect of the present invention, provided is a recombinant microorganism obtained by amplifying a gene encoding a 2-hydroxyisocaproate-CoA transferase, a gene encoding a polyhydroxyalkanoate synthase, a gene encoding a 3-deoxy-D-arabino-heptulosonate- 7-phosphate (DAHP) synthase, a gene encoding a chorismate mutase/prephenate dehydrogenase, and a gene encoding a D-lactate dehydrogenase in a microorganism capable of producing acetyl-CoA from a carbon source, wherein the recombinant microorganism is capable of producing polyhydroxyalkanoate having phenyllactate as a monomer.

In accordance with another aspect of the present invention, provided is a method for producing polyhydroxyalkanoate having phenyllactate as a monomer including: (a) culturing the recombinant microorganism to produce polyhydroxyalkanoate having phenyllactate as a monomer; and (b) recovering the produced polyhydroxyalkanoate having phenyllactate as a monomer.

In accordance with another aspect of the present invention, provided is a recombinant microorganism obtained by amplifying a gene encoding a 2-hydroxyisocaproate-CoA transferase, a gene encoding a polyhydroxyalkanoate synthase, a gene encoding a 3-deoxy-D-arabino-heptulosonate-7-phosphate (DAHP) synthase, a gene encoding a chorismate mutase/prephenate dehydrogenase, a gene encoding a D-lactate dehydrogenase, a gene encoding a hydroxymandelate synthase, a gene encoding a hydroxymandelate oxidase, and a gene encoding a D-mandelate dehydrogenase in a microorganism capable of producing acetyl-CoA from a carbon source, wherein the recombinant microorganism is capable of producing polyhydroxyalkanoate having mandelate as a monomer.

In accordance with another aspect of the present invention, provided is a method for producing polyhydroxyalkanoate having mandelate as a monomer including: (a) culturing the recombinant microorganism to produce polyhydroxyalkanoate having mandelate as a monomer; and (b) recovering the produced polyhydroxyalkanoate having mandelate as a monomer.

DESCRIPTION OF DRAWINGS

The patent or application file contains at least one drawing executed in color. Copies of this patent or patent application publication with color drawing(s) will be provided by the Office upon request and payment of the necessary fee.

Reference will now be made in detail to the preferred embodiments of the present invention, examples of which are illustrated in the accompanying drawings. Wherever possible, the same reference numbers will be used throughout the drawings to refer to the same or like parts.

FIG. 2 shows the results of comparison of amino acid sequence homology between HadA (SEQ ID NO: 1) and FldA (ATCC 3502);

BEST MODE

Figure 1:
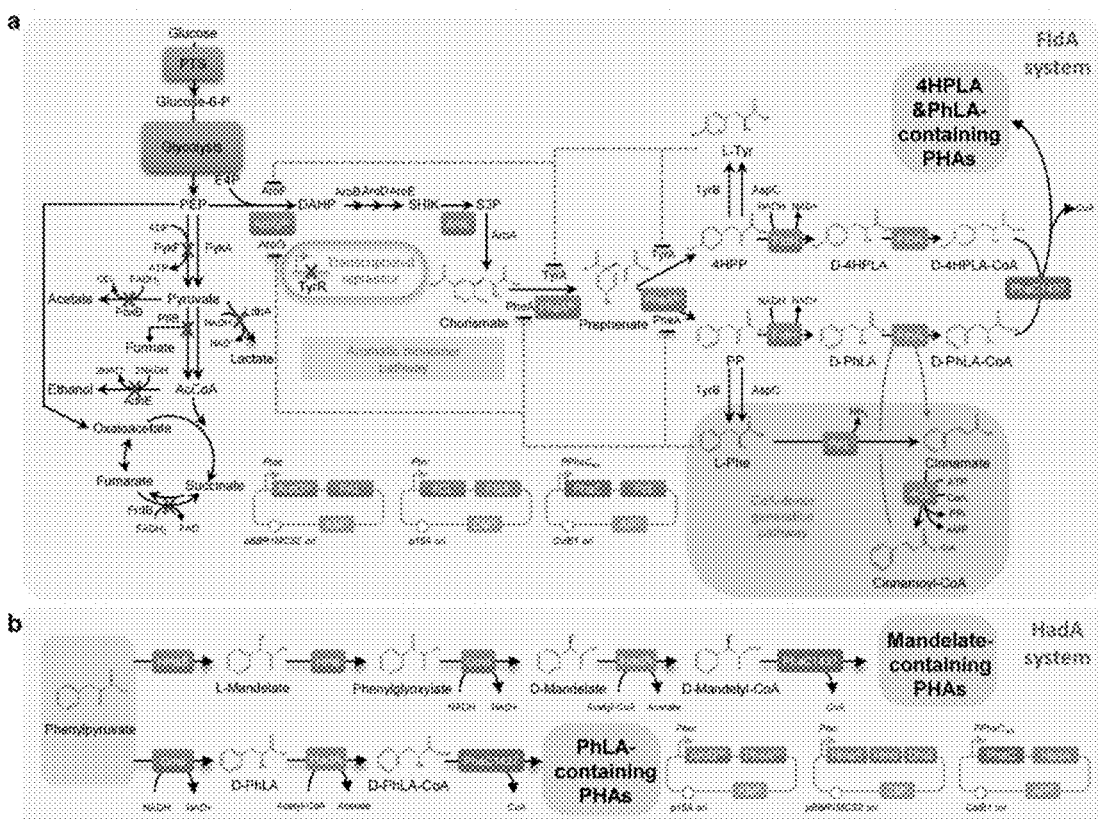
FIG. 1 shows the biosynthesis metabolic pathway of the aromatic polyester according to the present invention, wherein diagram a shows a metabolic pathway when FldA (cinnamoyl-CoA:phenyllactate CoA-transferase) is used, and diagram b shows a metabolic pathway when HadA (2-hydroxyisocaproate-CoA transferase) is used.

Unless defined otherwise, all technical and scientific terms used herein have the same meanings as appreciated by those skilled in the field to which the present invention pertains. In general, the nomenclature used herein is well-known in the art and is ordinarily used.

Aromatic polyesters are essential plastics which are mainly produced from petroleum. The present invention establishes a method of producing a polymer having aromatic polyester or long-chain 2-hydroxyalkanoate as a monomer from glucose in one step through metabolically engineered E. coli expressing a polyhydroxyalkanoate (PHA) synthase and coenzyme A (CoA) transferases that are active toward aromatic monomer.

In one embodiment of the present invention, in order to produce PHA containing phenyllactate as an aromatic polyester, cinnamoyl-CoA:phenyllactate CoA-transferase (FldA) and 4-coumarate:CoA ligase (4CL), which were found to have activity through in vitro analysis, were expressed together with a PHA synthase in the D-phenyllactate-producing E. coli strain. The strain prepared a poly (16.8 mol % D-lactate-co-80.8 mol % 3HB-co-1.6 mol % D-phenyllactate-co-0.8 mol % D-4-hydroxyphenyllactate) polymer in an amount of 12.8 wt % of the dry cell weight using in-vivo-produced cinnamoyl-CoA as a CoA donor.

However, since the utilization range of aromatic substrate of the phenyllactate CoA-transferase (FldA) is very narrow, 2-isocaprenoyl-CoA:2-hydroxyisocaproate CoA-transferase (HadA) that can produce a variety of kinds of aromatic hydroxyacyl CoA using acetyl-CoA as a CoA donor was identified, selected and used for the production of aromatic PHA. In order to mass-produce aromatic PHAs containing a high mole fraction of D-phenyllactate, an optimal metabolic pathway was first designed to over-produce the D-phenyllactate monomer.

In one embodiment of the present invention, in order to produce a metabolically engineered *E. coli* having a metabolic pathway optimal for the production of D-phenyllactate, the feedback-resistant aroG, pheA and fldH genes in tyrR-deficient *E. coli* were overexpressed, the competitive metabolic pathways (pflB, poxB, adhE and frdB) were deleted, and the tyrB and aspC genes were further deleted according to in-silico genomic scale metabolic flux analysis. The metabolically engineered *E. coli* produced 1.62 g/L of D-phenyllactate. When HadA and PHA synthases were expressed in the D-phenyllactate-overproducing strain, poly (52.1 mol % 3HB-co-47.9 mol % D-phenyllactate) was produced in an amount of 15.8 wt % of the dry cell weight. Also, the potential of preparing various aromatic polyesters was confirmed by preparing polyesters including 4-hydroxyphenyllactate, mandelate and 3-hydroxy-3-phenylpropionate.

Therefore, in one aspect, the present invention is directed to a recombinant microorganism obtained by introducing a gene encoding a 2-hydroxyisocaproate-CoA transferase and a gene encoding polyhydroxyalkanoate synthase into a microorganism capable of producing acetyl-CoA from a carbon source, wherein the recombinant microorganism is capable of producing polyhydroxyalkanoate having an aromatic monomer or a long-chain 2-hydroxyalkanoate (2-HA) monomer.

In the present invention, long-chain 2-HA means 2-hydroxyalkanoate having 6 to 8 carbon atoms.

In the present invention, the aromatic monomer or long chain 2-HA monomer is selected from the group consisting of 2-hydroxyisocaproate, 2-hydroxyhexanoate, 2-hydroxyoctanoate, phenyllactate, 2-hydroxy-4-phenylbutyrate, 3-hydroxy-3-phenylpropionate, 4-hydroxybenzoic acid and mandelate.

In the present invention, the polyhydroxyalkanoate synthase is a PHA synthase derived from a strain selected from the group consisting of *Ralstonia eutropha*, *Pseudomonas*, *Bacillus* and *Pseudomonas* sp. 6-19, or a mutant enzyme of a PHA synthase having an amino acid sequence selected from the following:

an amino acid sequence having at least one mutation selected from the group consisting of E130D, S325T, L412M, S477R, S477H, S477F, S477Y, S477G, Q481M, Q481K and Q481R in the amino acid sequence of SEQ ID NO: 2;

an amino acid sequence (C1335) having mutations of E130D, S325T, L412M, S477G and Q481M in the amino acid sequence of SEQ ID NO: 2;

an amino acid sequence (C1310) having mutations of E130D, S477F and Q481K in the amino acid sequence of SEQ ID NO: 2; and an amino acid sequence (C1312) having mutations of E130D, S477F and Q481R in the amino acid sequence of SEQ ID NO: 2.

In the present invention, the 2-hydroxyisocaproate-CoA transferase may be hadA derived from *Clostridium difficile* 630.

In the present invention, the 2-hydroxyisocaproate-CoA transferase may use acetyl-CoA as a CoA donor.

The microorganism of the present invention may be further introduced with a gene encoding a β-ketothiolase involved in 3-hydroxybutyryl-CoA biosynthesis and a gene encoding an acetoacetyl-CoA reductase in order for the microorganism to produce a polymer even without the supply of 3HB from the outside.

In another aspect, the present invention is directed to a method for producing polyhydroxyalkanoate having an aromatic monomer or a long-chain 2-hydroxyalkanoate (2-HA) monomer including: (a) culturing the recombinant microorganism to produce polyhydroxyalkanoate having an aromatic monomer or a long-chain 2-hydroxyalkanoate (2-HA) monomer; and (b) recovering the produced polyhydroxyalkanoate having an aromatic monomer or a long-chain 2-hydroxyalkanoate (2-HA) monomer.

In one embodiment of the present invention, it was confirmed whether or not Pct (propionyl-CoA transferase) used for the synthesis of polyhydroxyalkanoate is capable of activating phenyllactate and mandelate with phenyllactyl-CoA and mandelyl-CoA, respectively. The mutant of Pctcp (Pct540) has been successfully applied to the in-vivo production of polyesters including various hydroxy acids such as glycolic acid, lactic acid, 2-hydroxybutyric acid, 2-hydroxyisovalerate and 2-hydroxy acid. For this reason, it can be considered that Pct540 has a broad substrate spectrum with respect to the carbon number and the hydroxyl group position. However, it has been confirmed that Pct540 does not have catalytic activity for phenyllactate and mandelate. Thus, in the present invention, an attempt was made to find a novel CoA-transferase capable of activating CoA derivatives corresponding to aromatic compounds for the production of aromatic copolymers.

The cinnamoyl-CoA:phenyllactate CoA-transferase (FldA) of *Clostridium sporogenes* has been reported to be able to convert phenyllactate into phenyllactyl-CoA using cinnamoyl-CoA as a CoA donor (Dickert, S. et al., Eur. J. Biochem. 267: 3874, 2000). Since cinnamoyl-CoA is a non-natural metabolite of *E. coli*, FldA derived from *Clostridium botulinum* A str. ATCC 3502, which has 99.0% homology with FldA of *C. sporogenes*, was tested in order to confirm whether or not acetyl-CoA, which is a metabolite abundant in cells, is used as a CoA donor. However, FldA of *C. botulinum* A str. ATCC 3502 was found to have no catalytic activity to produce phenyllactyl-CoA using acetyl-CoA as a CoA donor.

Meanwhile, it is known that *Streptomyces coelicolor* 4-coumarate:CoA ligase (4CL) plays a key role in the metabolism of phenylpropanoids which produce precursors of secondary metabolites of plants such as lignin, flavonoids and phytoalexins (Kaneko, M. et al., J. Bacteriol., 185:20, 2003). Therefore, in one embodiment of the present invention, a biosynthetic pathway for synthesizing cinnamoyl-CoA from cinnamate was designed by introducing 4CL. 4CL mutants were used to convert cinnamate into cinnamoyl-CoA, and cinnamoyl-CoA was used as a CoA donor for FldA to form phenyllactyl-CoA. As a result, phenyllactyl-CoA was successfully synthesized through successive in-vitro reactions of 4CL and FldA. These results demonstrated that 4CL and FldA could be used for the production of phenyllactyl-CoA and the production of aromatic polyesters. Similarly, it could be confirmed that another promising aromatic monomer, 4-hydroxyphenyllactate, was also converted into 4-hydroxyphenyllactyl-CoA by successive in-vitro reactions of 4CL variants with FldA.

In the production of non-natural polyesters, it is important to select mutants of the PHA synthase for polymerization of the corresponding CoA substrate. Therefore, in order to investigate the performance of various PHA synthases, *Pseudomonas* sp. MBEL 6-19 PHA synthase (PhaCPs6-19) mutants were expressed in *E. coli* XL1-Blue overexpressing AroGfbr, PAL, 4CL, FldA and Pct540. The prepared recombinant strains were cultured in a MR medium supplemented with 20 g/L of glucose, 1 g/L of D-phenyllactate and 1 g/L of sodium 3-hydroxybutyrate (3HB). Sodium 3-hydroxybutyrate (3HB) was converted through Pct540 into 3HB-CoA, which is a preferred substrate of PhaC, and was added to enhance the production of the polymer since it allowed the production of sufficient amounts of PHAs. *E. coli* XL1-Blue expressing other PHA synthase mutants can produce various amounts of poly(D-lactate-co-3HB-co-D-phenyllactate) having different monomer compositions.

As a result of the above experiment, among the PhaC mutants, PhaC1437 having four amino acid substitutions (E130D, S325T, S477G and Q481K) produced poly(18.3 mol % D-lactate-co-76.9 mol % 3HB-co-4.8 mol % D-phenyllactate) in an amount of 7.8% by weight of dry cell weight, which means that PhaC1437 is the most suitable PhaC mutant.

Next, *E. coli* was engineered in vivo to produce D-phenyllactate from glucose. The biosynthesis of aromatic compounds begins with the synthesis of 3-deoxy-D-arabino-heptulosonate-7-phosphate (DAHP), which is produced by condensation between phosphoenolpyruvate (PEP) and erythrose-4-phosphate (E4P) by DAHP synthase. The produced DAHP is converted into phenylpyruvate (PPA) which is then converted into D-phenyllactate by D-lactate dehydrogenase (FldH) (FIG. 1). The metabolic pathway for aromatic compound biosynthesis is known to be controlled in a complicated manner through various inhibiting mechanisms. The expression of the DAHP synthase encoded by aroG and the chorismate mutase/prephenate dehydrogenase encoded by pheA is inhibited by L-phenylalanine (Ribe, D. E. et al., J. Bacteriol. 127:1085, 1976).

In the present invention, feedback-inhibiting resistant mutants, AroGfbr [AroG (D146N)] and PheAfbr [PheA (T326P)], were constructed to release feedback inhibition by L-phenylalanine (Zhou, H. Y. et al., Bioresour. Technol. 101:4151, 2010; Kikuchi, Y. et al., Appl. Environ. Microbiol. 63:761, 1997). *E. coli* XL1-Blue expressing AroGfbr, PheAfbr and FldH of *C. botulinum* A str. ATCC 3502 produced 0.372 g/L of D-phenyllactate from 15.2 g/L of glucose. The overexpression of PAL, 4CL, FldA, Pct540 and PhaC1437 of the strain increased poly(16.8 mol % D-lactate-co-80.8 mol % 3HB-co-1.6 mol % D-phenyllactate-co-0.8 mol % D-4-hydroxyphenyllactate) to 12.8 wt % of the dry cell weight. There are two problems in producing an aromatic PHA containing D-phenyllactate. The first problem is that the efficiency of polymer synthesis and the content of aromatic monomer are very low. This is considered to be due to inefficiency of FldA using cinnamoyl-CoA as a CoA donor. The second problem is that the monomer spectrum of aromatic PHA is very narrow. The results of in vitro enzymatic analysis showed that FldA can transfer CoA to phenyllactate and 4-hydroxyphenyllactate, but cannot transfer the same to substrates such as mandelate, 2-hydroxy-4-phenylbutyrate, 3-hydroxy-3-phenylpropionate and 4-hydroxybenzoic acid.

In order to solve these problems, the present invention uses acetyl-CoA as a CoA donor to find an enzyme having a broad aromatic substrate spectrum. Sequence similarity analysis was performed to identify homologous enzymes for FldA, and 2-isocaprenoyl-CoA:2-hydroxyisocapronate CoA-transferase (HadA) of *Clostridium difficile* having an amino acid sequence identity of 48% or more with FldA among various FldAs having different origins was screened (FIG. 2). In the present invention, it has been investigated whether or not HadA can use acetyl-CoA as a CoA donor, since HadA is an enzyme known to convert CoA into 2-hydroxyisocaproate using isocaprenoyl-CoA as a CoA donor (FIG. 3). Interestingly, the results of in vitro enzyme analysis showed that HadA can activate phenyllactate into phenyllactyl-CoA using acetyl-CoA as a CoA donor (FIG. 4).

In addition, LC-MS analysis after in vitro assays showed that HadA can convert mandelate, 4-hydroxymandelate, phenyllactate, 4-hydroxyphenyllactate, 2-hydroxy-4-phenylbutyrate, 3-hydroxy-3-phenylpropionate and 4-hydroxybenzoic acid to the corresponding CoA derivatives (FIGS. 4 and 5). Therefore, HadA has the potential to more efficiently produce various aromatic polyesters using acetyl-CoA as a CoA donor.

Next, in order to increase the production amount of aromatic monomers by metabolic engineering, the yield was increased by metabolically engineering an *E. coli* XL1-Blue strain expressing AroGfbr, PheAfbr and FldH producing a small amount (0.372 g/L) of D-phenyllactate from glucose. The *E. coli* XBT strain expressing AroGfbr, PheAfbr and FldH, which deleted TyrR, which is a double transcriptional regulatory factor that performs regulation to inhibit aromatic amino acid biosynthesis, was constructed and the *E. coli* XBT strain produced 0.5 g/L of D-phenyllactate from 16.4 g/L of glucose and thus showed 30% higher productivity than the *E. coli* XL1-Blue strain which did not delete TyrR. In order to remove the pathway competing with D-phenyllactate biosynthesis, *E. coli* XB201T was constructed by deleting poxB (a gene encoding a pyruvate oxidase), pflB (a gene encoding a pyruvate formate lyase), adhE (a gene encoding an acetaldehyde dehydrogenase/alcohol dehydrogenase) and frdB (a gene encoding a fumarate reductase) from *E. coli* XBT. The *E. coli* strain XB201T expressing AroGfbr, PheAfbr and FldH produced 0.55 g/L of D-phenyllactate from 15.7 g/L of glucose, which indicates a yield 10% higher than that of *E. coli* XBT.

In addition, metabolic engineering analysis according to in-silico genome scale metabolism flux analysis was performed to further increase the production of D-phenyllactate (FIG. 6). A tyrB gene encoding a tyrosine aminotransferase and an aspC gene encoding an aspartic acid aminotransferase were removed from the *E. coli* strain XB201T to reduce the L-phenylalanine biosynthesis and thereby enhance the carbon flow to D-phenyllactate. As a result, *E. coli* strain XB201TBA expressing AroGfbr, PheAfbr and FldH produced 1.62 g/L of D-phenyllactate from 18.5 g/L of glucose, resulting in a great increase in yield, which corresponds to 4.35 times higher than the D-phenyllactate production of the *E. coli* XL1 blue strain.

When *E. coli* XB201TBAL expressing AroGfbr, PheAfbr, FldH, PhaC1437 and HadA were cultured in a medium containing 20 g/L glucose and 1 g/L sodium 3HB, poly(52.1 mol % 3HB-co-47.9 mol % D-phenyllactate) was produced in an amount of 15.8 wt % of the dry cell weight (FIG. 7).

In another aspect, the present invention is directed to a recombinant microorganism obtained by introducing a gene encoding a 2-hydroxyisocaproate-CoA transferase, a gene encoding a polyhydroxyalkanoate synthase, a gene encoding a DAHP (3-deoxy-D-arabino-heptulosonate-7-phosphate) synthase, a gene encoding a chorismate mutase/prephenate dehydrogenase, and a gene encoding a D-lactate dehydrogenase into a microorganism capable of producing acetyl-CoA from a carbon source, wherein the recombinant microorganism is capable of producing polyhydroxyalkanoate having phenyllactate as a monomer.

In the present invention, the 2-hydroxyisocaproate-CoA transferase may be HadA derived from *Clostridium difficile* 630 and the polyhydroxyalkanoate synthase is a PHA synthase derived from a strain selected from the group consisting of *Ralstonia eutropha, Pseudomonas, Bacillus* and

*Pseudomonas* sp. 6-19, or a mutant enzyme of a PHA synthase having an amino acid sequence selected from the following:

an amino acid sequence having at least one mutation selected from the group consisting of E130D, S325T, L412M, S477R, S477H, S477F, S477Y, S477G, Q481M, Q481K and Q481R in an amino acid sequence of SEQ ID NO: 2;

an amino acid sequence (C1335) having mutations of E130D, S325T, L412M, S477G and Q481M in the amino acid sequence of SEQ ID NO: 2;

an amino acid sequence (C1310) having mutations of E130D, S477F and Q481K in the amino acid sequence of SEQ ID NO: 2; and an amino acid sequence (C1312) having mutations of E130D, S477F and Q481R in the amino acid sequence of SEQ ID NO: 2.

In the present invention, the gene encoding the DAHP (3-deoxy-D-arabino-heptulosonate-7-phosphate) synthase is a gene encoding the amino acid sequence represented by SEQ ID NO: 8, the gene encoding chorismate mutase/prephenate dehydrogenase may be a gene encoding the amino acid sequence represented by SEQ ID NO: 9, and the gene encoding D-lactate dehydrogenase may be a gene encoding the amino acid sequence represented by SEQ ID NO: 10.

In the present invention, the introduced gene encoding D-lactate dehydrogenase may be a fldH gene which replaces the ldhA gene.

The microorganism of the present invention may be further introduced with a gene encoding a β-ketothiolase and a gene encoding an acetoacetyl-CoA reductase involved in 3-hydroxybutyryl-CoA biosynthesis in order for the microorganism to produce a polymer even without external supply of sodium 3HB.

When the expression amounts of the gene (phaA) encoding a β-ketothiolase and the gene (phaB) encoding an acetoacetyl-CoA reductase, which are introduced in the present invention, are regulated through the strength (intensity) of the promoter, the mole fraction of the D-phenyllactate monomer contained in PHA can be controlled.

Figure 9:
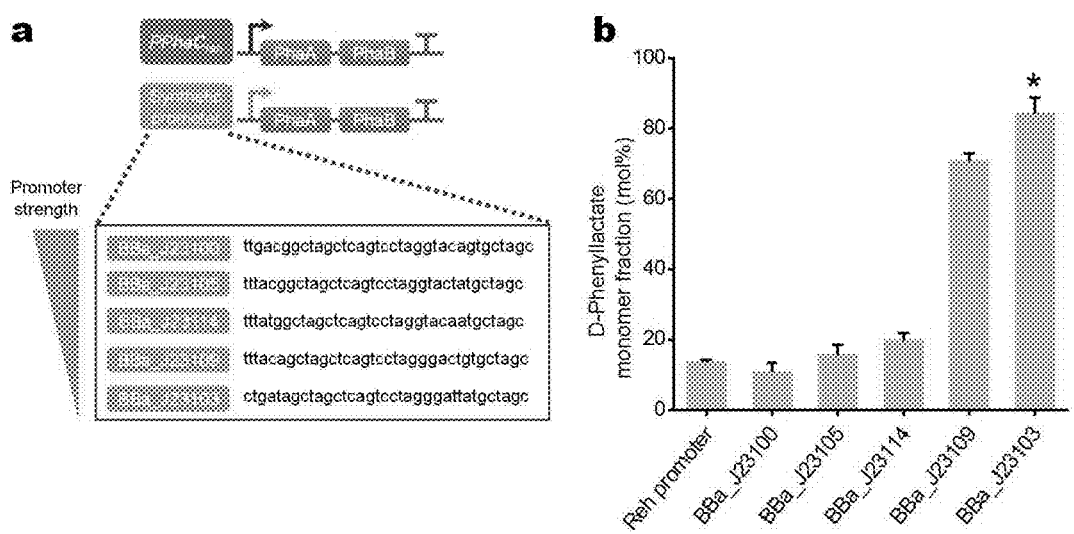
FIG. 9 shows the results of production of poly(3HB-co-D-phenyllactate) in an E. coli XB201TBAL strain expressing PhaAB under five types of promoters having different strengths.

In one embodiment of the present invention, five different plasmids which express phaA and phaB with five types of promoters having different strengths were constructed and introduced into XB201TBAL strains expressing AroGfbr, PheAfbr, FldH, PhaC1437 and HadA. It was confirmed that, as phaA and phaB expression decreased, the mole fraction of the phenyllactate monomer increased (FIG. 9, showing in diagram a the synthetic promoters BBa_J23100 (SEQ ID NO: 89), BBa_J23105 (SEQ ID NO: 90), BBa_J23114 (SEQ ID NO: 91), BBa_J23109 (SEQ ID NO: 92), and BBa_J23103 (SEQ ID NO: 93), and showing in graph b the D-phenyllactate monomer fraction (mole percent) for such promoters; and Table 7). These results suggest that aromatic polyesters having various mole fractions of aromatic monomers can be produced by controlling the metabolic flux.

In the present invention, the recombinant microorganism has a deletion of at least one gene selected from the group consisting of a tyrR gene, a gene encoding a pyruvate oxidase, a gene encoding a pyruvate formate lyase, a gene encoding an acetaldehyde dehydrogenase, a gene encoding a fumarate reductase, a gene encoding a tyrosine aminotransferase, and a gene encoding an aspartic acid aminotransferase.

In another aspect, the present invention is directed to a method for producing polyhydroxyalkanoate having phenyllactate as a monomer including: (a) culturing the recombinant microorganism to produce polyhydroxyalkanoate having phenyllactate as a monomer; and (b) recovering the produced polyhydroxyalkanoate having phenyllactate as a monomer.

Figure 8:
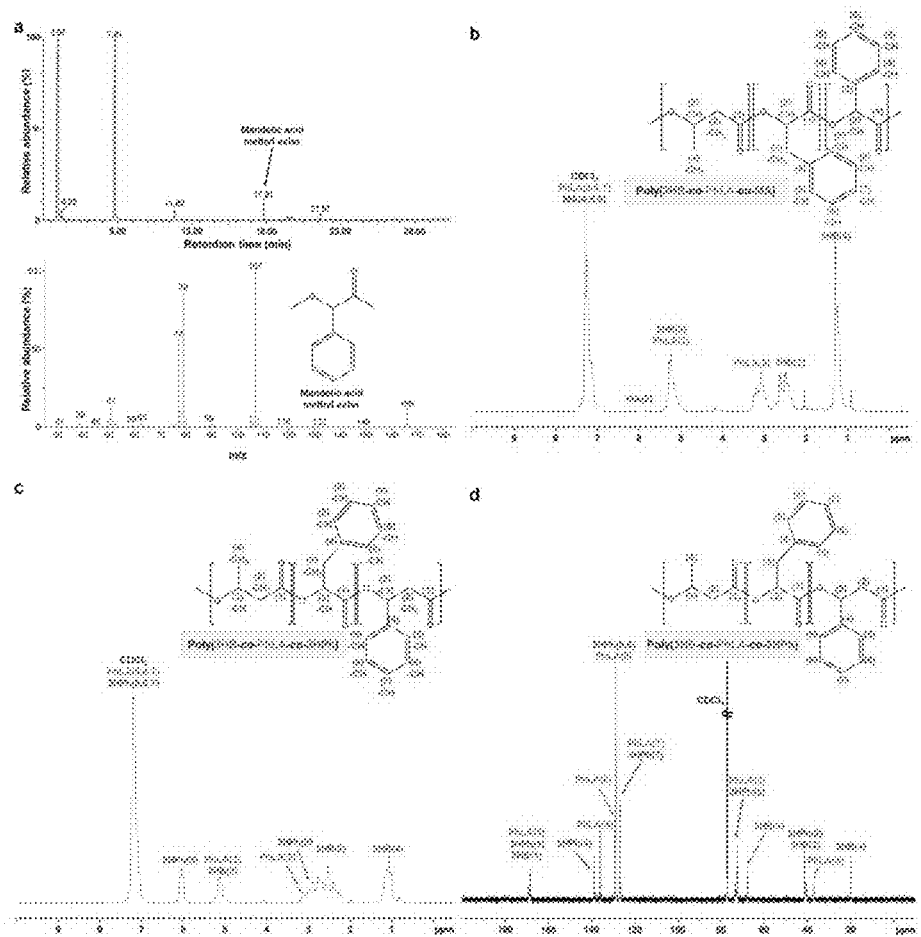
FIG. 8 shows the results of analysis of poly(3HB-co-D-phenyllactate-co-3-hydroxy-3-phenylpropionate) and poly(3HB-co-D-phenyllactate-co-D-mandelate) produced by E. coli XB201TBAL.

In order to identify whether or not the method described above can be used for the preparation of various aromatic polymers, experimentation was conducted using mandelate as a monomer. The reason for this is that polymandelate, which is a homopolymer of mandelate, is a pyrolysis-resistant polymer having a relatively high Tg of 100° C., and has properties similar to those of polystyrene. Polymandelate is chemically synthesized through ring-opening polymerization of a cyclic dimer of mandelate produced in the petroleum industry. When *E. coli* XB201TBAL expressing AroGfbr, PheAfbr, FldH, PhaC1437 and HadA was cultured in a medium containing 1 g/L of sodium 3HB and 0.5 g/L of D-mandelate, poly(55.2 mol % 3HB-co-43 mol % D-phenyllactate-co-1.8 mol % D-mandelate) was produced in an amount of 11.6 wt % of the dry cell weight (FIG. 8 in spectra a and b). In the present invention, an aromatic copolymer containing D-mandelate was successfully prepared using D-mandelate as a substrate, and then D-mandelate was prepared in vivo by metabolic engineering. A hydroxymandelate synthase (HmaS) derived from *Amycolatopsis orientalis*, a hydroxymandelate oxidase (Hmo) of *S. coelicolor* and a D-mandelate dehydrogenase (Dmd) of *Rhodotorula graminis* were expressed in *E. coli* XB201TBAL expressing AroGfbr, PheAfbr, FldH, PhaC1437 and HadA in order to produce an aromatic copolymer containing D-mandelate from glucose. When the engineered strains were cultured in a medium containing 20 g/L of glucose and 1 g/L of sodium 3HB, poly(92.9 mol % of 3HB-co-6.3 mol % D-phenyllactate-co-0.8 mol % D-mandelate) was prepared in an amount of 16.4 wt % of the dry cell weight.

In another aspect, the present invention is directed to a recombinant microorganism obtained by introducing a gene encoding a 2-hydroxyisocaproate-CoA transferase, a gene encoding a polyhydroxyalkanoate synthase, a gene encoding a DAHP (3-deoxy-D-arabino-heptuloonate-7-phosphate) synthase, a gene encoding a chorismate mutase/prephenate dehydrogenase, a gene encoding a D-lactate dehydrogenase, a gene encoding a hydroxymandelate synthase, a gene encoding a hydroxymandelate oxidase, and a gene encoding a D-mandelate dehydrogenase into a microorganism capable of producing acetyl-CoA from a carbon source, wherein the recombinant microorganism is capable of producing polyhydroxyalkanoate having mandelate as a monomer.

In the present invention, the 2-hydroxyisocaproate-CoA transferase may be hadA derived from *Clostridium difficile* 630 and the polyhydroxyalkanoate synthase may be a PHA synthase derived from a strain selected from the group consisting of *Ralstonia eutropha, Pseudomonas, Bacillus* and *Pseudomonas* sp. 6-19, or a mutant enzyme of a PHA synthase having an amino acid sequence selected from the following:

an amino acid sequence having at least one mutation selected from the group consisting of E130D, S325T, L412M, S477R, S477H, S477F, S477Y, S477G, Q481M, Q481K and Q481R in an amino acid sequence of SEQ ID NO: 2;

an amino acid sequence (C1335) having mutations of E130D, S325T, L412M, S477G and Q481M in the amino acid sequence of SEQ ID NO: 2;

an amino acid sequence (C1310) having mutations of E130D, S477F and Q481K in the amino acid sequence of SEQ ID NO: 2; and an amino acid sequence (C1312) having mutations of E130D, S477F and Q481R in the amino acid sequence of SEQ ID NO: 2.

In the present invention, the gene encoding the DAHP (3-deoxy-D-arabino-heptulosonate-7-phosphate) synthase may be a gene encoding the amino acid sequence represented by SEQ ID NO: 8, the gene encoding chorismate mutase/prephenate dehydrogenase may be a gene encoding the amino acid sequence represented by SEQ ID NO: 9, and the gene encoding D-lactate dehydrogenase may be a gene encoding the amino acid sequence represented by SEQ ID NO: 10.

In the present invention, the gene encoding hydroxymandelate synthase may be a gene encoding the amino acid sequence represented by SEQ ID NO: 11, the gene encoding hydroxymandelate oxidase may be a gene encoding the amino acid sequence represented by SEQ ID NO: 12, and the gene encoding D-mandelate dehydrogenase may be a gene encoding the amino acid sequence represented by SEQ ID NO: 13.

The microorganism of the present invention may be further introduced with genes encoding a β-ketothiolase and a gene encoding an acetoacetyl-CoA reductase involved in 3-hydroxybutyryl-CoA biosynthesis in order for the microorganism to produce a polymer even without the external supplementation of sodium 3HB.

In another aspect, the present invention is directed to a method for producing polyhydroxyalkanoate having mandelate as a monomer including: (a) culturing the recombinant microorganism to produce polyhydroxyalkanoate having mandelate as a monomer; and (b) recovering the produced polyhydroxyalkanoate having mandelate as a monomer.

Further, in the present invention, in order to confirm the possibility of the production of polyhydroxyalkanoate containing various long-chain 2-HA using the recombinant strain of the present invention, polymer productivity was identified using long-chain 2-HA monomers such as 2-hydroxyisocaproate (2HIC), 2-hydroxyhexanoate (2HH) and 2-hydroxyoctanoate (2HO) as monomers. As a result, it was identified that copolymers containing 2-hydroxyisocaproate, 2-hydroxyhexanoate or 2-hydroxyoctanoate were produced and that, as the concentration of 2-HA contained in the medium increased, the mole fraction of the monomer contained in the copolymer increased (Tables 4, 5 and 6).

Accordingly, in another aspect, the present invention is directed to a method for producing polyhydroxyalkanoate having, as a monomer, a compound selected from the group consisting of 2-hydroxyisocaproate, 2-hydroxyhexanoate and 2-hydroxyoctanoate, including: (a) culturing the recombinant microorganism capable of producing polyhydroxyalkanoate having an aromatic monomer or a long-chain 2-HA monomer in a medium containing a compound selected from the group consisting of 2-hydroxyisocaproate, 2-hydroxyhexanoate and 2-hydroxyoctanoate; and (b) recovering polyhydroxyalkanoate containing, as a monomer, a compound selected from the group consisting of 2-hydroxyisocaproate, 2-hydroxyhexanoate and 2-hydroxyoctanoate.

In the present invention, production of an aromatic polymer was identified using 3-hydroxy-3-phenylpropionate (3HPh) as another aromatic monomer capable of producing PHA. When the E. coli strain XB201TBA was cultured in a medium containing 20 g/L of glucose, 0.5 g/L of 3-hydroxy-3-phenylpropionic acid and 1 g/L of sodium 3HB, poly(33.3 mol % 3HB-co-18 mol % D-phenyllactate-co-48.7 mol % 3HPh) was produced in an amount of 14.7 wt % of dry cell weight (FIG. 8 in spectra c and d FIGS. 8C and 8D). These results suggest that the HadA and the mutated PHA synthases developed in the present invention can be widely used for the production of various aromatic polyesters.

Finally, the physical properties of aromatic PHAs produced by metabolically engineered E. coli were investigated. The poly(52.1 mol % 3HB-co-47.9 mol % D-phenyllactate) was amorphous, and, as the mole fraction of D-phenyllactate in the copolymer increased, the Tg increased significantly to 23.86° C., although the molecular weight was decreased. Also, the copolymer containing an aromatic compound in the polymer had decreased crystallinity. It is considered that the aromatic ring of the polymer interferes with the crystallization of P(3HB). P(3HB) has high brittleness due to the strong crystallinity thereof, whereas the resulting copolymer has improved mechanical toughness due to decreased crystallinity and increased Tg.

In the present invention, a bacterial platform system was developed for the production of various aromatic polyesters. The aromatic polymer production system of the present invention identified a novel CoA-transferase having a wide range of substrates for activating an aromatic compound into a CoA derivative thereof and established PHA synthase mutants capable of polymerizing aromatic CoA derivatives thereof and a pathway to over-produce aromatic monomers in vivo through the design and optimization of metabolisms.

As evidenced using several aromatic monomers in various embodiments of the present invention, such a system can be used in the preparation of various aromatic polymers. For example, according to the present invention, HadA (or related enzymes) and PHA synthases can be engineered to accommodate the desired aromatic monomers. The bacterial platform system developed in the present invention can contribute to establishment of a bioprocess for the production of aromatic polyesters from renewable non-food biomass.

As used herein, the term "vector" means a DNA product containing a DNA sequence operably linked to a control sequence capable of expressing DNA in a suitable host. The vector may be a plasmid, a phage particle or a simple potential genome insert. Once the vector is transformed with an appropriate host, it may replicate and function independently of the genome of the host, or may often be integrated with the genome itself. Since the plasmid is the most commonly used type of vector, the terms "plasmid" and "vector" are sometimes used interchangeably throughout the specification of the present invention. For the purpose of the present invention, a plasmid vector is preferably used. A typical plasmid vector that can be used for this purpose includes (a) a replication origin to efficiently conduct replication so as to include several to several hundred plasmid vectors per host cell, (b) an antibiotic resistance gene to screen a host cell transformed with the plasmid vector, and (c) a restriction enzyme cleavage site into which a foreign DNA fragment is inserted. Even if an appropriate restriction enzyme cleavage site is not present, the vector and foreign DNA can be easily ligated using a synthetic oligonucleotide adapter or a linker according to a conventional method.

After ligation, the vector should be transformed into an appropriate host cell. In the present invention, the preferred host cells are prokaryotic cells. Suitable prokaryotic host cells include E. coli DH5a, E. coli JM101, E. coli K12, E. coli W3110, E. coli X1776, E. coli XL-1 Blue (Stratagene), E. coli B, E. coli B21 and the like. However, E. coli strains such as FMB101, NM522, NM538 and NM539, as well as the species and genera of other prokaryotes, and the like, can also be used. In addition to the E. coli mentioned above, the genus Agrobacterium strains such as Agrobacterium A4,

*Bacillus* strains such as *Bacillus subtilis*, other enterobacteria such as *Salmonella typhimurium* or *Serratia marcescens*, and various *Pseudomonas* genus strains can be used as host cells.

Transformation of prokaryotic cells can be easily carried out using a calcium chloride method described in the section 1.82 of Sambrook et al., supra. Alternatively, electroporation (Neumann, et al., EMBO J., 1: 841, 1982) can be used for transformation of these cells.

The vector used for overexpression of the gene according to the present invention may be any expression vector known in the art and is preferably a pET-based vector (Novagen). When cloning is performed using the pET-based vector, histidine groups are bonded to the ends of the expressed protein, so that the protein can be effectively purified. The expressed protein can be isolated from the cloned gene through a general method known in the art and can be specifically isolated using a chromatographic method using Ni-NTA His-conjugated resin (Novagen). In the present invention, the recombinant vector may be pET-SLTI66, and the host cell may be *E. coli* or *Agrobacterium*.

As used herein, the term "expression control sequence" means a DNA sequence essential for the expression of a coding sequence operably linked to a particular host organism. Such a control sequence includes promoters for conducting transcription, any operator sequences for controlling such transcription, sequences for encoding suitable mRNA ribosome-binding sites, and sequences for controlling the termination of transcription and translation. For example, control sequences suitable for prokaryotes include promoters, optionally operator sequences and ribosome binding sites. Eukaryotic cells include promoters, polyadenylation signals and enhancers. The factor that has the greatest impact on the expression level of the gene in the plasmid is a promoter. SRα promoters, cytomegalovirus-derived promoters and the like are preferably used as promoters for high expression. Any of a wide variety of expression control sequences may be used for the vector in order to express the DNA sequences of the present invention. Useful expression control sequences include, for example, the early and late promoters of SV40 or adenovirus, the lac system, the trp system, the TAC or TRC system, T3 and T7 promoters, the major operator and promoter regions of phage lambda, control regions of fd code proteins, promoters of 3-phosphoglycerate kinase or other glycol lyases, promoters of the phosphatase, such as Pho5, promoters of yeast alpha-mating systems and other sequences known to control gene expression of prokaryotic or eukaryotic cells or viruses and various combinations thereof. The T7 promoter may be useful for expressing proteins of the present invention in *E. coli*.

When a nucleic acid sequence is aligned with another nucleic acid sequence based on a functional relationship, it is "operably linked" thereto. This may be gene(s) and control sequence(s) linked in such a way so as to enable gene expression when a suitable molecule (e.g., a transcriptional activator protein) is linked to the control sequence(s). For example, DNA for a pre-sequence or secretory leader is operably linked to DNA for a polypeptide, when expressed as a pre-protein involved in the secretion of the polypeptide; and a promoter or enhancer is operably linked to a coding sequence when it affects the transcription of the sequence; or a ribosome-binding site is operably linked to a coding sequence when it affects the transcription of the sequence; or the ribosome-binding site is operably linked to a coding sequence when positioned to facilitate translation. Generally, "operably linked" means that the linked DNA sequence is in contact therewith, or that a secretory leader is in contact therewith and is present in the reading frame. However, the enhancer need not be in contact therewith. The linkage of these sequences is carried out by ligation (linkage) at convenient restriction enzyme sites. When no such site exists, a synthetic oligonucleotide adapter or a linker according to a conventional method is used.

As used herein, the term "expression vector" commonly refers to a recombinant carrier, into which a fragment of heterologous DNA is inserted, and generally means a fragment of double-stranded DNA. Herein, the heterologous DNA means exogenous DNA that is not naturally found in the host cell. Once an expression vector is present in a host cell, it can replicate independently of the host chromosomal DNA, and several copies of the vector and inserted (heterologous) DNA thereof can be produced.

As is well known in the art, in order to increase the expression level of a transgene in a host cell, the gene should be operably linked to a transcriptional/translational expression control sequence that functions in a selected expression host. Preferably, the expression control sequence and the corresponding gene are included in one recombinant vector containing both a bacterial selection marker and a replication origin. When the host cell is a eukaryotic cell, the recombinant vector should further include a useful expression marker in the eukaryotic expression host.

The host cell transfected or transformed by the recombinant vector described above constitutes another aspect of the present invention. As used herein, the term "transfection" means introducing DNA into a host and making the DNA replicable by an extrachromosomal factor or chromosomal integration. As used herein, the term "transformation" means that an expression vector is accommodated by the host cell, regardless of whether or not any coding sequence is actually expressed.

It should be understood that not all vectors function identically in expressing the DNA sequences of the present invention. Likewise, not all hosts function identically for the same expression system. However, those skilled in the art will be able to make appropriate selections from among a variety of vectors, expression control sequences and hosts without excessive burden of experimentation and without departing from the scope of the present invention. For example, selection of a vector should be carried out in consideration of a host because the vector should be replicated therein. The number of replications of the vector, the ability to control the number of replications, and the expression of other proteins encoded by the corresponding vector, such as the expression of antibiotic markers, should also be considered. In selecting the expression control sequence, a number of factors should be considered. For example, the relative strength of the sequence, controllability, and compatibility with the DNA sequences of the present invention should be considered, particularly in relation to possible secondary structures. The single cell host may be selected in consideration of factors such as the selected vector, the toxicity of the product encoded by the DNA sequence of the present invention, secretion characteristics, the ability to accurately fold proteins, culture and fermentation factors, and ease of purification of the product encoded by the DNA sequence according to the present invention. Within the scope of these factors, those skilled in the art can select various vector/expression control sequences/host combinations capable of expressing the DNA sequences of the present invention in fermentation or large animal cultures. As a screening method for cloning the cDNA of the protein according to the present invention through expression cloning, a binding method, a panning method, a film emulsion method or the like can be applied.

Hereinafter, the present invention will be described in more detail with reference to the following examples. However, it will be obvious to those skilled in the art that the following examples are provided only for illustration of the present invention and should not be construed as limiting the scope of the present invention.

In the following examples, *Escherichia coli* was used as a recombinant microorganism. However, any microorganism can be used without limitation so long as it is capable of producing acetyl-CoA from a carbon source. Examples of the microorganism include the genera *Alcaligenes*, *Pseudomonas*, *Escherichia*, *Ralstonia*, *Bacillus* and *Corynebacterium* and the like.

The recombinant strains, plasmids and primers used or produced in the present invention are shown in Tables 1 to 3.

TABLE 1

| Strain name | Characteristics | Origin |
|---|---|---|
| XL1-Blue | recA1 endA1 gyrA96 thi-1 hsdR17 supE44 relA1 lac [F' proAB lacI$^q$ZΔM15 Tn10 (Tet$^R$)] | Stratagene[a] |
| BL21(DE3) | BL21(DE3) F-ompT hsdSB (rB-mB-) gal dcm (DE3) | Invitrogen[b] |
| XBT | XL1-Blue ΔtyrR | the present invention |
| XB201T | XL1-Blue ΔtyrR ΔpoxB ΔpflB ΔadhE ΔfrdB | the present invention |
| XB201TB | XL1-Blue ΔtyrR ΔpoxB ΔpflB ΔadhE ΔfrdB ΔtyrB | the present invention |
| XB201TBA | XL1-Blue ΔtyrR ΔpoxB ΔpflB ΔadhE ΔfrdB ΔtyrB ΔaspC | the present invention |
| XB201TBAL | XL1-Blue ΔtyrR ΔpoxB ΔpflB ΔadhE ΔfrdB ΔtyrB ΔaspC ΔldhA | the present invention |
| XB201TBAF | XL1-Blue ΔtyrR ΔpoxB ΔpflB ΔadhE ΔfrdB ΔtyrB ΔaspC ΔldhA::Ptrc-fldH-rrnBT | the present invention |

TABLE 2

| Plasmid | Characteristics Abbreviations: Ap, ampicillin; Km, kanamycin; Cm, chloramphenicol; $^R$, resistance. | Origin |
|---|---|---|
| pKD46 | λ-Red recombinase under arabinose inducible araBAD promoter, temperature sensitive origin; Ap$^R$ | 1 |
| pJW168 | lox66-cat-lox71 cassette; Cm$^R$Ap$^R$ | 2 |
| pMloxC | Cre-recombinase under IPTG inducible lacUV5 promoter, temperature sensitive origin; Ap$^R$ | 3 |
| pMtrc9 | pMloxC derivative; trc promoter downstream of lox66-cat-lox71 cassette; Ap$^R$ | |
| pKM212-MCS | pBBR1MCS2 derivative; promoter, PHA biosynthesis genes transcription terminator; Km$^R$ | 4 |
| pET-22b(+) | Expression vector, T7 promoter; Ap$^R$ | Novagen[c] |
| pPs619C1437Pct540 | pBluescript II KS(+) derivative; *Ralstonia eutropha* PHA biosynthesis operon promoter, *Pseudomonas* sp. MBEL 6-19 phaC$_{Ps6-19}$ variant (phaC1437; E130D, S325T, S477G, Q481K), *Clostridium propionicum* pct$_{Cp}$variant (pct540; V193A, silent mutations: T78C, T669C, A1125G, T1158C), transcriptional terminator of the *R. eutropha* PHA biosynthesis operon; Ap$^R$ | 5 |
| pPs619C1wtPct540 | pPs619C1437Pct540 derivative; phaC1437 was replaced by phaC1$_{Ps6-19}$wild type; Ap$^R$ | 6 |
| pPs619C1202Pct540 | pPs619C1437Pct540 derivative; phaC1437 was replaced by phaC1202 (E130D, Q481K); Ap$^R$ | 5 |
| pPs619C1301Pct540 | pPs619C1437Pct540 derivative; phaC1437 was replaced by phaC1301 (E130D, S325T, Q481K); Ap$^R$ | 5 |
| pPs619C1310Pct540 | pPs619C1437Pct540 derivative; phaC1437 was replaced by phaC1310 (E130D, S477F, Q481K); Ap$^R$ | 5 |
| pPs619C1439Pct540 | pPs619C1437Pct540 derivative; phaC1437 was replaced by phaC1439 (E130D, S325T, S477F, Q481K); Ap$^R$ | 5 |
| pCnCAB | pBluescript II KS(+) derivative; *R. eutropha* PHA biosynthesis operon promoter, *R. eutropha* phaCAB genes, transcriptional terminator of the *R. eutropha* PHA biosynthesis operon, Ap$^R$ | 5 |
| pCnAB | pCnCAB derivative; *R. eutropha* PHA biosynthesis operon promoter, *R. eutropha* phaAB; Ap$^R$ | 7 |
| pPs619C1437-HadA | pBluescript II KS(+) derivative; *R. eutropha* PHA biosynthesis operon promoter, *Pseudomonas* sp. MBEL 6-19 phaC$_{Ps6-19}$variant (phaC1437; E130D, S325T, S477G, Q481K), *Clostridium difficile* hadA gene, transcriptional terminator of the *R. eutropha* PHA biosynthesis operon; Ap$^R$ | The present invention |
| pET22b-hisPCT540 | pET22b(+) derivative; T7 promoter, the *C. propionicum* pct540 gene; Ap$^R$ | The present invention |
| pET22b-his4CL | pET22b(+) derivative; promoter, the *S. coelicolor* gene; Ap$^R$ | The present invention |
| pET22b-his4CL(A294G) | pET22b(+) derivative; promoter, the *S. coelicolor* (A294G) gene; Ap$^R$ | The present invention |
| pET22b-hisFldA | pET22b(+) derivative; promoter, the *C. botulinum* A str. ATCC 3502 fldA gene; Ap$^R$ | The present invention |

TABLE 2-continued

| Plasmid | Characteristics Abbreviations: Ap, ampicillin; Km, kanamycin; Cm, chloramphenicol; $^R$, resistance. | Origin |
| --- | --- | --- |
| pKM212-AroG$^{fbr}$ | pKM212-MCS derivative; tac promoter, the E. coli feedback resistant aroG(D146N) gene; Km$^R$ | The present invention |
| pKM212-AroG$^{fbr}$PAL | pKM212-MCSderivative; tac promoter, the E. coli feedback resistant aroG(D146N) and Streptomyces maritimus PAL genes; Km$^R$ | The present invention |
| pKM212-AroG$^{fbr}$PheA$^{fbr}$ | pKM212-MCS derivative; tac promoter, the E. coli feedback resistant aroG(D146N) and pheA(T326P) genes; Km$^R$ | The present invention |
| pKM212-GPE-PhaAB | pKM212-MCS derivative; tac promoter, the E. coli feedback resistant aroG(D146N), pheA(T326P), R. eutropha PHA biosynthesis operon promoter, R. eutropha phaA and phaB genes; Km$^R$ | The present invention |
| pKM212-GPE-100PhaAB | pKM212-MCS derivative; tac promoter, the E. coli feedback resistant aroG(D146N), pheA(T326P), BBa_J23100 promoter, R. eutropha phaA and phaB genes; Km$^R$ | The present invention |
| pKM212-GPE-105PhaAB | pKM212-MCS derivative; tac promoter, the E. coli feedback resistant aroG(D146N), pheA(T326P), BBa_J23105 promoter, R. eutropha phaA and phaB genes; Km$^R$ | The present invention |
| pKM212-GPE-114PhaAB | pKM212-MCS derivative; tac promoter, the E. coli feedback resistant aroG(D146N), pheA(T326P), BBa_J23114 promoter, R. eutropha phaA and phaB genes; Km$^R$ | The present invention |
| pKM212-GPE-109PhaAB | pKM212-MCS derivative; tac promoter, the E. coli feedback resistant aroG(D146N), pheA(T326P), BBa_J23109 promoter, R. eutropha phaA and phaB genes; Km$^R$ | The present invention |
| pKM212-GPE-103PhaAB | pKM212-MCS derivative; tac promoter, the E. coli feedback resistant aroG(D146N), pheA(T326P), BBa_J23103 promoter, R. eutropha phaA and phaB genes; Km$^R$ | The present invention |
| pTrc-FldH | pTrc99A derivative; trc promoter, the C. botulinum A str. ATCC 3502 fldH gene; Ap$^R$ | The present invention |
| pACYC184KS | pACYC184 derivative; MCS of pBluescript II KS in XbaI and NaeI site of pACYC184; Cm$^R$ | Patent |
| pACYC-FldH | pACYC184KS derivative; trc promoter, the C. botulinum A str. ATCC 3502 fldH gene; Cm$^R$ | The present invention |
| pACYC-4CL(A294G) | pACYC184KS derivative; trc promoter, the S. coelicolor (A294G) gene; Cm$^R$ | The present invention |
| pACYC-4CL(A294G)FldA | pACYC184KS derivative; trc promoter, the S. coelicolor (A294G) and the C. botulinum A str. ATCC 3502 fldA genes; Cm$^R$ | The present invention |
| pACYC-4CL(A294G)FldAH | pACYC184KS derivative; trc promoter, the S. coelicolor (A294G), and the C. botulinum A str. ATCC 3502 fldA and fldH genes; Cm$^R$ | The present invention |
| pET22b-hisHadA | pET22b(+) derivative; promoter, the C. difficile A str. ATCC hadA genes; Ap$^R$ | The present invention |
| pKM212-HmaS | pKM212-MCS derivative; tac promoter, the Amycolatopsis orientalis hmaS gene; Km$^R$ | The present invention |
| pKM212-HmaSHmo | pKM212-MCS derivative; tac promoter, the A. orientalis hmaS and S. coelicolor hmo genes; Km$^R$ | The present invention |
| pKM212-HmaSHmoDmd | pKM212-MCS derivative; tac promoter, the A. orientalis hmaS and S. coelicolor hmo and Rhodotorula graminis dmd genes; Km$^R$ | The present invention |
| pKA312-MCS | pKA32-MCS derivative; tac promoter, R. eutropha PHA biosynthesis genes transcription terminator; Cm$^R$ | 7 |
| pKA312-PanE | pKA312-MCS derivative; tac promoter, Lactococcus lactis subsp. lactis Il1403 panE gene; Cm$^R$ | 7 |
| pKA312-AroG$^{fbr}$PheA$^{fbr}$ | pKA312-MCS derivative; tac promoter, the E. coli feedback resistant aroG(D146N) and pheA(T326P) genes; Cm$^R$ | The present invention |
| pMtrcFldH | pMtrc9 derivative; trc promoter, the C. botulinum A str. ATCC 3502 fldH gene; Ap$^R$ | The present invention |

1 Datsenko, K. A. & Wanner, B. P Natl Acad Sci USA 97:6640, 2000.
2 Lee, K. H. et al., Molecular Systems Biology 3, doi:ARTN 149 10.1038/msb4100196, 2007.
3 Palmeros, B. et al. Gene 247:255, 2000.
4 Park, S. J. et al., Metab Eng 20, 20, 2013.
5 Yang, T. H. et al. Biotechnol Bioeng 105:150, 2010.
6 Yang, T. H. et al., Appl Microbiol Biotechnol 90:603, 2011.
7 Choi, S. Y. et al., Nat Biotechnol 34:435, 2016.
8 Knobloch, K. H. & Hahlbrock, K., Archives of Biochemistry and Biophysics 184: 237, 1977.
9 Kaneko, M. et al., J Bacteriol 185:20, 2003.

TABLE 3

| Primer | Sequence | SEQ ID NO |
|---|---|---|
| Pcthis-F | CGCG<u>CATATG</u>AGAAAGGTTCCCATTATTAC | 14 |
| Pcthis-R | CGCG<u>GGATCC</u>TTAGTGATGGTGATGGTGGGACTTCATTTCCTTCAGAC | 15 |
| 4CLhis-F | TACA<u>GAATTC</u>ATGTTCCGCAGCGAGTACGC | 16 |
| 4CLhis-R | TATT<u>CCTGCAGG</u>TTAGTGATGGTGATGGTGGTGTCGCGGCTCCCTGAGCTGTC | 17 |
| 4CLmut-F | TACATCGTCAGCGGCGCC | 18 |
| 4CLmut-R | GGCGCCGCTGACGATGTA | 19 |
| FldAhis-F | CGCG<u>CATATG</u>GAAAACAATGCAAACATGTT | 20 |
| FldAhis-R | CGCG<u>AAGCTT</u>TTAGTGATGGTGATGGTGGTGTTTTTCTTTGCGAACCATGATA | 21 |
| AroG-F | CGCG<u>GAATTC</u>ATGAATTATCAGAACGACGA | 22 |
| AroG-R | TATT<u>AAGCTT</u>TTACCCGCGACGCGCTTTTA | 23 |
| PheA-F | TATC<u>AAGCTT</u>ACACAGGAAACAGAAATGACATCGGAAAACCCGTT | 24 |
| PheA-R | CGCG<u>AAGCTT</u>TCAGGTTGGATCAACAGGCA | 25 |
| PheAmut-F | ACAATCTGATTATGCCCCGTCTGGAATCAC | 26 |
| PheAmut-R | GTGATTCCAGACGGGGCATAATCAGATTGT | 27 |
| PAL-Kp-F | TATA<u>GGTACC</u>ACACAGGAAACAGAAATGGGGACCTTCGTTATTGA | 28 |
| PAL-Sal-R | CGCT<u>GTCGAC</u>TTATCACTTGTCATCGTCAT | 29 |
| FldH-F | TATA<u>GGATCC</u>ATGAAAATCCTGGCGTATTGCG | 30 |
| FldH-R | CGCG<u>AAGCTT</u>TTATTTACAAACGCGCTGGT | 31 |
| Trc-F | CGCG<u>CTCGAG</u>GCTGTTGACAATTAATCATC | 32 |
| Ter-R | CGCG<u>GAGCTC</u>TGTAGAAACGCAAAAAGGCC | 33 |
| FldA-F | TATA<u>CCTGCAGG</u>ACACAGGAAACAGAAATGGAAAACAATGCAAACAT | 34 |
| FldA-R | TATG<u>CCTGCAGG</u>TTAGTGATGGTGATGGTGGT | 35 |
| FldH-sbF | TATA<u>CCTGCAGG</u>ACACAGGAAACAGAAATGAAAATCCTGGCGTATTGCG | 36 |
| FldH-hiR | CGCG<u>AAGCTT</u>TATTTACAAACGCGCTGGT | 37 |
| HadA-hisF | CGGC<u>CATATG</u>CTTTTAGAAGGAGTTAAAGT | 38 |
| HadA-hisR | TATT<u>GCGGCCGC</u>TTAGTGATGGTGATGGTGGTGATATCTTACAACTTTACTAT | 39 |
| HadA-sbF | TATT<u>CCTGCAGG</u>CGGATAACAATTTCACACAGGAAACAGAATTCATGCTTTTAGAAGGAGTTAA | 40 |
| HadA-ndR | CGCG<u>CATATG</u>TTAATATCTTACAACTTTAC | 41 |
| HadA-sbmR | TATT<u>CCTGCAGG</u>ACACAGGAAACAGAAATGCTTTTAGAAGGAGTTAA | 42 |
| HadA-sbmR | TATA<u>CCTGCAGG</u>TTAATATCTTACAACTTTAC | 43 |
| Hmo-F | TATA<u>GGTACC</u>ACACAGGAAACAGAAATGCGGGAACCACTCACGCT | 44 |
| Hmo-R | TATA<u>GGATCC</u>TTATCCATGGCTCCTATCTCGGT | 45 |
| Dmd-F | TATA<u>GGATCC</u>ACACAGGAAACAGAAATGCCTCGTCCGCGCGTCCT | 46 |
| Dmd-R | TATG<u>CCTGCAGG</u>TTATGCAGCAGATGACGGCGCAAA | 47 |
| PanE-F | TATA<u>GGATCC</u>ACACAGGAAACAGAAATGAGAATTACAATTGCCGG | 48 |
| PanE-R | CGCG<u>CCTGCAGG</u>TTATTTTGCTTTTAATAACTCTTC | 59 |
| PheA-kpR | TATT<u>GGTACC</u>TCAGGTTGGATCAACAGGCA | 50 |
| tyrRKO-F | ATAGTGTCATATCATCATATTAATTGTTCTTTTTTCAGGTGAAGGTTCCCTAGGTGACACTATAGAACGCG | 51 |
| tyrRKO-R | CGGCTGGTGATTTCGTCCAGCGAACCTTCCATCGCATCTTCGCCCACGGCTAGTGGATCTGATGGGTACC | 52 |
| tyrRKO-EXF | TTTCCGTCTTTGTGTCAATGATTGTTGACAGAAACCTTCCTGCTATCCAAATAGTGTCATATCATCATAT | 53 |
| tyrRKO-EXR | GCGTGCTGGGATAATTGCGATAAAGCTGGGTTAATACCGAGCGTTCAAAACGGCTGGTGATTTCGTCCAG | 54 |
| poxBKO-F | TTTCTCTCCCATCCCTTCCCCCTCCGTCAGATGAACTAAACTTGTTACCGGACACTATAGAACGCGGCCG | 55 |
| poxBKO-R | GCGCAGCATATACAGGCTGAAACCTTTGGCCTGTTCGAGTTTGATCTGCGCCGCATAGGCCACTAGTGGA | 56 |
| poxBKO-EXF | TATGCCCGATGATATTCCTTTCATCGGGCTATTTAACCGTTAGTGCCTCCTTTCTCTCCCATCCCTTCCC | 57 |
| poxBKO-EXR | TTTGTTTTCGCCAGTTCGATCACTTCATCACCGCGTCCGCTGATGATTGCGCGCAGCATATACAGGCTGA | 58 |
| pflBKO-F | TACCAAAGGTGACTGGCAGAATGAAGTAAACGTCCGTGACTTCATTCAGAGACACTATAGAACGCGGCCG | 59 |
| pflBKO-R | GCGAGTTGAAACGTACTGCGTAGCCAGATACACGGATGGTCAGCTGCGGACCGCATAGGCCACTAGTGGA | 60 |
| pflBKO-EXF | TGTTACATGTCCGAGCTTAATGAAAAGTTAGCCACAGCCTGGGAAGGTTTTACCAAAGGTGACTGGCAGA | 61 |
| pflBKO-EXR | AGATTGAGTGAAGGTACGAGTAATAACGTCCTGCTGCTGTTCTTTAGTCAGCGAGTTGAAACGTACTGCG | 62 |
| adhEKO-F | TGAACTTAACGCACTCGTAGAGCGTGTAAAAAAAGCCCAGCGTGAATATGGACACTATAGAACGCGGCCG | 63 |
| adhEKO-R | GCTTTTTTCTCAGCTTTAGCCGGAGCAGCTTCTTTCTTCGCTGCAGTTTCCCGCATAGGCCACTAGTGGA | 64 |
| adhEKO-EXF | AAAAAAGTTTAACATTATCAGGAGAGCATTATGGCTGTTACTAATGTCGCTGAACTTAACGCACTCGTAGAG | 65 |
| adhEKO-EXR | AGGGGCCGTTTATGTTGCCAGACAGCGCTACTGATTAAGCGGATTTTTTCGCTTTTTTCTCAGCTTTAGCCG | 66 |
| frdBKO-F | GCGGAAGCAGCCAATAAGAAGGAGAAGGCGAATGGCTGAGATGAAAAACCGACACTATAGAACGCGGCCG | 67 |
| tyrBKO-F | GTGTTTCAAAAAGTTGACGCCTACGCTGGCGACCCGATTCTTACGCTTATTAGGTGACACTATAGAACGCG | 68 |
| tyrBKO-R | TGGCAATGGCGCGAATAGCGTAGGCATCCTCTTCCATACCGGCACCAAATTAGTGGATCTGATGGGTACC | 69 |
| tyrBKO-EXF | CCGGTTATTGTGTTTTAACCACCTGTCCCGTAAACCTGGAGAACCATCGCGTGTTTCAAAAAGTTGACGC | 70 |
| tyrBKO-EXR | GGAGAAAATTTTCGAGAACGAATTGCTCACCAGAGCGGGTAATCCAGCGCTGGCAATGGCGCGAATAGCG | 71 |

TABLE 3-continued

| Primer | Sequence | SEQ ID NO |
|---|---|---|
| aspCKO-F | ATGTTTGAGAACATTACCGCCGCTCCTGCCGACCCG ATTCTGGGCCTGGCTAGGTGACACTATAGAACGCG | 72 |
| aspCKO-R | TAGCCGCGAAAGCGCGCAGTCCTTCAGCATCTTCTT CCAGACCACGGGCATAGTGGATCTGATGGGTACC | 73 |
| aspCKO-EXF | CGTTACCCTGATAGCGGACTTCCCTTCTGTAACCAT AATGGAACCTCGTCATGTTTGAGAACATTACCGC | 74 |
| aspCKO-EXR | CAGGCCAAAGTTTTTAGAGTAGGAACTGGCAACAAT CAGCTCTTTATGCATAGCCGCGAAAGCGCGCAGT | 75 |
| PhaAB-BamF | TATAGGATCCCGGGCAAGTACCTTGCCGAC | 76 |
| PhaAB-sbR | TATCAAGCTTTCAGCCCATATGCAGGCCGC | 77 |
| 100-Kpn-F | TATTGGTACCTTGACGGCTAGCTCAGTCCTAGGTAC AGTGCTAGCGAATTCACAGGAAACAGACCATGACTG ACGTTGTCATCGT | 78 |
| PhaB-Bam-R | TATTGGATCCTCAGCCCATATGCAGGCCGC | 79 |
| 105-Kpn-F | TATTGGTACCTTTACGGCTAGCTCAGTCCTAGGTAC TATGCTAGCGAATTCACAGGAAACAGACCATGACTG ACGTTGTCATCGT | 80 |
| 114-Kpn-F | TATTGGTACCTTTATGGCTAGCTCAGTCCTAGGTAC AATGCTAGCGAATTCACAGGAAACAGACCATGACTG ACGTTGTCATCGT | 81 |
| 109-Kpn-F | TATTGGTACCTTTACAGCTAGCTCAGTCCTAGGGAC TGTGCTAGCGAATTCACAGGAAACAGACCATGACTG ACGTTGTCATCGT | 82 |
| 103-Kpn-F | TATTGGTACCCTGATAGCTAGCTCAGTCCTAGGGAT TATGCTAGCGAATTCACAGGAAACAGACCATGACTG ACGTTGTCATCGT | 83 |
| ldhAKO-F | ACAGGTGAACGAGTCCTTTGGCTTTGAGCTGGAATT TTTTGACTTTCTGCGACACTATAGAACGCGGCCG | 84 |
| ldhAKO-R | TTGCTTAAGTTTTGCAGCGTAGTCTGAGAAATACTG GTCAGAGCTTCTGCCCGCATAGGCCACTAGTGGA | 85 |
| ldhAKO-EXF | ATGAAACTCGCCGTTTATAGCACAAAACAGTACGAC AAGAAGTACCTGCAACAGGTGAACGAGTCCTTTG | 86 |
| ldhAKO-EXR | AGCGGCAAGATTAAACCAGTTCGTTCGGGCAGGTTT CGCCTTTTTCCAGATTGCTTAAGTTTTGCAGCGT | 87 |
| ldhArep-R | TTGCTTAAGTTTTGCAGCGTAGTCTGAGAAATACTG GTCAGAGCTTCTGCTGAGCGGATACATATTTGAATG TATTT | 88 |

Example 1: Preparation of Recombinant 2-Hydroxyisocapronate CoA-Transferase

An enzyme using acetyl-CoA as a CoA donor and having a broad spectrum of aromatic substrates was found. Sequence similarity analysis was performed to identify homologous enzymes for FldA, and 2-isocaprenoyl-CoA:2-hydroxyisocaproate CoA-transferase of *Clostridium difficile* (HadA, SEQ ID NO: 1), which has an amino acid sequence identity of 48% or more with FldA, was screened from various FldAs having different origins (FIG. 2).

In order to produce a recombinant vector containing a gene encoding HadA, PCR was performed using the chromosomal DNA of *Clostridium difficile* 630 strain as a template, and HadA-hisF and HadA-hisR as primers to produce a his_HadA gene fragment encoding a 2-hydroxyisocaproate-CoA transferase having a his-tag at the C terminus thereof.

Figure 2:
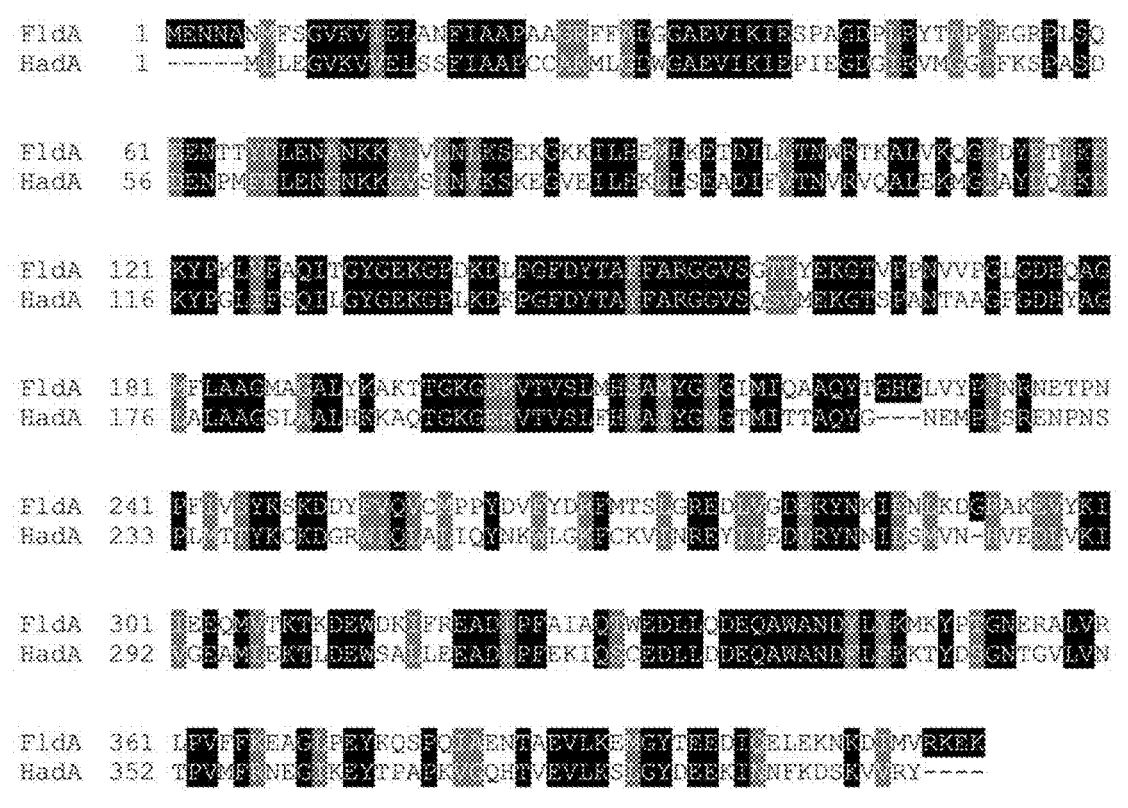

Next, the his_HadA fragment thus produced and the pET22b plasmid, which conducted strong gene expression of the T7 promoter, were treated with restriction enzymes (NdeI and NotI) and then the his_HadA fragment cleaved with the restriction enzyme was ligated with the pET22b plasmid using a T4 DNA ligase to produce pET22b_hisHadA as a recombinant plasmid (FIG. 2).

Figure 3:
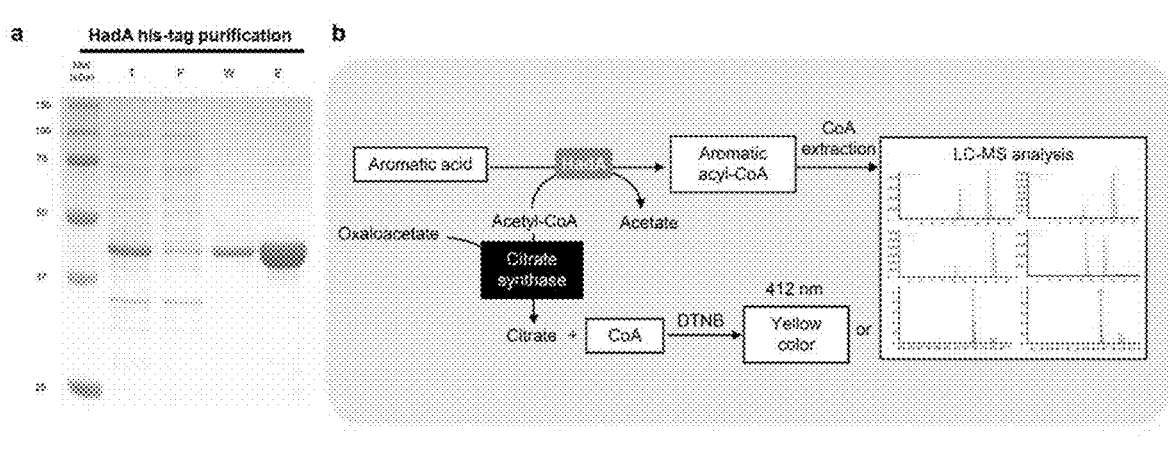
FIG. 3 in panel a shows the results of purification of HadA using His-tag, and in panel B shows the results of identification as to whether or not HadA is capable of using acetyl-CoA as a CoA donor.

The pET22b_hisHadA was introduced into *E. coli* XL1-Blue (Stratagene Cloning Systems, USA), cultured and added with IPTG to induce HadA expression. Then, HadA was purified in the culture medium using His-tag in a Ni-NTA spin kit (Quiagen, Germany) (FIG. 3A FIG. 3 in panel a).

Example 2: Identification of Substrate Diversity of 2-Hydroxyisocaproate CoA-Transferase In order to identify whether or not HadA is capable of using acetyl-CoA as a donor, in-vitro assays were performed using HadA prepared in Example 1.

10 µg of HadA was added to 50 mM phosphate buffer (pH 7.5) containing 0.1 mM acetyl-CoA and a 10 mM substrate, and the reaction was carried out at 30° C. for 10 minutes. After the reaction, 0.1 mM oxaloacetic acid, 5 µg of citrate synthase and 0.5 mM 5,5'-dithiobis-(2-nitrobenzoic acid) (DTNB) were added. Then, the amount of released CoA was analyzed by measuring the absorbance at 412 nm (FIG. 3 in panel b).

Analysis of the resulting aliphatic and aromatic acyl-CoA was performed on LC-MS (Agilent 1100 series and LC/MSD VL, Agilent) equipped with an Eclipse XDB-C18 column (5 µm, 4.6×150 mm, Agilent).

Figure 4:
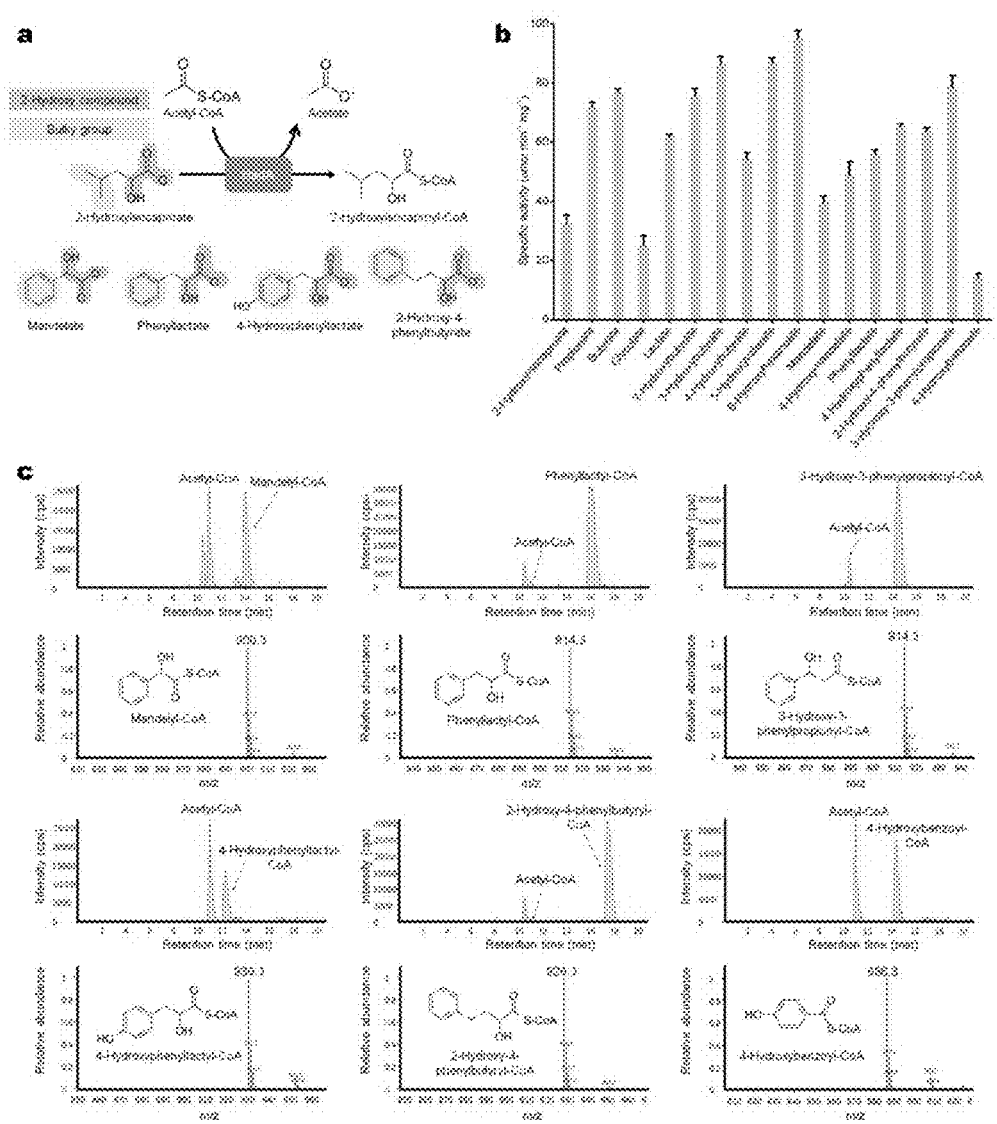
FIG. 4 shows the results of in-vitro assays, followed by LC-MS analysis identifying whether or not HadA is capable of converting mandelate, 4-hydroxymandelate, phenyllactate, 4-hydroxyphenyllactate, 2-hydroxy-4-phenylbutyrate, 3-hydroxy-3-phenylpropionate and 4-hydroxybenzoic acid to the corresponding CoA derivatives using acetyl-CoA as a CoA donor.

As a result, as can be seen from FIG. 4, HadA is capable of using acetyl-CoA as a donor and of using mandelate, 4-hydroxymandelate, phenyllactate, 4-hydroxyphenyllactate, 2-hydroxy-4-phenylbutyrate, 3-hydroxy-3-phenylpropionate and 4-hydroxybenzoic acid as substrates for conversion to the corresponding CoA derivatives.

Figure 5:
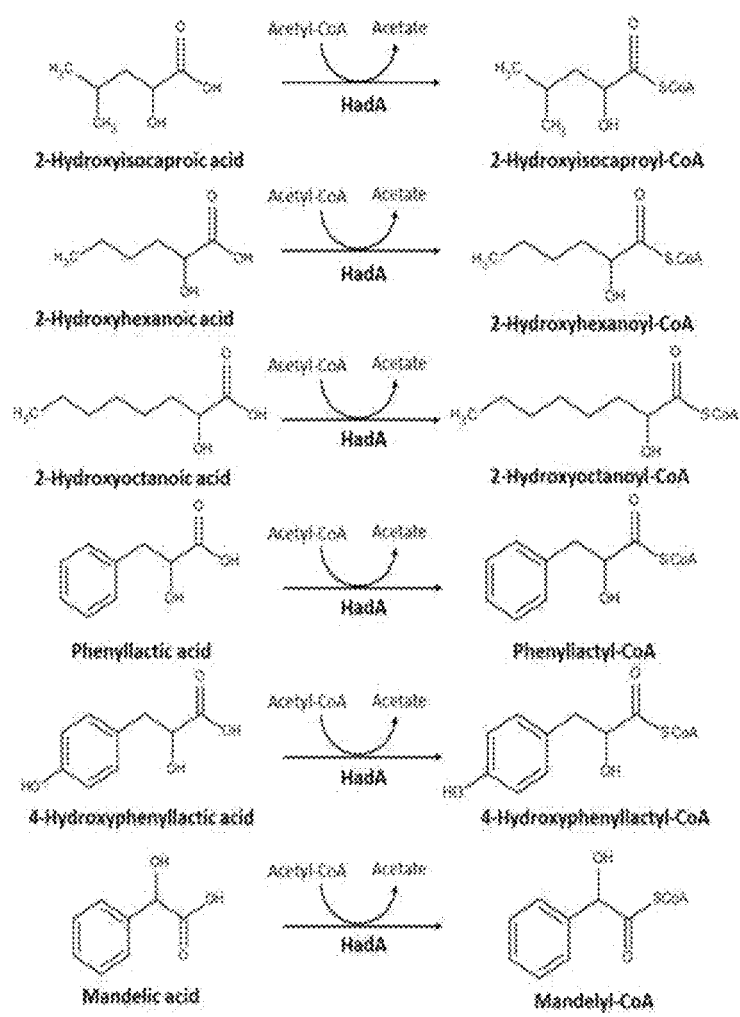
FIG. 5 shows molecular formulae of CoA conversion reactions of various substrates that can be carried out using HadA.
Figure 6:
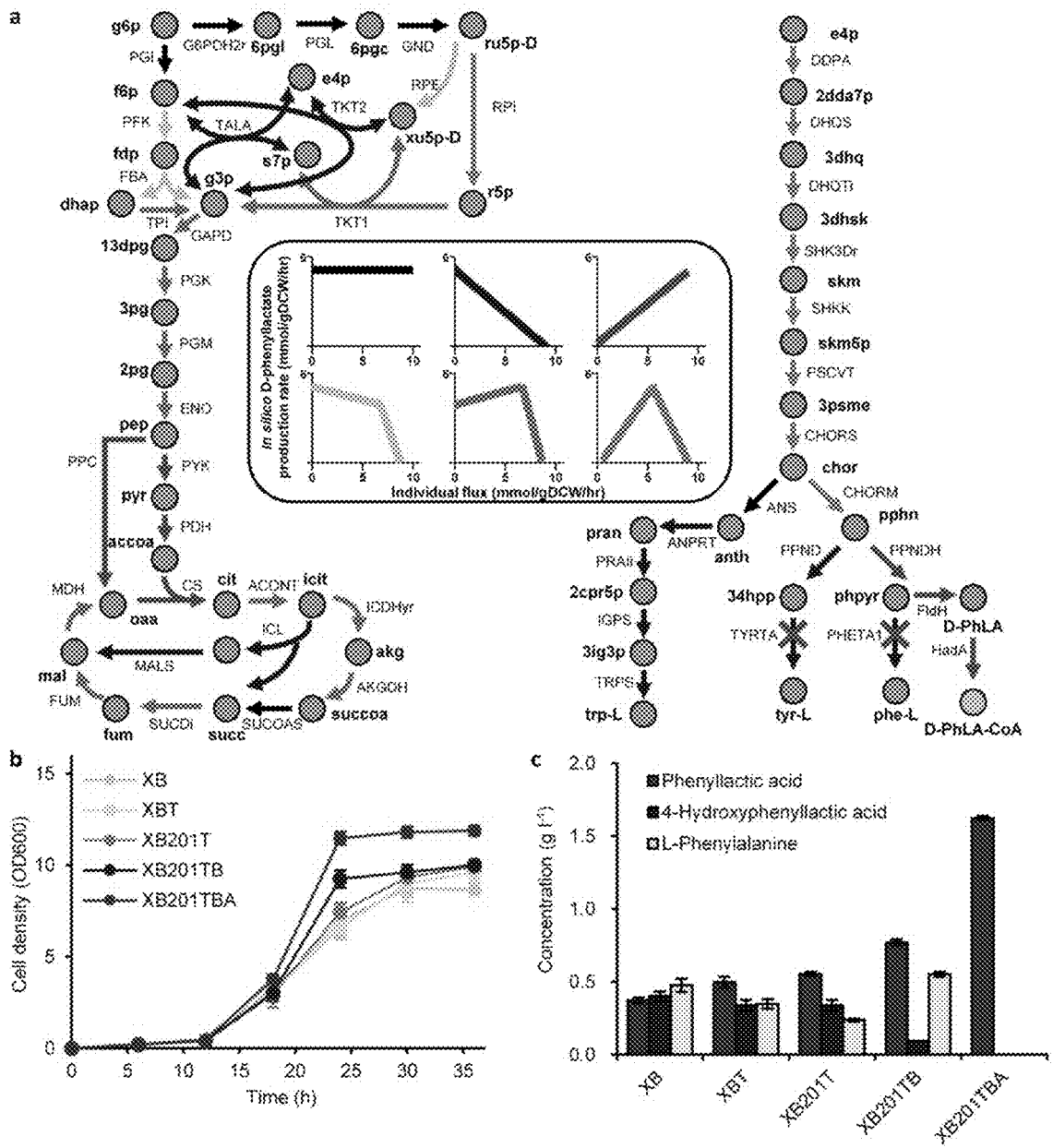
FIG. 6 shows the results of metabolic engineering analysis according to in-silico genome scale metabolism flux analysis to increase the production of D-phenyllactate.

FIG. 5 shows the molecular formulae of CoA conversion reactions of various substrates that can be converted by HadA.

Example 3: Production of Recombinant Strain with Increased Aromatic Monomer Production

*E. coli* was engineered to produce D-phenyllactate from glucose in vivo. The biosynthesis of aromatic compounds begins with the synthesis of 3-deoxy-D-arabino-heptulosonate-7-phosphate (DAHP), which is synthesized by the condensation of phosphoenolpyruvate (PEP) and erythrose-4-phosphate (E4P). The produced DAHP is converted into phenylpyruvate (PPA), which is then converted into D-phenyllactate through D-lactate dehydrogenase (FldH) (FIG. 1). The metabolic pathway for aromatic compound biosynthesis is known to be controlled by various inhibition mechanisms in a complicated manner. The expression of the DAHP synthase encoded by aroG and the chorismate mutase/prephenate dehydrogenase encoded by pheA is inhibited by L-phenylalanine (Ribe, D. E. et al., J. Bacteriol. 127:1085, 1976).

In the present invention, feedback-inhibition-resistant mutants, AroGfbr [AroG (D146N)] and PheAfbr [PheA (T326P)], were constructed to release the feedback inhibition by L-phenylalanine (Zhou, H. Y. et al., Bioresour.

Technol. 101:4151, 2010; Kikuchi, Y. et al., Appl. Environ. Microbiol. 63:761, 1997). *E. coli* XL1-Blue expressing AroGfbr, PheAfbr and FldH of *C. botulinum* A str. ATCC 3502 was produced.

Figure 7:
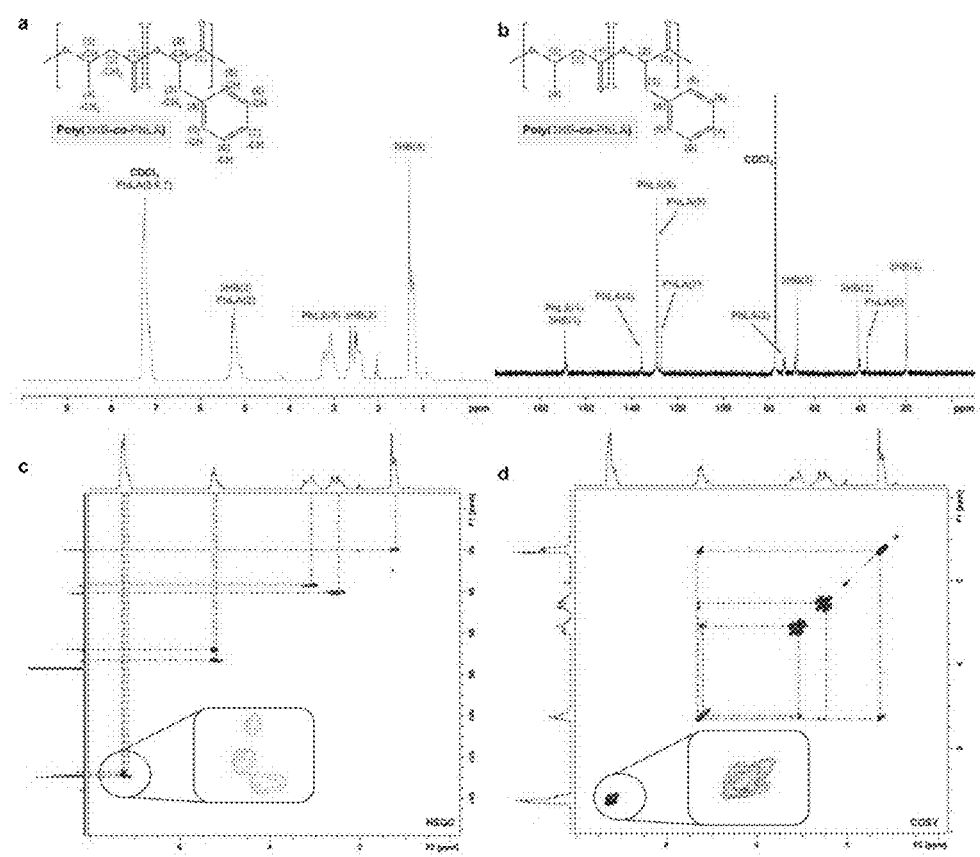
FIG. 7 shows the results of analysis of poly(3HB-co-D-phenyllactate) produced by E. coli XB201TBAL.
Figure 10:
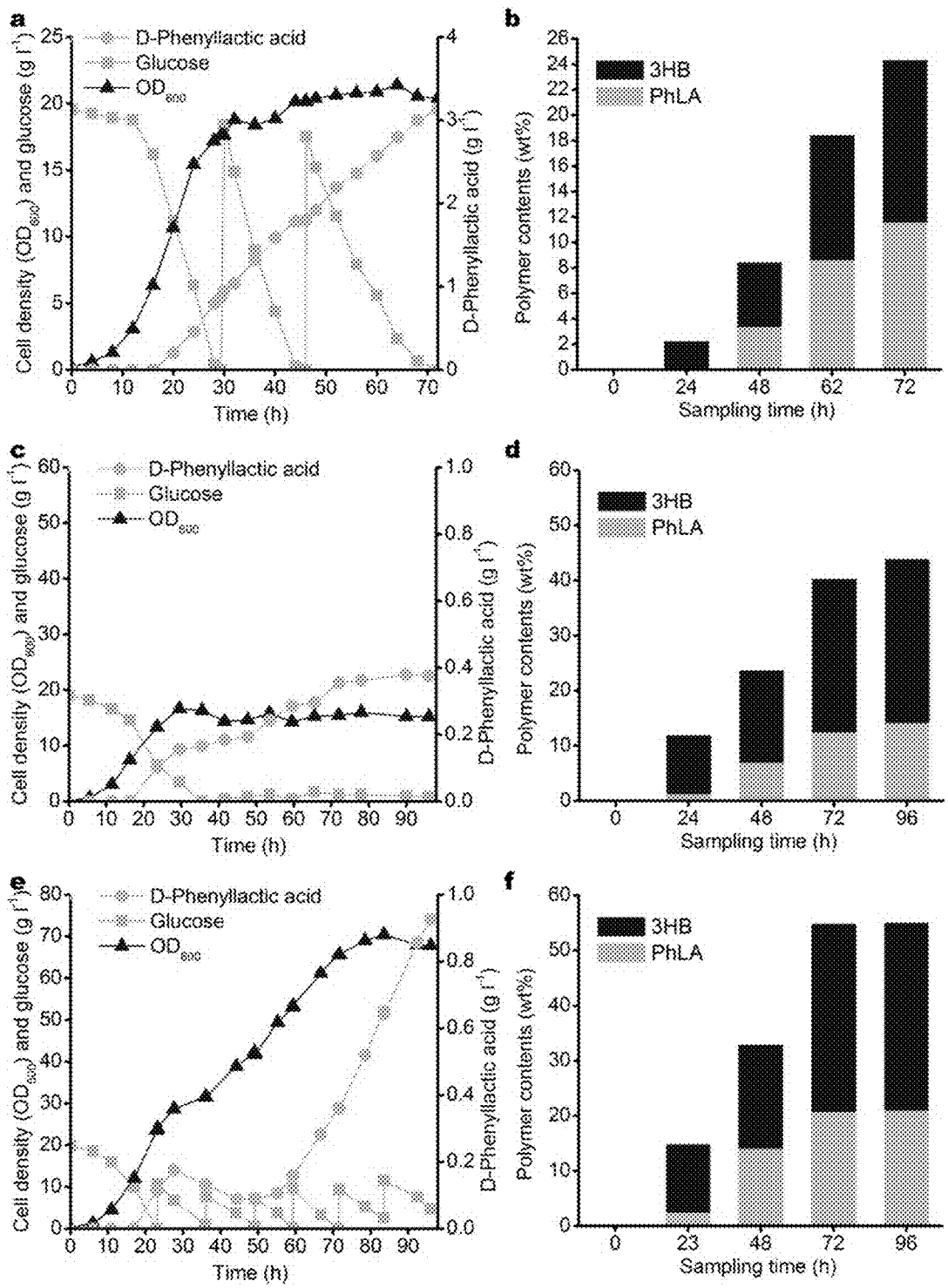
FIG. 10 in graphs a and b shows results of production of poly(3HB-co-D-phenyllactate) through fed-batch fermentation of the E. coli XB201TBAL strain expressing AroGfbr, PheAfbr, FldH, HadA and PhaC1437 in an MR medium containing 3HB, in graphs c and d shows the results of production of poly(3HB-co-D-phenyllactate) through fed-batch fermentation of the E. coli XB201TBAL strain expressing AroGfbr, PheAfbr, FldH, HadA, PhaC1437 and PhaAB under the promoter BBa_J23114, without addition of 3HB, and in graphs e and f the results of production of poly(3HB-co-D-phenyllactate) through fed-batch fermentation of the E. coli XB201TBAF strain expressing AroGfbr, PheAfbr, FldH, HadA, and PhaAB under the promoter of PhaC1437, without external addition of 3HB.

In order to construct pKM212-AroGfbr, a PCR product was obtained from a 3-deoxy-D-arabino-heptulosonate-7-phosphate synthase gene (aroG), which is a feedback-inhibiting resistance mutant, using AroG-F and AroG-R as primers and using pTyr-a plasmid as a template (Na, D. et al., Nature Biotechnol. 31: 170, 2013), and the PCR product was ligated to pKM212-MCS with restriction enzymes site (EcoRI/HidIII) (Park, S J et al., Metab. Eng. 20:20, 2013) to produce pKM212-AroGfbr.

The pKM212-AroGfbrPheAfbr plasmid was constructed as follows. First, a DNA fragment of 991 bp was amplified by PCR from the genomic DNA of *E. coli* using PheA-F and PheAmut-R as primers of a single mutated nucleotide (T976G). Second, a DNA fragment of 200 bp was amplified from the genomic DNA of *E. coli* using PheA-R and PheAmut-F as primers of a single mutated nucleotide (A976C).

Then, a DNA fragment of 1161 bp was amplified by overlap PCR using PheA-F and PheA-R as primers and two mixed fragments as templates. The PCR product was ligated to the pKM212-AroGfbr produced above using a restriction enzyme (HindIII).

D-lactate dehydrogenase (fldH) of *C. botulinum* A str. ATCC 3502 was used for construction of pACYC-FldH. The codon usage of fldH genes was optimized for *E. coli* and the fldH gene optimized for *E. coli* was amplified using FldH-F and FldH-R as primers and pUC57-FldHopt (GenScript, Piscataway, N.J., USA) as a template.

The PCR product was ligated with pTrc99A (Pharmacia, Biotech, Sweden) using restriction enzymes (BamHI/HindIII) to construct pTrc-FldH. Next, the fldH gene combined with the trc promoter and the rrnB terminator was amplified through PCR using Trc-F and Ter-R as primers and pTrc-FldH as a template. The amplified PCR product was ligated with pACYC184KS (Korean Patent Laid-Open No. 2015-0142304) using restriction enzymes (XhoI/SacI) to obtain pACYC-FldH.

The pKM212-AroGfbrPheAfbr and pACYC-FldH thus produced were introduced into *E. coli* XL1-Blue to produce a recombinant *E. coli* expressing AroGfbr, PheAfbr and FldH.

The *E. coli* produced 0.372 g/L of D-phenyllactate when cultured in MR medium containing 15.2 g/L of glucose.

The MR medium contained 6.67 g of $KH_2PO_4$, 4 g of $(NH_4)_2HPO_4$, 0.8 g of $MgSO_4.7H_2O$, 0.8 g of citrate and 5 ml of a trace metal solution per liter, and the trace metal solution contained 0.5 M HCl: 10 g of $FeSO_4.7H_2O$, 2 g of $CaCl_2$, 2.2 g of $ZnSO_4.7H_2O$, 0.5 g of $MnSO_4.4H_2O$, 1 g of $CuSO_4.5H_2O$, 0.1 g of $(NH_4)_6Mo_7O_{24}.4H_2O$ and 0.02 g of $Na_2B_4O_7.10H_2O$.

In order to increase the production amount of aromatic monomers through metabolic engineering, the yields of *E. coli* XL1-Blue strains expressing AroGfbr, PheAfbr and FldH, producing small amounts of D-phenyllactate (0.372 g/L) from glucose, were increased through metabolic engineering. *E. coli* XBT strains expressing AroGfbr, PheAfbr and FldH were produced by deleting TyrR, which is a double transcription regulator that performs regulation to inhibit aromatic amino acid biosynthesis.

The deletion of the tyrR gene in *E. coli* expressing AroGfbr, PheAfbr and FldH was carried out using a one-step inactivation method (Datsenko, K. A. et al., Proc. Natl Acad Sci. USA 97: 6640, 2000).

The *E. coli* XBT strain was cultured in an MR medium containing 16.4 g/L of glucose. As a result, the strain produced 0.5 g/L of D-phenyllactate, which corresponded to productivity of 30% higher than the *E. coli* XL1-blue strain from which tyrR was not deleted.

In order to remove the pathway colliding with D-phenyllactate synthesis, *E. coli* XB201T was constructed by deleting poxB (a gene encoding a pyruvate oxidase), pflB (a gene encoding a pyruvate formate lyase), adhE (a gene encoding an acetaldehyde dehydrogenase/alcohol dehydrogenase) and frdB (a gene encoding a fumarate reductase) from *E. coli* XBT.

The *E. coli* XB201T strain produced 0.55 g/L of D-phenyllactate from 15.7 g/L of glucose, which corresponded to a yield 10% higher than that of *E. coli* XBT.

In addition, metabolic engineering analysis according to in-silico genome scale metabolism flux analysis was performed to further increase the production of D-phenyllactate.

For in-silico flux response analysis, the *E. coli* iJO1366 genome scale model, which consists of 2251 metabolism reactions and 1135 metabolites, was used, and the effects of central and aromatic amino acid biosynthesis on the production of D-phenyllactate were investigated. In order to reflect the same in the XB201T strain of the present invention, a heterologous metabolic reaction of D-phenyllactate biosynthesis (fldH gene) was further added to the model and the flux was fixed to zero to reflect the gene knockout in the model. The rate of D-phenyllactate production was maximized to a target function, while the central amino acid and aromatic amino acid biosynthesis reaction flux values were gradually increased from a minimum value to a maximum value. During the simulation, the glucose reaction rate was set at 10 mmol per 1 g of the dry cell weight on an hourly basis. All simulations were run in a Python environment using the Gurobi Optimizer 6.0 and the GurobiPy package (Gurobi Optimization, Inc. Houston, Tex.). Reading, writing and execution of COBRA-compliant SBML files were conducted using COBRApy32.

As a result, as shown in FIG. 6, a tyrB gene encoding a tyrosine aminotransferase and an aspC gene encoding an aspartic acid aminotransferase were removed from the *E. coli* strain XB201T to reduce the L-phenylalanine biosynthesis and thereby enhance the carbon flow to D-phenyllactate.

The *E. coli* strain XB201TBA prepared, as a result of the in-silico flux response analysis, was found to produce 1.62 g/L of D-phenyllactate from 18.5 g/L of glucose, resulting in a great increase in yield, namely 4.35 times higher than the D-phenyllactate production of the *E. coli* XL1-blue strain expressing AroGfbr, PheAfbr and FldH.

Example 4: Preparation of Polyhydroxyalkanoate Containing Aromatic Monomer using Recombinant Strain In order to prevent the formation of D-lactate in XB201TBA, the ldhA gene was further deleted to prepare XB201TBAL strain. In order to prepare polyhydroxyalkanoate containing aromatic monomers, PhaC1437 and HadA were expressed in the *E. coli* XB201TBAL strain.

In order to prepare a recombinant vector containing genes encoding PhaC1437 and HadA, PCR was performed using HadA-sbF and HadA-ndR as primers and the chromosomal DNA of *Clostridium difficile* 630 strain as a template, to produce a hadA gene fragment encoding a hydroxyisocaproate-CoA transferase. The amplified PCR product was ligated with p619C1437-pct540 (Yang, T. H. et al. Biotechnol. Bioeng. 105: 150, 2010) using restriction enzymes (SbfI/NdeI) to obtain p619C1437-HadA. The obtained p619C1437-HadA was introduced into *E. coli* XB201TBAL to prepare recombinant *E. coli* expressing AroGfbr, PheAfbr, FldH, PhaC1437 and HadA. The *E. coli* was cultured in MR medium containing 20 g/L of glucose and 1 g/L of sodium 3HB to obtain poly(52.1 mol % 3HB-co-47.9 mol % D-phenyllactate) in an amount of 15.8 wt % of the dry cell weight (FIG. 7). Also, poly(52.3 mol % 3HB-co-47.7 mol % D-phenyllactate) was produced in an amount of 24.3% by weight of dry cell weight through fed-batch fermentation (FIG. 10 in graphs a and b).

Example 5: Preparation of Polyhydroxyalkanoate Containing Various Aromatic Monomers Using Recombinant Strain In order to identify whether or not the system using *E. coli* XB201TBAL can be used for the preparation of various aromatic copolymers, experiments were conducted using mandelate as a monomer.

*E. coli* XB201TBAL expressing AroGfbr, PheAfbr, FldH, PhaC1437 and HadA were cultured in an MR medium containing 1 g/L of sodium 3HB and 0.5 g/L of D-mandelate. As a result, poly(55.2 mol % 3HB-co-43.0 mol % D-phenyllactate-co-1.8 mol % D-mandelate) was produced in an amount of 11.6 wt % of the dry cell weight (FIG. 8 in spectra a and b), thereby successfully preparing an aromatic polymer containing D-mandelate using D-mandelate as a substrate.

Next, D-mandelate was prepared in vivo through metabolic engineering. A hydroxymandelate synthase (HmaS) derived from *Amycolatopsis orientalis*, a hydroxymandelate oxidase (Hmo) of *S. coelicolor*, and D-mandelate dehydrogenase (Dmd) of *Rhodotorula graminis* were expressed in *E. coli* XB201TBAL expressing AroGfbr, PheAfbr, FldH, PhaC1437 and HadA in order to produce D-mandelate from glucose.

For construction of pKM212-HmaS, the plasmid pUC57-HmaSopt was prepared by using the hydroxymandelate synthase gene (hmaS) of *A. orientalis* and cloning the codon into a synthetic vector in *E. coli* (GenScript, Piscataway, N.J., USA).

The pUC57-HmaSopt was ligated to pKM212-MCS using a restriction enzyme (EcoRI/KpnI). In order to construct pKM212-HmaSHmo, the codon-optimized hmo gene (GenScript, Piscataway, N.J., USA) was synthesized using the hydroxymandelate oxidase gene (hmo) of *S. coelicolor* and was amplified through PCR using Hmo-F and Hmo-R as primers. The PCR product was ligated with pKM212-HmaS using restriction enzymes (KpnI/BamHI) to construct pKM212-HmaSHmo.

In order to construct pKM212-HmaSHmoDmd, pUC57-Dmd containing the *E. coli* codon-optimized dmd gene was synthesized (GenScript, Piscataway, N.J., USA) and an *E. coli* codon-optimized *R. graminis* D-mandelate dehydrogenase gene (dmd) was amplified through PCR using Dmd-F and Dmd-R as primers. The PCR product was ligated with pKM212-HmaSHmo using restriction enzymes (BamHI/SbfI) to prepare pKM2l2-HmaSHmoDmd.

The prepared pKM212-HmaSHmoDmd was introduced into *E. coli* XB201TBAL expressing AroGfbr, PheAfbr, FldH, PhaC1437 and HadA to construct a recombinant strain having the potential to produce mandelate.

The constructed recombinant strain having the potential to produce mandelate was cultured in a medium containing 20 g/L of glucose and 1 g/L of sodium 3HB. As a result, poly(92.9 mol % 3HB-co-6.3 mol % D-phenyllactate-co-0.8 mol % D-mandelate) was produced in an amount of 16.4 wt % of the dry cell weight.

The production of an aromatic polymer using 3-hydroxy-3-phenylpropionate (3HPh) as another aromatic monomer was identified. When the *E. coli* strain XB201TBAL was cultured in a medium containing 20 g/L of glucose, 0.5 g/L of 3-hydroxy-3-phenylpropionic acid and 1 g/L of sodium 3HB, poly(33.3 mol % 3HB-co-18 mol % D-phenyllactate-co-48.7 mol % 3HPh) was produced in an amount of 14.7% by weight of dry cell weight (FIG. 8 in spectra c and d). These results suggest that a system using the 2-hydroxyisocaproate-CoA transferase developed in the present invention can be widely used for the production of various aromatic polyesters.

Example 6: Preparation of Polyhydroxyalkanoate Containing Various Long-Chain 2-HA using Recombinant Strain In order to identify whether or not the system using 2-hydroxyisocaproate-CoA transferase of the present invention can be used for the production of polyhydroxyalkanoates containing various long-chain 2-HA, polymer productivity was confirmed using various long-chain 2-HA monomers [2-hydroxyisocaproate (2HIC), 2-hydroxyhexanoate (2HH) and 2-hydroxyoctanoate (2HO)]. *E. coli* XL1-Blue expressing PhaC1437 and HadA was cultured in an MR medium containing 1 g/L of 3HB, 20 g/L of glucose and different concentrations (0.25, 0.5 and 1 g/L) of long-chain 2-HA. As a result, a copolymer containing hydroxyisocaproate, 2-hydroxyhexanoate or 2-hydroxyoctanoate was prepared. In addition, it was confirmed that, as the concentration of 2-HA contained in the medium increased, the mole fraction of the monomer contained in the copolymer increased (Tables 4, 5 and 6).

TABLE 4

| 2HIC concentration (g/L) | PHA content (wt %) | 2HIC (mol %) | 3HB (mol %) | LA (mol %) |
|---|---|---|---|---|
| 0.25 | 21.3 ± 0.3 | 12.4 ± 0.8 | 83.8 ± 2.3 | 3.8 ± 3.1 |
| 0.5 | 24.0 ± 0.7 | 25.8 ± 2.4 | 70.0 ± 2.4 | 4.2 ± 1.5 |
| 1 | 35.3 ± 0.3 | 74.0 ± 14.6 | 23.2 ± 13.8 | 2.8 ± 0.9 |

TABLE 5

| 2HH concentration (g/L) | PHA content (wt %) | 2HH (mol %) | 3HB (mol %) | LA (mol %) |
|---|---|---|---|---|
| 0.25 | 15.9 ± 0.5 | 17.2 ± 1.2 | 63.5 ± 5.8 | 19.3 ± 4.6 |
| 0.5 | 21.3 ± 5.5 | 35.1 ± 1.5 | 39.5 ± 1.0 | 25.4 ± 1.7 |
| 1 | 23.7 ± 0.3 | 52.3 ± 2.5 | 29.4 ± 2.5 | 18.3 ± 1.8 |

TABLE 6

| 2HO concentration (g/L) | PHA content (wt %) | 2HO (mol %) | 3HB (mol %) | LA (mol %) |
|---|---|---|---|---|
| 0.25 | 16.8 ± 1.6 | 20.3 ± 3.8 | 72.4 ± 3.8 | 7.3 ± 0.1 |
| 0.5 | 13.7 ± 0.7 | 39.3 ± 1.6 | 54.4 ± 2.5 | 6.3 ± 1.0 |
| 1 | 16.4 ± 0.4 | 44.3 ± 1.0 | 47.1 ± 0.3 | 8.6 ± 0.8 |

Example 7: Preparation of Polyhydroxyalkanoate Containing Aromatic Monomers with Various Mole Fractions Through Synthetic-Promoter-Based Flux Control In order to produce a strain producing aromatic PHA without the supply of 3HB from the outside, R. eutropha β-ketothiolase (PhaA) and acetoacetyl-CoA reductase (PhaB) were further expressed in an XB201TBAL strain, and whether or not aromatic PHA was prepared from glucose without the external supplementation of 3HB was identified.

As a result, as expected, the XB201TBAL strain expressing AroGfbr, PheAfbr, FldH, PhaC1437 and HadA produced poly(86.2 mol % 3HB-co-13.8 mol % D-phenyllactate) from 20 g/L of glucose in an amount of 18.0 wt % of the dry cell weight. In addition, the production of aromatic PHAs having various monomer mole fractions important for industrial applications was attempted by controlling the metabolic flux catalyzed by PhaAB using the synthetic Anderson promoter (http://parts.igem.org/). Five different plasmids expressing PhaAB with five different promoters of different strength (SEQ ID NOS: 89-93) were prepared and introduced into XB201TBAL strains expressing AroGfbr, PheAfbr, FldH, PhaC1437 and HadA.

As PhaAB expression decreased, the mole fraction of D-phenyllactate monomers increased; copolymers having 11.0 mol %, 15.8 mol %, 20.0 mol %, 70.8 mol % and 84.5 mol % of D-phenyllactate could be prepared (FIG. 9, showing in diagram a the synthetic promoters BBa_J23100 (SEQ ID NO: 89), BBa_J23105 (SEQ ID NO: 90), BBa_J23114 (SEQ ID NO: 91), BBa_J23109 (SEQ ID NO: 92), and BBa_J23103 (SEQ ID NO: 93), and showing in graph b the D-phenyllactate monomer fraction (mole percent) for such promoters; and Table 7); poly(15.5 mol % 3HB-co-84.5 mol % D-phenyllactate) was produced in an amount of 4.3 wt % of the dry cell weight by expressing PhaAB with the BBa_J23103 promoter (FIG. 9 in graph b). These results suggest that aromatic polyesters having various aromatic monomer mole fractions can be produced by controlling the metabolic flux.

TABLE 7

| Synthetic promoters | Mole fraction (mol % ± s.d.) | | Molecular weight (Da) | | | Tg (° C.) |
|---|---|---|---|---|---|---|
| | 3HB | PhLA | $M_n$ | $M_w$ | $M_w/M_n$ | |
| BBa_J23100 | 89.0 ± 0.8 | 11.0 ± 0.5 | 24920 | 50120 | 2.01 | 9.41 |
| BBa_J23105 | 84.2 ± 2.7 | 15.8 ± 0.4 | 22470 | 45460 | 2.02 | 10.05 |
| BBa_J23114 | 80.0 ± 1.8 | 20.0 ± 1.3 | 15760 | 25850 | 1.64 | 15.64 |
| BBa_J23109 | 29.2 ± 1.1 | 70.8 ± 1.2 | 2665 | 4184 | 1.57 | 29.04 |
| BBa_J23103 | 15.5 ± 0.6 | 84.5 ± 3.3 | 3569 | 4588 | 1.29 | 33.47 |

Example 8: Preparation of Aromatic Polyhydroxyalkanoate Through Fed-Batch Fermentation In this example, pH-stat culturing of the E. coli strain XB201TBAL expressing AroGfbr, PheAfbr, FldH, HadA, PhaC1437 and PhaAB under the promoter BBa_J23114 was performed without the supply of 3HB. After 96 hours of culture, poly(67.6 mol % 3HB-co-32.4 mol % D-phenyllactate) with a polymer content of 43.8 wt % of the dry cell weight was produced at 2.5 g/L (FIG. 10 in graphs c and d).

Also, in order to further improve the production of aromatic polyhydroxyalkanoate, the gene expression system was optimized by replacing the ldhA gene of the E. coli XB201TBA chromosome with the fldH gene. In addition, the expression of the fldH gene was increased by replacing the natural promoter of the ldhA gene with a strong trc promoter. Fed-batch fermentation including feeding glucose using a pulse feeding method was performed. The E. coli strain XB201TBAF expressing AroGfbr, PheAfbr, FldH, HadA, PhaC1437 and PhaAB under the promoter BBa_J23114 produced 13.9 g/L of poly(69.1 mol % 3HB-co-38.1 mol % D-phenyllactate) with a polymer content of 55.0 wt % of the dry cell weight through fed-batch fermentation (FIG. 10 in graphs e and f), and the production amount of 13.9 g/L was 5.56 times higher than 2.5 g/L, which is the amount produced by the E. coli XB201TBAL strain expressing AroGfbr, PheAfbr, FldH, HadA, PhaC1437 and PhaAB under the promoters BBa_J23114, and was much higher than that obtained through fed-batch culture of the E. coli XB201TBAL strain expressing AroGfbr, PheAfbr, FldH, HadA and PhaC1437 in the medium supplemented with glucose and 3HB. These results indicate that the aromatic polyhydroxyalkanoate can be successfully produced at a high concentration through fed-batch fermentation of the engineered strain (E. coli XB201TBAF strain expressing AroGfbr, PheAfbr, FldH, HadA, PhaC1437 and PhaAB under BBa_J23114 promoter).

Example 9: Analysis of Physical Properties of Polyhydroxyalkanoate Containing Aromatic Monomers Finally, the physical properties of aromatic PHAs produced by metabolically engineered E. coli were investigated.

The polyhydroxyalkanoate (PHA) content and monomer composition were determined through GC or GC-MS. The collected cells were washed three times with distilled water and lyophilized for 24 hours, and the PHA of the lyophilized cells was converted to the corresponding hydroxymethylester through acid-catalyzed methanolysis. The resulting methylester was purified using a GC apparatus (Agilent 6890N, Agilent, USA) equipped with an Agilent 7683 automatic injector, a frame ionization detector and a fused silica capillary column (ATTM-Wax, 30 m, ID 0.53 mm, thickness 1.20 μm, Alltech, USA). The polymer was extracted through chloroform extraction and purified in cells using solvent extraction. The structure, molecular weight and thermal properties of the polymer were measured using nuclear magnetic resonance (NMR), gel permeation chromatography (GPC) and differential scanning calorimetry (DSC).

As a result, FIG. 7 shows the results of analysis of poly(3HB-co-D-phenyllactate) produced by E. coli XB201TBAL and FIG. 8 shows the results of analysis of poly(3HB-co-D-phenyllactate-co-D-mandelate) produced by E. coli XB201TBAL.

The poly(52.1 mol % 3HB-co-47.9 mol % D-phenyllactate) was amorphous, and, as the mole fraction of D-phenyllactate in the copolymer increased, the Tg increased significantly to 23.86° C., in spite of the decreased molecular weight thereof. Also, the copolymer containing an aromatic compound in the polymer had decreased crystallinity. It is considered that the aromatic ring of the polymer interferes with the crystallization of P(3HB) (induced by stereochemistry). P(3HB) exhibited high brittleness due to strong crystallinity, whereas the resulting copolymer caused improved mechanical toughness due to lowered crystallinity and increased Tg.

Although the present invention have been described in detail with reference to specific configurations, those skilled in the art will appreciate that this description relates to preferred embodiments and should not be construed as limiting the scope of the present invention. Therefore, the substantial scope of the present invention is defined by the accompanying filed claims and equivalents thereto.

INDUSTRIAL APPLICABILITY

According to the present invention, a biodegradable polymer containing an aromatic monomer or a long-chain 2-HA monomer can be prepared.

Although specific configurations of the present invention have been described in detail, those skilled in the art will appreciate that this detailed description is provided as preferred embodiments and should not be construed as limiting the scope of the present invention. Therefore, the substantial scope of the present invention is defined by the accompanying filed claims and equivalents thereto.

[Sequence Listing Free Text]

An electronic file is attached.

---

The invention claimed is:

1. A recombinant microorganism capable of producing polyhydroxyalkanoate having an aromatic monomer or a long-chain 2-hydroxyalkanoate (2-HA) monomer, in which a gene encoding a 2-hydroxyisocaproate-CoA transferase HadA comprising the amino acid sequence of SEQ ID NO: 1 and a gene encoding a mutant enzyme of polyhydroxyalkanoate synthase comprising the amino acid sequence of SEQ ID NO: 2 in which the mutant enzyme comprises at least one mutation selected from the group consisting of E130D, S325T, L412M, 5477R, S477H, S477F, S477Y, S477G, Q481M, Q481K and Q481R, are introduced into a microorganism capable of producing acetyl-CoA from a carbon source, wherein the recombinant microorganism is capable of producing polyhydroxyalkanoate having an aromatic monomer or a long-chain 2-hydroxyalkanoate (2-HA) monomer.

2. The recombinant microorganism according to claim 1, wherein the 2-hydroxyisocaproate-CoA transferase uses acetyl-CoA as a CoA donor.

3. The recombinant microorganism according to claim 1, wherein the aromatic monomer or long-chain 2-HA monomer is selected from the group consisting of 2-hydroxyisocaproate, 2-hydroxyhexanoate, 2-hydroxyoctanoate, phenyllactate, 2-hydroxy-4-phenylbutyrate, 3-hydroxy-3-phenylpropionate, 4-hydroxybenzoic acid and mandelate.

4. The recombinant microorganism according to claim 1, wherein a gene encoding a β-ketothiolase and a gene encoding an acetoacetyl-CoA reductase are further introduced into the recombinant microorganism.

5. A method for producing polyhydroxyalkanoate having an aromatic monomer or a long-chain 2-hydroxyalkanoate (2-HA) monomer comprising:
   (a) culturing the recombinant microorganism according to claim 1 to produce polyhydroxyalkanoate having an aromatic monomer or a long-chain 2-HA monomer; and
   (b) recovering the produced polyhydroxyalkanoate having an aromatic monomer or a long-chain 2-HA monomer.

6. The method according to claim 5, wherein the recombinant microorganism is cultured in a medium containing an aromatic monomer or a long-chain 2-HA monomer.

7. The method according to claim 5, wherein the aromatic monomer or long-chain 2-HA monomer is selected from the group consisting of 2-hydroxyisocaproate, 2-hydroxyhexanoate, 2-hydroxyoctanoate, phenyllactate, 2-hydroxy-4-phenylbutyrate, 3-hydroxy-3-phenylpropionate, 4-hydroxybenzoic acid and mandelate.

8. The recombinant microorganism according to claim 1, wherein the gene selected from the group consisting of the following is further introduced:
   (i) the gene encoding DAHP (3-deoxy-D-arabino-heptulosonate-7-phosphate) synthase comprising the amino acid sequence of SEQ ID NO: 8;
   (ii) the gene encoding chorismate mutase/prephenate dehydrogenase comprising the amino acid sequence of SEQ ID NO: 9; and
   (iii) the gene encoding D-lactate dehydrogenase comprising the amino acid sequence of SEQ ID NO: 10,
   wherein the recombinant microorganism is capable of producing polyhydroxyalkanoate having phenyllactate as a monomer.

9. The recombinant microorganism according to claim 8, wherein a gene encoding a β-ketothiolase and a gene encoding an acetoacetyl-CoA reductase is further introduced into the recombinant microorganism; and
   at least one gene selected from the group consisting of a tyrR gene, a gene encoding a pyruvate oxidase, a gene encoding a pyruvate formate lyase, a gene encoding an acetaldehyde dehydrogenase, a gene encoding a fumarate reductase, a gene encoding a tyrosine aminotransferase, and a gene encoding an aspartic acid aminotransferase is further deleted from the recombinant microorganism.

10. A method for producing polyhydroxyalkanoate having phenyllactate as a monomer comprising:
    (a) culturing the recombinant microorganism according to claim 8 to produce polyhydroxyalkanoate having phenyllactate as a monomer; and
    (b) recovering the produced polyhydroxyalkanoate having phenyllactate as a monomer.

11. The recombinant microorganism according to claim 1, wherein the gene selected from the group consisting of the following is further introduced:
    (i) the gene encoding DAHP (3-deoxy-D-arabino-heptulosonate-7-phosphate) synthase comprising the amino acid sequence of SEQ ID NO: 8;
    (ii) the gene encoding chorismate mutase/prephenate dehydrogenase comprising the amino acid sequence of SEQ ID NO: 9; and
    (iii) the gene encoding D-lactate dehydrogenase comprising the amino acid sequence of SEQ ID NO: 10,
    (iv) the gene encoding hydroxymandelate synthase comprising the amino acid sequence of SEQ ID NO: 11,
    (v) the gene encoding hydroxymandelate oxidase comprising the amino acid sequence of SEQ ID NO: 12, and
    (vi) the gene encoding a D-mandelate dehydrogenase comprising the amino acid sequence of SEQ ID NO: 13,
    wherein the recombinant microorganism is capable of producing polyhydroxyalkanoate having mandelate as a monomer.

12. A method for producing polyhydroxyalkanoate having mandelate as a monomer comprising:
    (a) culturing the recombinant microorganism according to claim 11 to produce polyhydroxyalkanoate having mandelate as a monomer; and
    (b) recovering the produced polyhydroxyalkanoate having mandelate as a monomer.

13. A method for producing polyhydroxyalkanoate having, as a monomer, a compound selected from the group consisting of 2-hydroxyisocaproate, 2-hydroxyhexanoate and 2-hydroxyoctanoate, comprising:
    (a) culturing the recombinant microorganism according to claim 1 in a medium containing a compound selected from the group consisting of 2-hydroxyisocaproate, 2-hydroxyhexanoate and 2-hydroxyoctanoate; and
    (b) recovering polyhydroxyalkanoate containing, as a monomer, a compound selected from the group consisting of 2-hydroxyisocaproate, 2-hydroxyhexanoate and 2-hydroxyoctanoate.

14. The recombinant microorganism according to claim 11, wherein a gene encoding a (3-ketothiolase and a gene encoding an acetoacetyl-CoA reductase are further introduced into the recombinant microorganism.

* * * * *

UNITED STATES PATENT AND TRADEMARK OFFICE
CERTIFICATE OF CORRECTION

PATENT NO. : 10,961,521 B2  
APPLICATION NO. : 16/483426  
DATED : March 30, 2021  
INVENTOR(S) : Sang Yup Lee et al.

Page 1 of 1

It is certified that error appears in the above-identified patent and that said Letters Patent is hereby corrected as shown below:

In the Specification

Column 12, Line 61, "DH5a" should be -- DH5α --.

Column 22, Line 15, "FIG. 3A FIG. 3" should be -- FIG. 3 --.

In the Claims

Claim 1, Column 77, Line 67, "5477R" should be -- S477R --.

Claim 14, Column 80, Line 50, "(3-ketothiolase" should be -- β-ketothiolase --.

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*